United States Patent
Leiris et al.

(10) Patent No.: US 12,247,013 B2
(45) Date of Patent: Mar. 11, 2025

(54) INDANE DERIVATIVES FOR USE IN THE TREATMENT OF BACTERIAL INFECTION

(71) Applicant: Antabio SAS, Labege (FR)

(72) Inventors: Simon Leiris, Labege (FR); David Thomas Davies, Labege (FR); Martin Everett, Labege (FR); Nicolas Sprynski, Labege (FR); Lilha Beyria, Labege (FR); Thomas David Pallin, Margate (GB); Andrew Peter Cridland, Margate (GB); Toby Jonathan Blench, Margate (GB); Richard Leonard Elliott, Margate (GB); David Edward Clark, Margate (GB)

(73) Assignee: Antabio SAS, Labege (FR)

( * ) Notice: Subject to any disclaimer, the term of this patent is extended or adjusted under 35 U.S.C. 154(b) by 861 days.

(21) Appl. No.: 17/277,535

(22) PCT Filed: Jul. 25, 2019

(86) PCT No.: PCT/EP2019/070116
§ 371 (c)(1),
(2) Date: Mar. 18, 2021

(87) PCT Pub. No.: WO2020/064174
PCT Pub. Date: Apr. 2, 2020

(65) Prior Publication Data
US 2022/0112169 A1 Apr. 14, 2022

(30) Foreign Application Priority Data

Sep. 25, 2018 (EP) .................................. 18290106
Sep. 26, 2018 (EP) .................................. 18290104
Sep. 27, 2018 (EP) .................................. 18197365

(51) Int. Cl.
C07D 277/64 (2006.01)
A61K 45/06 (2006.01)
(Continued)

(52) U.S. Cl.
CPC ............ C07D 277/64 (2013.01); A61K 45/06 (2013.01); A61P 31/04 (2018.01); C07D 417/06 (2013.01); C07D 417/12 (2013.01)

(58) Field of Classification Search
CPC .. C07D 277/64; C07D 417/06; C07D 417/12; A61P 31/04
See application file for complete search history.

(56) References Cited

U.S. PATENT DOCUMENTS 5,457,196 A 10/1995 Warshawsky et al.
5,532,257 A 7/1996 Hase et al.
(Continued)

FOREIGN PATENT DOCUMENTS

DE 43 39 198 5/1995
EP 0 117 429 9/1984
(Continued)

OTHER PUBLICATIONS

Fei et al., "Recent progress of pseudomonas aeruginosa pneumonia" *Int. J. Respir.* 26(4):250-252, Apr. 2006 with English Translation.
(Continued)

*Primary Examiner* — Matthew P Coughlin
*Assistant Examiner* — Ashli Ariana Chicks
(74) *Attorney, Agent, or Firm* — Klarquist Sparkman, LLP

(57) ABSTRACT

The invention relates to an indane compound according to Formula (I), or a pharmaceutically acceptable salt thereof,
(Continued)

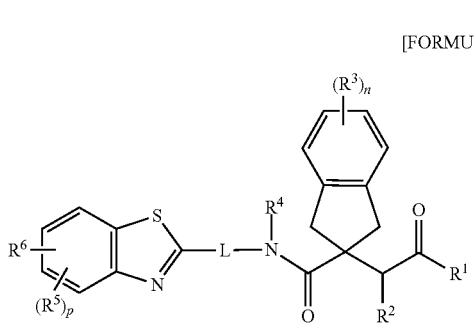

[FORMULA (I)]

wherein $R^1$, $R^2$, $R^3$, $R^4$, $R^5$, $R^6$, L, n and p are as defined herein. The compounds are useful for treating antibacterial infection either as stand-alone antibiotics, or in combination with further antibiotics.

25 Claims, 2 Drawing Sheets

(51) Int. Cl.
*A61P 31/04* (2006.01)
*C07D 417/06* (2006.01)
*C07D 417/12* (2006.01)

(56) References Cited

U.S. PATENT DOCUMENTS

| | | | |
|---|---|---|---|
| 5,688,818 | A | 11/1997 | Hosono et al. |
| 10,934,302 | B1 | 3/2021 | Taylor et al. |
| 11,000,511 | B2 * | 5/2021 | Leiris ............... C07D 513/04 |
| 2002/0128290 | A1 | 9/2002 | Ohshima et al. |
| 2004/0180941 | A1 | 9/2004 | Hepworth |
| 2006/0223830 | A1 | 10/2006 | De Nanteuil et al. |
| 2010/0113462 | A1 | 5/2010 | Caulfield et al. |
| 2012/0122764 | A1 | 5/2012 | Karki et al. |
| 2015/0282483 | A1 | 10/2015 | Sawada et al. |
| 2021/0347748 | A1 | 11/2021 | Leiris et al. |
| 2022/0041560 | A1 | 2/2022 | Selby et al. |

FOREIGN PATENT DOCUMENTS

| | | | | |
|---|---|---|---|---|
| JP | H 11-130761 | | 5/1995 | |
| JP | 11130761 | A * | 5/1999 | |
| WO | WO 98/003202 | | 1/1998 | |
| WO | WO 2003/011842 | | 2/2003 | |
| WO | WO 2003/089418 | | 10/2003 | |
| WO | WO 2003/094889 | | 11/2003 | |
| WO | WO 2005/016249 | | 2/2005 | |
| WO | WO 2006/029153 | | 3/2006 | |
| WO | WO 2006/122250 | | 11/2006 | |
| WO | WO 2006/125511 | | 11/2006 | |
| WO | WO 2007/031860 | | 3/2007 | |
| WO | WO 2007/073503 | | 6/2007 | |
| WO | WO 2007/099423 | | 9/2007 | |
| WO | WO 2008/036967 | | 3/2008 | |
| WO | WO 2008/151211 | | 12/2008 | |
| WO | WO 2010/001220 | | 1/2010 | |
| WO | WO 2012/065953 | | 5/2012 | |
| WO | WO 2012/116415 | | 9/2012 | |
| WO | WO 2014/083033 | | 6/2014 | |
| WO | WO 2014/198849 | | 12/2014 | |
| WO | WO 2018/172423 | | 9/2018 | |
| WO | WO-2018172423 | A1 * | 9/2018 | ........... A61K 31/195 |
| WO | WO 2020/069008 | | 4/2020 | |

OTHER PUBLICATIONS

Xin et al., "*Pseudomonas aeruginosa* biofilm infection," *JILIN Medical Journal* 36(7):1439-1442, 2015 with English Translation.
Cathcart et al., "Novel Inhibitors of the *Pseudomonas aeruginosa* Virulence Factor LasB: a Potential Therapeutic Approach for the Attenuation of Virulence Mechanisms in Pseudomonal Infection," *Antimicrobial Agents and Chemotherapy* 55(6):2670-2678, 2011.
Desroy et al., "Novel H1dE-K Inhibitors Leading to Attenuated Gram Negative Bacterial Virulence," *Journal of Medicinal Chemistry* 56:1418-1430, 2013.
Ding et al., "Synthesis and investigation of novel 6-(1,2,3-triazol-4-yl)-4-aminoquinazolin derivatives possessing hydroxamic acid moiety for cancer therapy," *Bioorganic & Medicinal Chemistry* 25:27-37, 2017.
Ganeshpurkar et al., "Strategies for the Synthesis of Hydroxamic Acids," *Current Organic Synthesis* 15(2):154-165, 2018.
Kany et al., "Binding Mode Characterization and Early in Vivo Evaluation of Fragment-Like Thiols as Inhibitors of the Virulence Factor LasB from *Pseudomonas aeruginosa*," *ACS Infectious Diseases*, 4:988-997, 2018.
Liu et al., "The modified-Mannich reaction: Conversion of arylboronic acids and subsequent coupling with paraformaldehyde and amines toward the one-pot synthesis of Mannich bases and benzoaxazines," *Tetrahedron Letters* 58:1470-1473, 2017.
Malinger et al., "Discovery of Potent, Selective, and Orally Bioavailable Small-Molecule Modulators of the Mediator Complex-Associated Kinases CDK8 and CDK19," *Journal of Medicinal Chemistry* 59:1078-1101, 2016.
Robinson et al., "Inhibitors of MMP-1: An Examination of $P_1{}^1C_\alpha$Gem-Disubstitution in the Succinamide Hydroxamate Series," *Bioorganic & Medicinal Chemistry Letters* 6(14): 1719-1724, 1996.
Seth, "A Comprehensive Review on Recent Advances in Synthesis & Pharmacotherapeutic Potential of Benzothiazoles," *Anti-Inflammatory & Anti-Allergy Agents in Medicinal Chemistry* 14:98-112, 2015.
Takagi et al., "Palladium(0)-catalyzed Synthesis of 2-Alkylbenzothiazoles by a Novel Thiation of 1-Amino-2-iodoarenes with Thioamides," *Chemistry Letters* 116:839-840, 1987.
Valeur et al., "Amide bond formulation: beyond the myth of coupling reagents," *Chem. Soc. Rev.*, 28:606-631, 2009.
Yerdelen et al., "Synthesis of donepezil-based multifunctional agents for the treatment of Alzheimer's disease," *Bioorganic & Medicinal Chemistry Letters* 25:5576-5582, 2015.

* cited by examiner

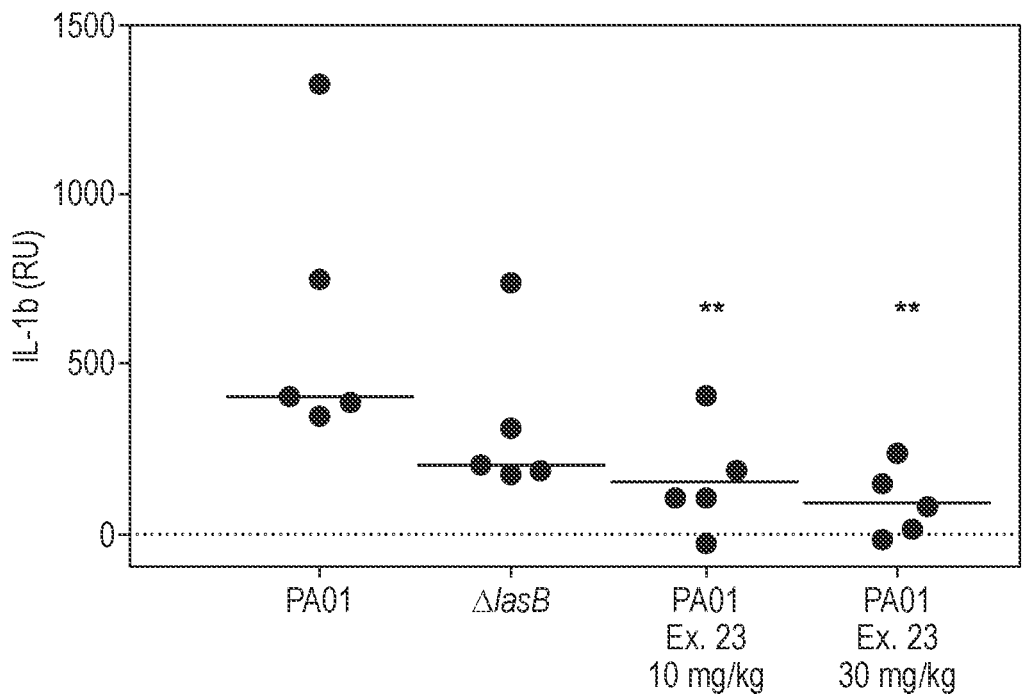
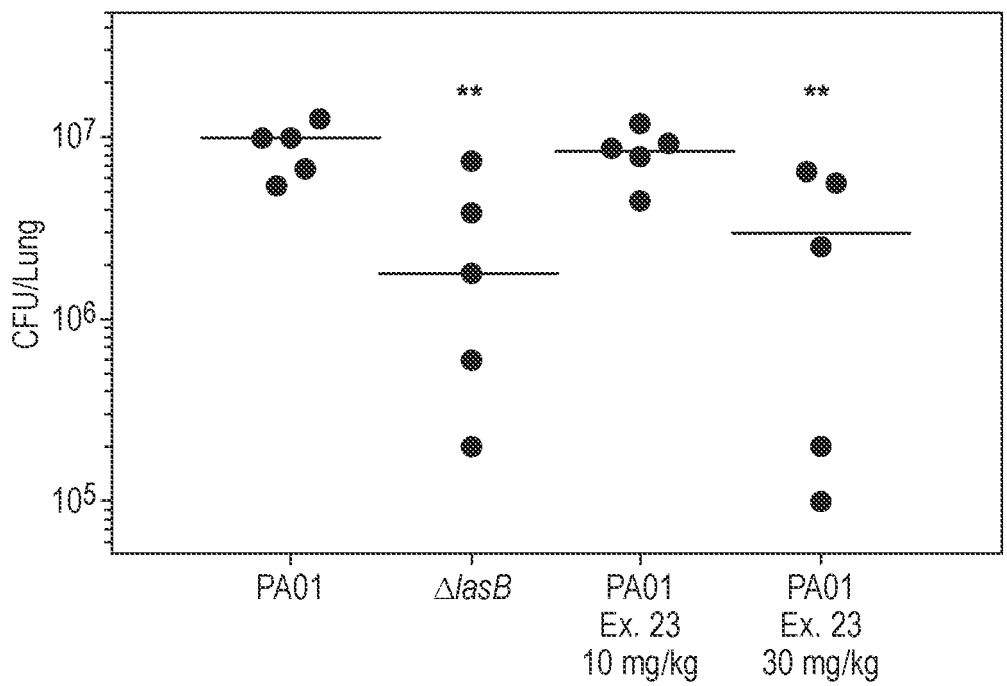

INDANE DERIVATIVES FOR USE IN THE TREATMENT OF BACTERIAL INFECTION

CROSS REFERENCE TO RELATED APPLICATIONS

This is the U.S. National Stage of International Application No. PCT/EP2019/070116, filed on Jul. 25, 2019, which in turn claims the benefit of Application Nos. EP18290106.6 filed on Sep. 25, 2018, EP18290104.1, filed on Sep. 26, 2018, and EP18197365.2 filed on Sep. 27, 2018. These prior applications are incorporated herein in their entireties.

FIELD OF THE INVENTION

The present invention relates to compounds which find use in the prevention or treatment of bacterial infection. The invention also provides such compounds per se and pharmaceutical compositions comprising such compounds.

BACKGROUND

Cystic fibrosis (CF) is a life-threatening disease affecting approximately 70,000 sufferers worldwide. CF is the most common lethal, hereditary disease in Caucasian populations, resulting from mutations in the cystic fibrosis transmembrane conductance regulator (CFTR) gene. The prevalence of CF in Europe is 1 in every 2,000-3,000 live births, and in North America is about 1 in every 3,500 births. In the UK there are approximately 9,800 people with CF.

The organs of individuals with CF typically have significantly thickened secretions. This in turn can lead to a range of pathological problems. For instance, individuals with CF typically have impaired ciliary clearance, and the lungs of such individuals are typically colonized and infected by bacteria from an early age. Such bacteria include *Staphylococcus aureus, Haemophilus influenza, Pseudomonas aeruginosa* and *Burkholderia cepacia. Pseudomonas aeruginosa* (PA) is the most common cause of chronic lung infection in individuals with CF, and chronic infection with PA is found in 9% of pre-school children, 32% of 10-15 year olds and the majority (between 59% and 80%) of adults with CF, leading to progressive lung damage and early death.

As the lung of the individual with CF is colonised by PA, the growth pattern of the bacteria changes and its capacity for survival improves. In chronic infection, PA bacteria on mucosal and epithelial surfaces, or in sputum, form biofilms as well as producing large quantities of alginate (the so-called mucoid phenotype) which reduce the effectiveness of phagocytosis and antibiotic therapy. This leads to chronic colonisation of the lung by PA that is not cleared by conventional antibiotic therapy.

Antibiotics are a broad range of substances exhibiting anti-bacterial activity. A large number of antibiotic compounds are known and have been shown to exhibit antibacterial activity against a wide range of bacteria. However, currently available antibiotics are incapable of controlling some bacterial infections. This is because the target bacteria have acquired antibiotic resistance, for example via horizontal gene transfer or because the target bacteria are found in a state in which the efficacy of antibiotics which would otherwise be highly active is reduced. One such state is a bacterial biofilm.

Bacteria in biofilms are enclosed in a self-produced extracellular biopolymer matrix, which may include polysaccharides, proteins and DNA. Bacteria in biofilms typically exhibit different properties from free-living bacteria of the same species. Such properties typically include increased resistance to antibiotics and detergents and increased lateral gene transfer. For example, bacteria in biofilms typically display up to 1,000-fold higher tolerance to antibiotic challenge than their single cell, planktonic (free-living) counterparts.

This limitation in the efficacy of antibacterial compounds is especially important for individuals who through immunodeficiency or other diseases or conditions cannot adequately combat bacterial infection. Such individuals include those suffering from cystic fibrosis.

CF patients who are colonised with PA show also a more rapid decline in lung function, faster decline in chest radiograph score, poor weight gain, increased hospitalisation rates and an increased need for antibiotic therapy. Median survival is reduced and mortality increased (2.6× risk of death). Most disease-related morbidity and mortality in CF is caused by progressive lung disease as a result of bacterial infection and airway inflammation, primarily associated with the effects of chronic PA lung infection and the persistence of PA biofilms. Despite intensive antibiotic treatment, adaptive mechanisms such as biofilm formation allow PA to resist both immune and antibiotic pressures, leading to recurrent exacerbations and respiratory failure.

Pathogenic bacteria such as PA are not only of importance in the context of CF. For example, the opportunistic pathogen PA can also cause septic shock, particularly in neutropenic patients, and can be responsible for infections of the respiratory tract, the urinary tract, the gastrointestinal network and skin and soft tissues. PA is also a frequent coloniser of medical devices such as catheters, nebulizers, and the like.

Accordingly, there is a clear need for new antibiotic compounds and compositions and adjuvant therapies for treating bacterial infection.

SUMMARY OF THE INVENTION

The inventors have surprisingly found that compounds of Formula (I) are potent inhibitors of the *Pseudomonas aeruginosa*-derived elastase enzyme LasB, which is important in *Pseudomonas aeruginosa* pathogenesis and persistence through biofilm formation.

LasB is implicated in bacterial disease pathology, since secreted LasB degrades many host immune proteins and causes tissue damage. LasB, also known as pseudolysin, is massively secreted into the environment of the producer organism where it is able to proteolytically attack numerous host immune proteins (e.g. immunoglobulins, cytokines, SP-A, antimicrobial peptides (e.g. Trappin 2)) and tissue proteins (e.g. elastin). There are no mammalian homologues of LasB. The ability of LasB to attack host proteins contributes to immune evasion (e.g. avoidance of SP-A mediated phagocytosis, and degradation of immunoglobulin, degradation of antimicrobial peptides (e.g. Trappin 2)) whilst promoting tissue invasion and long term colonization. Inhibition of LasB therefore better equips the host to deal with immune attack.

LasB also has an important internal role within the bacterial cell cleaving nucleoside diphosphate kinase (NDK) to a smaller active form. Active form of NDK leads to increased GTP levels within the cell, increasing production of alginate. Alginate is a polysaccharide which is a major component of the extracellular biofilm matrix and which is required for swarming motility. Those two virulence phenotypes are associated with bacterial persistence in response to immune and antibiotic pressures. LasB activity has also been shown to upregulate rhamnolipid production, which is necessary for biofilm formation/maturation. Accordingly, inhibition of LasB assists impairment of biofilm formation and disruption of the established biofilm. This in turn is believed to better enable antibiotics currently in use to deal effectively with infection.

In addition, LasB directly activates interleukin-1-β (IL-1β). IL-1β is a human protein and key initiator of inflammatory response. This proinflammatory cytokine is a clinical biomarker of inflammation and is upregulated during acute pulmonary exacerbations in CF patients. IL-1β is produced as an inactive form (pro-IL-1β) by host cells in response to pathogen detection and is activated via hydrolytic removal of a peptide moiety by the host caspase-1. Recent research has demonstrated that the *Pseudomonas aeruginosa* (PA)-secreted elastase LasB can also cleave and activate IL-1β. This activation is through a cleavage at an alternative and distinct site from caspase-1. Because LasB directly activates IL-1β by hydrolysis of pro-IL-1β, IL-1β can be thus considered as a marker for PA LasB activity both in vitro and in vivo. The inventors have recognised that the ability of LasB to activate IL-1β leads to applications of inhibitors of LasB in treating inflammation and related conditions.

Accordingly, the invention provides the following aspects:

1. A compound which is an indane according to Formula (I), or a pharmaceutically acceptable salt thereof,

[FORMULA (I)]

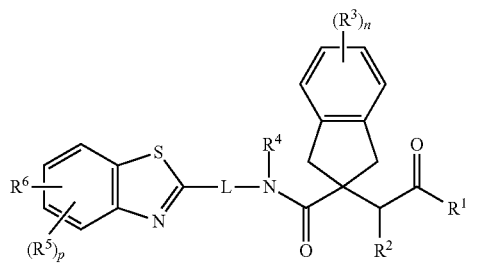

wherein
$R^1$ is selected from:
  NHOH, OH, $OR^{1a}$ and —$OCH_2OC(O)R^{1a}$, wherein $R^{1a}$ is selected from an unsubstituted $C_1$ to $C_4$ alkyl group and phenyl; and
  where the compound of Formula (I) contains a positively charged nitrogen atom, $R^1$ may be $O^-$, such that the compound forms a zwitterion;
$R^2$ is selected from H and unsubstituted $C_1$ to $C_2$ alkyl;
each $R^3$ group is independently selected from halogen, —OH, —$NH_2$, methyl and —$CF_3$;
n is an integer from 0 to 4;
$R^4$ is selected from H and unsubstituted $C_1$ to $C_2$ alkyl;
L is selected from a bond and a $C_1$ to $C_3$ alkylene group which is unsubstituted or is substituted by one group selected from halogen, —OH, —OMe, —$NR^{20}R^{21}$, —$N^+R^{20}R^{21}R^{22}$, and —$CF_3$;
p is 0 or 1;
$R^5$ is selected from —OMe, —OH, halogen, —$NR^{20}R^{21}$, —$N^+R^{20}R^{21}R^{22}$, —$CF_3$, and $R^6$;
each $R^6$ is independently selected from:
  —$R^{6a}R^A$, —O—$R^{6a}R^A$, —$NR^{20}$—$R^{6a}R^A$, —$R^{6b}R^B$, —O—$R^{6b}R^B$, and —$NR^{20}$—$R^{6b}R^B$;

—$R^XR^R$, —O—$R^XR^R$, —O—$R^X$—C(O)—$R^R$, —$R^X$—C(O)—$R^R$, —$NR^{20}$—$R^XR^R$, and —$NR^{20}$—$R^X$—C(O)—$R^R$; and
—CN; —C(O)$NR^{20}R^{21}$; —C(O)$NR^{21}$—$R^XR^B$; —C(O)$NR^{40}R^{41}$; —$SO_2R^{20}$; —$SO_2$—$R^XR^B$; —$SO_2NR^{20}R^{21}$; —$SO_2$—$NR^{20}$—$R^XR^B$; and —$SO_2NR^{40}R^{41}$;

wherein:
  each $R^X$ is independently selected from $R^{6a}$ and $R^{6b}$;
  each $R^{6a}$ is independently selected from $C_1$ to $C_4$ alkylene, $C_2$ to $C_4$ alkenylene and $C_2$ $C_4$ alkynylene; and each $R^{6a}$ is independently unsubstituted or is substituted by one group selected from —OH, halogen; —$NR^{20}R^{21}$; —$N^+R^{20}R^{21}R^{22}$; —$NR^{20}C(NR^{21})NR^{22}R^{23}$; —$NR^{20}C(N^+R^{21}R^{22})NR^{23}R^{24}$; —$NR^{20}C(NR^{21})R^{22}$; —$NR^{20}C(N^+R^{21}R^{22})R^{23}$; —$C(NR^{20})NR^{21}R^{22}$; —$C(N^+R^{20}R^{21})NR^{22}R^{23}$; —$C(NR^{20})R^{21}$; and —$C(N^+R^{20}R^{21})R^{22}$; —$C(O)NR^{20}R^{21}$; —$C(O)N^+R^{20}R^{21}R^{22}$; —$C(O)$—$R^{20}$, and methoxy which is unsubstituted or is substituted by one, two or three halogen substituents;
  each $R^{6b}$ is independently selected from [$C_1$ to $C_3$ alkylene]-$C(R^Z)_2R^b$, [$C_2$ to $C_3$ alkenylene]-$C(R^Z)_2R^b$ and [$C_2$ to $C_3$ alkynylene]-$C(R^Z)_2R^b$; wherein the two $R^Z$ groups are attached together to form, together with the atom to which they are attached, a 5- or 6-membered carbocyclic or heterocyclic group;
  $R^A$ is selected from —$NR^{20}R^{30}$; —$N^+R^{20}R^{21}R^{30}$; —$NR^{20}NR^{21}R^{22}$; —$NR^{20}N^+R^{21}R^{22}R^{23}$; —$N^+R^{20}R^{21}NR^{22}R^{23}$; —$NR^{20}C(NR^{21})NR^{22}R^{30}$; —$NR^{20}C(N^+R^{21}R^{22})NR^{23}R^{30}$; —$C(NR^{20})NR^{21}R^{22}$; and —$C(N^+R^{20}R^{21})NR^{22}R^{23}$;
  $R^B$ is selected from —$NR^{20}R^{21}$; —$N^+R^{20}R^{21}R^{22}$; —$NR^{20}NR^{21}R^{22}$; —$NR^{20}N^+R^{21}R^{22}R^{23}$; —$N^+R^{20}R^{21}NR^{22}R^{23}$; —$NR^{20}C(NR^{21})NR^{22}R^{23}$; —$NR^{20}C(N^+R^{21}R^{22})NR^{23}R^{24}$; —$C(NR^{20})NR^{21}R^{22}$; and —$C(N^+R^{20}R^{21})NR^{22}R^{23}$;
  $R^{40}$ and $R^{41}$, together with the nitrogen atom to which they are attached, form a 4- to 6-membered heterocyclic group, wherein any nitrogen atom in the ring is independently selected from secondary, tertiary and quaternary nitrogen atoms;
  each $R^R$ is independently a 4- to 10-membered heteroaryl or heterocyclic group comprising at least one nitrogen atom, and said nitrogen atom(s) are independently selected from secondary, tertiary and quaternary nitrogen atom(s);
    wherein each $R^R$, and each ring formed by —$NR^{40}R^{41}$, is independently unsubstituted or is substituted with one, two or three groups independently selected from
    i) halogen, —CN;
    ii) oxo, providing that said $R^R$ group is a heterocyclic group;
    iii) —$R^{20}$, —$R^7$—$OR^{20}$; —$R^7$—$NR^{20}R^{21}$; —$R^7$—$N^+R^{20}R^{21}R^{22}$; —$R^7$—$NR^{20}C(NR^{21})NR^{22}R^{23}$; —$R^7$—$NR^{20}C(N^+R^{21}R^{22})NR^{23}R^{24}$; —$R^7$—$NR^{20}C(NR^{21})R^{22}$; —$R^7$—$NR^{20}C(N^+R^{21}R^{22})R^{23}$; —$R^7$—$C(NR^{20})NR^{21}R^{22}$; —$R^7$—$C(N^+R^{20}R^{21})NR^{22}R^{23}$; —$R^7$—$C(NR^{20})R^{21}$; and —$R^7$—$C(N^+R^{20}R^{21})R^{22}$;
  each $R^7$ is independently selected from a bond and unsubstituted $C_1$ to $C_3$ alkylene;
  $R^{20}$, $R^{21}$, $R^{22}$, $R^{23}$ and $R^{24}$ are each independently selected from H and $C_1$ to $C_3$ alkyl which is unsubstituted or is substituted with one —OH or —OMe group or with one, two or three halogen groups;

each $R^{30}$ is independently selected from $C_2$ to $C_3$ alkyl which is unsubstituted or is substituted with one —OH or —OMe group or with one, two or three halogen groups.

2. A compound according to aspect 1, wherein $R^5$ is selected from —OMe and —OH.
3. A compound according to aspect 1, wherein p is 0.
4. A compound according to any one of the preceding aspects wherein $R^1$ is selected from OH and NHOH; or where the compound of Formula (I) contains a positively charged nitrogen atom, $R^1$ may be $O^-$, such that the compound forms a zwitterion.
5. A compound according to any one of the preceding aspects wherein $R^2$ is selected from H and unsubstituted methyl.
6. A compound according to any one of the preceding aspects wherein $R^4$ is H.
7. A compound according to any one of the preceding aspects, wherein n is an integer from 0 to 2
8. A compound according to any one of the preceding aspects, wherein each $R^3$ group is independently selected from halogen and —OH.
9. A compound according to any one of the preceding aspects, wherein L is an unsubstituted $C_1$ alkylene group
10. A compound according to any one of the preceding aspects 1 to 5 wherein each $R^6$ is independently selected from: —$R^{6a}R^A$, —O—$R^{6a}R^A$, —$NR^{20}$—$R^{6a}R^A$, —$R^{6b}R^B$, —O—$R^{6b}R^B$, —$NR^{20}$—$R^{6b}R^B$, —$R^X R^R$, —O—$R^X R^R$, —O—$R^X$—C(O)—$R^R$, and —$R^X$—C(O)—$R^R$,
wherein:
 each $R^X$ is an $R^{6a}$ group;
 each $R^{6a}$ is independently a $C_1$ to $C_4$ alkylene group and each $R^{6a}$ is independently unsubstituted or is substituted by one group selected from —OH, halogen; —$NR^{20}R^{21}$; —$N^+R^{20}R^{21}R^{22}$; and unsubstituted methoxy;
 each $R^{6b}$ is independently a [$C_1$ to $C_3$ alkylene]-$C(R^Z)_2$ $R^b$ group; wherein the two $R^Z$ groups are attached together to form, together with the atom to which they are attached, a 5- or 6-membered carbocyclic or heterocyclic group;
 $R^A$ is selected from —$NR^{20}R^{30}$; —$N^+R^{20}R^{21}R^{30}$; —$NR^{20}NR^{21}R^{22}$; and —$NR^{20}N^+R^{21}R^{22}R^{23}$;
 $R^B$ is selected from —$NR^{20}R^{21}$; —$N^+R^{20}R^{21}R^{22}$; —$NR^{20}NR^{21}R^{22}$; and —$NR^{20}N^+R^{21}R^{22}R^{23}$;
 each $R^R$ is independently a 5- to 6-membered heteroaryl or 4- to 6-membered heterocyclic group comprising at least one nitrogen atom, and said nitrogen atom(s) are independently selected from secondary, tertiary and quaternary nitrogen atom(s); wherein each $R^R$ is independently unsubstituted or is substituted with one, two or three groups independently selected from —$R^{20}$, —$R^7$—$OR^{20}$; —$R^7$—$NR^{20}R^{21}$; and —$R^7$—$N^+R^{20}R^{21}R^{22}$.

11. A compound according to any one of the preceding aspects wherein each $R^6$ is independently selected from: —O—$R^{6a}R^A$, —O—$R^{6b}R^B$, —O—$R^X R^R$, and —O—$R^X$—C(O)—$R^R$,
wherein:
 each $R^X$ is an $R^{6a}$ group;
 each $R^{6a}$ is independently an unsubstituted $C_1$ to $C_4$ alkylene group;
 each $R^{6b}$ is independently a [$C_1$ to $C_3$ alkylene]-$C(R^Z)_2$ $R^b$ group; wherein the two $R^Z$ groups are attached together to form, together with the atom to which they are attached, a 5- or 6-membered heterocyclic group, preferably an oxane group;
 $R^A$ is selected from —$NR^{20}R^{30}$; —$N^+R^{20}R^{21}R^{30}$; —$NR^{20}NR^{21}R^{22}$; and —$NR^{20}N^+R^{21}R^{22}R^{23}$;
 $R^B$ is selected from —$NR^{20}R^{21}$; —$N^+R^{20}R^{21}R^{22}$; —$NR^{20}NR^{21}R^{22}$; and —$NR^{20}N^+R^{21}R^{22}R^{23}$;
 each $R^R$ is independently a 5- to 6-membered heteroaryl or 4- to 6-membered heterocyclic group comprising at least one nitrogen atom, and said nitrogen atom(s) are independently selected from secondary, tertiary and quaternary nitrogen atom(s); wherein each $R^R$ is independently unsubstituted or is substituted with one or two groups independently selected from —$R^{20}$; —$R^7$—$NR^{20}R^{21}$; and —$R^7$—$N^+R^{20}R^{21}R^{22}$.

12. A compound according to any one of aspects 1 to 9 wherein each $R^6$ is independently selected from: —CN; —$C(O)NR^{20}R^{21}$; —$C(O)NR^{21}$—$R^X R^B$; —$C(O)NR^{40}R^{41}$; —$SO_2R^{20}$; —$SO_2NR^{20}R^{21}$; and —$SO_2NR^{40}R^{41}$;
wherein:
 each $R^X$ is a $R^{6a}$ group;
 each $R^{6a}$ is independently a $C_1$ to $C_4$ alkylene group; and each $R^{6a}$ is independently unsubstituted or is substituted by one group selected from —OH, halogen; —$NR^{20}R^{21}$; —$N^+R^{20}R^{21}R^{22}$; and unsubstituted methoxy;
 $R^B$ is selected from —$NR^{20}R^{21}$; —$N^+R^{20}R^{21}R^{22}$; —$NR^{20}NR^{21}R^{22}$; and —$NR^{20}N^+R^{21}R^{22}R^{23}$;
 each $R^{40}$ and $R^{41}$ together with the nitrogen atom to which they are attached, independently form a 4- to 6-membered heterocyclic group, wherein any nitrogen atom in the ring is independently selected from secondary, tertiary and quaternary nitrogen atoms; wherein each ring formed by —$NR^{40}R^{41}$ is independently unsubstituted or is substituted with one, two or three groups independently selected from —$R^{20}$, —$R^7$—$OR^{20}$; —$R^7$—$NR^{20}R^{21}$; and —$R^7$—$N^+R^{20}R^{21}R^{22}$ 13. A compound according to any one of aspects 1 to 9 wherein each $R^6$ is independently selected from: —CN; —$C(O)NR^{20}R^{21}$; —$C(O)NR^{21}$—$R^X R^B$; —$C(O)NR^{40}R^{41}$; —$SO_2R^{20}$; —$SO_2NR^{20}R^{21}$; and —$SO_2NR^4OR^{41}$;
wherein:
 each $R^X$ is a $R^{6a}$ group;
 each $R^{6a}$ is independently an unsubstituted $C_1$ to $C_4$ alkylene group;
 $R^B$ is selected from —$NR^{20}R^{21}$ and —$N^+R^{20}R^{21}R^{22}$;
 each $R^{40}$ and $R^{41}$ together with the nitrogen atom to which they are attached, independently form a 4- to 6-membered heterocyclic group, wherein any nitrogen atom in the ring is independently selected from secondary, tertiary and quaternary nitrogen atoms; wherein each ring formed by $NR^{40}R^{41}$ is independently unsubstituted or is substituted with one or two groups independently selected from —$R^{20}$; —$R^7$—$NR^{20}R^{21}$; and —$R^7$—$N^+R^{20}R^{21}R^{22}$.

14. A compound according to any one of aspects 1 to 13 wherein each $R^R$, or each ring formed by —$NR^4R^{41}$, if present is independently selected from azetidine, morpholine, piperazine, piperidine, pyrrolidine and triazole.

15. A compound according to aspect 1, which compound is selected from
1. 2-[2-[[(4-carbamoyl-1,3-benzothiazol-2-yl)methylcarbamoyl]indan-2-yl]acetic acid 2. 2-[2-[[4-(pyrrolidine-1-carbonyl)-1,3-benzothiazol-2-yl]methylcarbamoyl]indan-2-yl]acetic acid
3. 2-[2-[(4-pyrrolidin-1-ylsulfonyl-1,3-benzothiazol-2-yl)methylcarbamoyl]indan-2-yl]acetic acid
4. 2-[2-[(4-sulfamoyl-1,3-benzothiazol-2-yl)methylcarbamoyl]indan-2-yl]acetic acid
5. 2-[2-[(4-piperazin-1-ylsulfonyl-1,3-benzothiazol-2-yl)methylcarbamoyl]indan-2-yl]acetic acid
6. 2-[2-[[4-(3-aminopyrrolidin-1-yl)sulfonyl-1,3-benzothiazol-2-yl]methylcarbamoyl]indan-2-yl]acetic acid
7. 2-[2-[(4-methylsulfonyl-1,3-benzothiazol-2-yl)methylcarbamoyl]indan-2-yl]acetic acid
8. 2-[2-[[6-methoxy-5-[2-(4-methylpiperazin-1-yl)-2-oxo-ethoxy]-1,3-benzothiazol-2-yl]methylcarbamoyl]indan-2-yl]acetic acid
9. 2-[2-[[6-methoxy-5-(2-morpholinoethoxy)-1,3-benzothiazol-2-yl]methylcarbamoyl]indan-2-yl]acetic acid
10. 2-[5,6-difluoro-2-[[6-methoxy-5-(2-morpholinoethoxy)-1,3-benzothiazol-2-yl]methylcarbamoyl]indan-2-yl]acetic acid
11. 2-[5,6-difluoro-2-[[6-methoxy-5-[(1-methyl-4-piperidyl)methoxy]-1,3-benzothiazol-2-yl]methylcarbamoyl]indan-2-yl]acetic acid
12. 2-[5,6-difluoro-2-[[6-methoxy-5-[2-(4-methylpiperazin-1-yl)-2-oxo-ethoxy]-1,3-benzothiazol-2-yl]methylcarbamoyl]indan-2-yl]acetic acid
13. 2-[5,6-difluoro-2-[[6-methoxy-5-[2-(4-methylmorpholin-4-ium-4-yl)ethoxy]-1,3-benzothiazol-2-yl]methylcarbamoyl]indan-2-yl]acetate
14. 2-[2-[[5-[2-(4,4-dimethylpiperazin-4-ium-1-yl)-2-oxo-ethoxy]-6-methoxy-1,3-benzothiazol-2-yl]methylcarbamoyl]-5,6-difluoro-indan-2-yl]acetate
15. 2-[5,6-difluoro-2-[[6-methoxy-5-[3-(4-methylmorpholin-4-ium-4-yl)propoxy]-1,3-benzothiazol-2-yl]methylcarbamoyl]indan-2-yl]acetate
16. 2-[2-[[6-methoxy-5-[3-(4-methylmorpholin-4-ium-4-yl)propoxy]-1,3-benzothiazol-2-yl]methylcarbamoyl]indan-2-yl]acetate
17. 2-[2-[[5-[(1,1-dimethylpiperidin-1-ium-4-yl)methoxy]-6-methoxy-1,3-benzothiazol-2-yl]methylcarbamoyl]indan-2-yl]acetate
18. 2-[2-[[5-[3-[diethyl(methyl)ammonio]propoxy]-6-methoxy-1,3-benzothiazol-2-yl]methylcarbamoyl]indan-2-yl]acetate
19. 2-[5,6-difluoro-2-[[6-methoxy-5-[3-(1-methylpyrrolidin-1-ium-1-yl)propoxy]-1,3-benzothiazol-2-yl]methylcarbamoyl]indan-2-yl]acetate
20. 2-[2-[[5-[3-[2-hydroxyethyl(dimethyl)ammonio]propoxy]-6-methoxy-1,3-benzothiazol-2-yl]methylcarbamoyl]indan-2-yl]acetate
21. 2-[5,6-difluoro-2-[[5-[3-[2-hydroxyethyl(dimethyl)ammonio]propoxy]-6-methoxy-1,3-benzothiazol-2-yl]methylcarbamoyl]indan-2-yl]acetate
22. 2-[2-[[5-[3-[bis(2-hydroxyethyl)-methyl-ammonio]propoxy]-6-methoxy-1,3-benzothiazol-2-yl]methylcarbamoyl]indan-2-yl]acetate
23. 2-[2-[[5-[3-[bis(2-hydroxyethyl)-methyl-ammonio]propoxy]-6-methoxy-1,3-benzothiazol-2-yl]methylcarbamoyl]-5,6-difluoro-indan-2-yl]acetate
24. 2-[2-[[5-[2-(4-methylpiperazin-1-yl)-2-oxo-ethoxy]-1,3-benzothiazol-2-yl]methylcarbamoyl]indan-2-yl]acetic acid
25. 2-[2-[[5-[2-(4-methylpiperazin-1-yl)ethoxy]-1,3-benzothiazol-2-yl]methylcarbamoyl]indan-2-yl]acetic acid
26. 2-[2-[[6-[3-(dimethylamino)azetidine-1-carbonyl]-1,3-benzothiazol-2-yl]methylcarbamoyl]indan-2-yl]acetic acid
27. 2-[2-[[5-(4-methylpiperazine-1-carbonyl)-1,3-benzothiazol-2-yl]methylcarbamoyl]indan-2-yl]acetic acid
28. 2-[2-[[5-[2-(dimethylamino)ethylcarbamoyl]-1,3-benzothiazol-2-yl]methylcarbamoyl]indan-2-yl]acetic acid
29. 2-[2-[[6-(4-methylpiperazine-1-carbonyl)-1,3-benzothiazol-2-yl]methylcarbamoyl]indan-2-yl]acetic acid
30. 2-[2-[[6-[2-(dimethylamino)ethylcarbamoyl]-1,3-benzothiazol-2-yl]methylcarbamoyl]indan-2-yl]acetic acid
31. 2-[2-[[5-[4-[3-(dimethylamino)propyl]piperazine-1-carbonyl]-1,3-benzothiazol-2-yl]methylcarbamoyl]indan-2-yl]acetic acid
32. 2-[2-[[5-[3-(dimethylamino)azetidine-1-carbonyl]-1,3-benzothiazol-2-yl]methylcarbamoyl]indan-2-yl]acetic acid
33. 2-[2-[[6-methoxy-5-(4-methylpiperazine-1-carbonyl)-1,3-benzothiazol-2-yl]methylcarbamoyl]indan-2-yl]acetic acid
34. 2-[5,6-difluoro-2-[[6-methoxy-5-(4-methylpiperazine-1-carbonyl)-1,3-benzothiazol-2-yl]methylcarbamoyl]indan-2-yl]acetic acid
35. 2-[2-[[5-(4,4-dimethylpiperazin-4-ium-1-carbonyl)-6-methoxy-1,3-benzothiazol-2-yl]methylcarbamoyl]-5,6-difluoro-indan-2-yl]acetate
36. 2-[2-[[5-[3-(dimethylamino)azetidine-1-carbonyl]-6-methoxy-1,3-benzothiazol-2-yl]methylcarbamoyl]indan-2-yl]acetic acid
37. 2-[2-[[5-[3-(dimethylamino)azetidine-1-carbonyl]-6-methoxy-1,3-benzothiazol-2-yl]methylcarbamoyl]-5,6-difluoro-indan-2-yl]acetic acid
38. 2-[2-[[5-[4-(dimethylamino)piperidine-1-carbonyl]-6-methoxy-1,3-benzothiazol-2-yl]methylcarbamoyl]indan-2-yl]acetic acid
39. 2-[2-[[6-methoxy-5-[4-(trimethylammonio)piperidine-1-carbonyl]-1,3-benzothiazol-2-yl]methylcarbamoyl]indan-2-yl]acetate
40. 2-[2-[[5-[2-[(dimethylamino)methyl]morpholine-4-carbonyl]-6-methoxy-1,3-benzothiazol-2-yl]methylcarbamoyl]indan-2-yl]acetic acid
41. 2-[2-[[6-methoxy-5-[2-[(trimethylammonio)methyl]morpholine-4-carbonyl]-1,3-benzothiazol-2-yl]methylcarbamoyl]indan-2-yl]acetate
42. 2-[2-[[6-methoxy-5-[3-(trimethylammonio)azetidine-1-carbonyl]-1,3-benzothiazol-2-yl]methylcarbamoyl]indan-2-yl]acetate
43. 2-[5,6-difluoro-2-[[6-methoxy-5-[3-(trimethylammonio)azetidine-1-carbonyl]-1,3-benzothiazol-2-yl]methylcarbamoyl]indan-2-yl]acetate
44. 2-[2-[[5-[(1,1-dimethylpiperidin-1-ium-4-yl)methoxy]-6-methoxy-1,3-benzothiazol-2-yl]methylcarbamoyl]-5,6-difluoro-indan-2-yl]acetate
45. 2-[2-[[6-methoxy-5-(4-methylpiperazin-1-yl)sulfonyl-1,3-benzothiazol-2-yl]methylcarbamoyl]indan-2-yl]acetic acid
46. 2-[2-[[5-[[4-(dimethylamino)-1-piperidyl]sulfonyl]-6-methoxy-1,3-benzothiazol-2-yl]methylcarbamoyl]indan-2-yl]acetic acid
47. 2-[2-[[6-methoxy-5-[[4-(trimethylammonio)-1-piperidyl]sulfonyl]-1,3-benzothiazol-2-yl]methylcarbamoyl]indan-2-yl]acetate
48. 2-[2-[(6-cyano-1,3-benzothiazol-2-yl)methylcarbamoyl]indan-2-yl]acetic acid
49. 2-[2-[(5-cyano-1,3-benzothiazol-2-yl)methylcarbamoyl]indan-2-yl]acetic acid or a pharmaceutically acceptable salt thereof.

16. A pharmaceutical composition comprising (i) a compound according to any one of the preceding aspects and (ii) at least one pharmaceutically acceptable carrier or diluent; and optionally further comprising (iii) an antibiotic agent.

17. A pharmaceutical composition according to aspect 16 wherein the antibiotic agent is selected from tobramycin, neomycin, streptomycin, gentamycin, ceftazidime, ticarcillin, piperacillin, tazobactam, imipenem, meropenem, rifampicin, ciprofloxacin, amikacin, colistin, aztreonam, azithromycin and levofloxacin.
18. A combination of (i) a compound according to any one of aspects 1 to 15 and (ii) an antibiotic agent.
19. A combination according to aspect 18 wherein the antibiotic agent is selected from tobramycin, neomycin, streptomycin, gentamycin, ceftazidime, ticarcillin, piperacillin, tazobactam, imipenem, meropenem, rifampicin, ciprofloxacin, amikacin, colistin, aztreonam, azithromycin and levofloxacin.
20. A compound according to any one of aspects 1 to 15; a composition according to aspect 16 or 17 or a combination according to aspect 18 or 19 for use in medicine.
21. A compound according to any one of aspects 1 to 15; a composition according to aspect 16 or 17 or a combination according to aspect 18 or 19 for use in treating or preventing bacterial infection in a subject.
22. A compound for use, composition for use or combination for use according to aspect 21 wherein the bacterial infection is caused by *Bacillus, Pseudomonas, Staphylococcus, Streptococcus, Listeria, Burkholderia* or *Escherichia*.
23. A compound for use, composition for use or combination for use according to aspect 22 wherein the bacterial infection is caused by *Pseudomonas aeruginosa*.
24. A compound for use, composition for use or combination for use according to any one of aspects 21 to 23 wherein the compound for use, composition for use or combination for use is for use in the treatment or prevention of pneumonia
25. A compound according to any one of aspects 1 to 15; a composition according to aspect 16 or 17 or a combination according to aspect 18 or 19 for use in treating or preventing inflammation in a subject.
26. A compound for use, composition for use or combination for use according to aspect 25 which is for use in the treatment or prevention of respiratory tract inflammation in a subject.
27. A compound for use, composition for use or combination for use according to aspect 25 or aspect 26 wherein the inflammation is caused by a bacterial infection.
28. A compound for use, composition for use or combination for use according to any one of aspects 21 to 27 wherein the subject suffers from cystic fibrosis.
29. A compound for use, composition for use or combination for use according to any one of aspects 21 to 28 wherein the subject suffers from chronic obstructive pulmonary disease (COPD), bronchiectasis, and/or ventilator-associated pneumonia (VAP).

BRIEF DESCRIPTION OF THE FIGURES

FIG. 2 shows quantification of active IL-1β in the lung following infection by wild-type and ΔlasB mutant PAO1, with and without treatment with compounds of the invention in murine lungs at 24 hours post infection. Results are discussed in Example 52.

Figure 1:
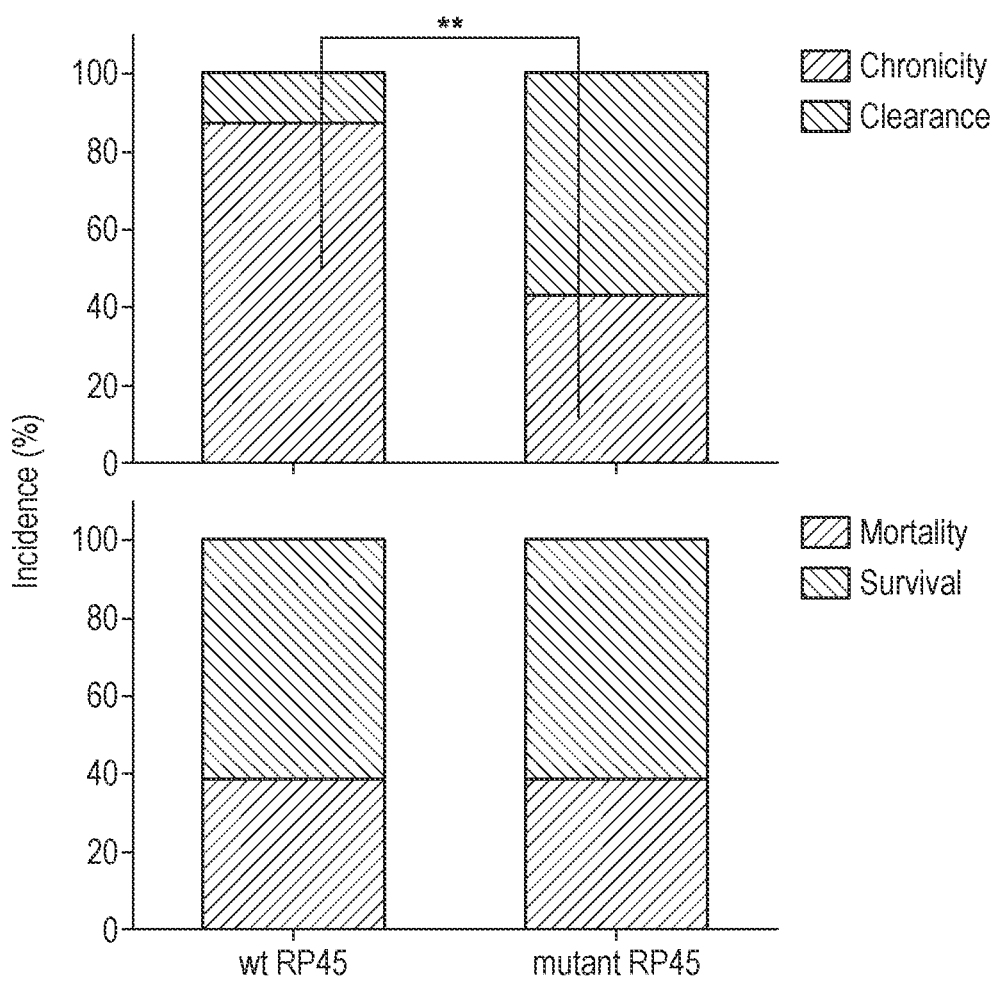
FIG. 1 shows incidences of mortality vs survival and chronic colonization vs bacterial clearance in a mouse model of lung infection, 7 days post-infection with wt and ΔlasB mutant PA strains. Results are discussed in Example 50. ** $p<0.01$.

$p<0.001$, ** $p<0.0001$.

RU=relative light units, proportional to the levels of IL-1β in this experiment.

FIG. 3 shows total colony forming units of wild-type and ΔlasB mutant PAO1, with and without treatment with compounds of the invention in murine lungs at 24 hours post infection. Results are discussed in Example 52.

$p<0.01$, * $p<0.001$

DETAILED DESCRIPTION OF THE INVENTION

Definitions

As used herein, a $C_1$ to $C_4$ alkyl group is a linear or branched alkyl group containing from 1 to 4 carbon atoms. A $C_1$ to $C_4$ alkyl group is often a $C_1$ to $C_3$ alkyl group. Examples of $C_1$ to $C_4$ alkyl groups include methyl, ethyl, n-propyl, iso-propyl, n-butyl, sec-butyl, and tert-butyl. A $C_1$ to $C_3$ alkyl group is typically a $C_1$ to $C_2$ alkyl group. A $C_1$ to $C_2$ alkyl group is methyl or ethyl, typically methyl. For the avoidance of doubt, where two alkyl groups are present, the alkyl groups may be the same or different.

As used herein, an alkoxy group is typically a said alkyl group attached to an oxygen atom. Thus, a $C_2$ to $C_4$ alkoxy group is a $C_2$ to $C_4$ alkyl group attached to an oxygen atom. A $C_1$ to $C_3$ alkoxy group is a $C_1$ to $C_3$ alkyl group attached to an oxygen atom. Examples of $C_2$ to $C_4$ alkoxy groups include ethoxy, n-propyoxy, iso-propoxy, n-butoxy, sec-butoxy, and tert-butoxy. Examples of $C_1$ to $C_3$ alkoxy groups include methoxy, ethoxy n-propyoxy and iso-propoxy. Typically, a $C_1$ to $C_3$ alkoxy group is a $C_1$ to $C_2$ alkoxy group such as a methoxy or ethoxy group. For the avoidance of doubt, where two alkoxy groups are present, the alkoxy groups may be the same or different.

As used herein, a $C_2$ to $C_4$ alkenyl group is a linear or branched alkenyl group containing from 2 to 4 carbon atoms and having one or more, e.g. one or two, typically one double bonds. Typically a $C_2$ to $C_4$ alkenyl group is a $C_2$ to $C_3$ alkenyl group. Examples of $C_2$ to $C_4$ alkenyl groups include ethenyl, propenyl and butenyl. For the avoidance of doubt, where two alkenyl groups are present, the alkenyl groups may be the same or different.

As used herein, a $C_2$ to $C_4$ alkynyl group is a linear or branched alkynyl group containing from 2 to 4 carbon atoms and having one or more, e.g. one or two, typically one triple bonds. Typically a $C_2$ to $C_4$ alkynyl group is a $C_2$ to $C_3$ alkynyl group. Examples of $C_2$ to $C_4$ alkynyl groups include ethynyl, propynyl and butynyl. For the avoidance of doubt, where two alkynyl groups are present, the alkynyl groups may be the same or different.

Unless otherwise stated, an alkyl, alkoxy, alkenyl or alkynyl group as defined herein may be unsubstituted or substituted as provided herein. The substituents on a substituted alkyl, alkenyl, alkynyl or alkoxy group are typically themselves unsubstituted. Where more than one substituent is present, these may be the same or different.

As used herein, a halogen is typically chlorine, fluorine, bromine or iodine and is preferably chlorine, bromine or fluorine, especially chorine or fluorine.

A 4- to 10-membered carbocyclic group is a cyclic hydrocarbon containing from 4 to 10 carbon atoms. A carbocyclic group may be saturated or partially unsaturated, but is typically saturated. A 4- to 10-membered carbocyclic group may be a fused bicyclic group or a spiro bicyclic group, as defined herein. A 4- to 10-membered carbocyclic group may be a saturated 4- to 6-membered, preferably 5- or 6-membered carbocyclic group. Examples of 4- to 6-membered saturated carbocyclic groups include cyclobutyl, cyclopentyl and cyclohexyl groups.

A 4- to 10-membered heterocyclic group is a cyclic group containing from 4 to 10 atoms selected from C, O, N and S in the ring, including at least one heteroatom, and typically one or two heteroatoms. The heteroatom or heteroatoms are typically selected from O, N, and S, most typically from O and N, especially N. A heterocyclic group may be saturated or partially unsaturated, but is typically saturated. A 4- to 10-membered heterocyclic group may be a fused bicyclic group or a spiro bicyclic group, as defined herein. A 4- to 10-membered heterocyclic group may be a saturated 4- to 6-membered, preferably 5- or 6-membered heterocyclic group. References herein to heterocyclic group(s) include quaternised derivatives thereof, as defined herein. Preferred nitrogen-containing heterocyclic groups include azetidine, morpholine, 1,4-oxazepane, octahydropyrrolo[3,4-c]pyrrole, piperazine, piperidine, and pyrrolidine, including quaternised derivatives thereof, as defined herein.

As used herein, a $C_6$ to $C_{10}$ aryl group is a substituted or unsubstituted, monocyclic or fused polycyclic aromatic group containing from 6 to 10 carbon atoms in the ring portion. Examples include monocyclic groups such as phenyl and fused bicyclic groups such as naphthyl and indenyl. Phenyl (benzene) is preferred.

As used herein, a 5- to 10-membered heteroaryl group is a substituted or unsubstituted monocyclic or fused polycyclic aromatic group containing from 5 to 10 atoms in the ring portion, including at least one heteroatom, for example 1, 2 or 3 heteroatoms, typically selected from O, S and N. A heteroaryl group is typically a 5- or 6-membered heteroaryl group or a 9- or 10-membered heteroaryl group. Preferably, the heteroaryl group comprises 1, 2 or 3, preferably 1 or 2 nitrogen atoms. References herein to heteroaryl group(s) include quaternised derivatives thereof, as defined herein. Preferred nitrogen-containing heteroaryl groups include imidazole, pyridine, pyrimidine and pyrazine, including quaternised derivatives thereof, as defined herein.

As used herein, a fused bicyclic group is a group comprising two cyclic moieties sharing a common bond between two atoms. A spiro bicyclic group is a group comprising two cyclic moieties sharing a common atom.

A carbocyclic, heterocyclic, aryl or heteroaryl group may be unsubstituted or substituted as described herein. The substituents on a substituted carbocyclic, heterocyclic, aryl or heteroaryl group are typically themselves unsubstituted, unless otherwise stated.

A number of the compounds described herein comprise heterocyclic or heteroaryl groups comprising at least one nitrogen atom. In such compounds, said nitrogen atom(s) are independently selected from secondary, tertiary and quaternary nitrogen atom(s). A quaternary nitrogen atom is present when the compound comprises a quaternised derivative of one or more monocyclic groups or fused bicyclic groups. As used herein, a quaternised derivative of a moiety such as a cyclic moiety is formed by bonding an additional alkyl group to a nitrogen atom in the moiety such that the valency of the said nitrogen atom increases from 3 to 4 and the nitrogen atom is positively charged.

As used herein, a pharmaceutically acceptable salt is a salt with a pharmaceutically acceptable acid or base. Pharmaceutically acceptable acids include both inorganic acids such as hydrochloric, sulphuric, phosphoric, diphosphoric, hydrobromic or nitric acid and organic acids such as oxalic, citric, fumaric, maleic, malic, ascorbic, succinic, tartaric, palmitic, benzoic, acetic, triphenylacetic, methanesulphonic, ethanesulphonic, 1-hydroxy-2-naphthenoic, isethionic, benzenesulphonic or p-toluenesulphonic acid. Pharmaceutically acceptable bases include alkali metal (e.g. sodium or potassium), alkali earth metal (e.g. calcium or magnesium) and zinc bases, for example hydroxides, carbonates, and bicarbonates, and organic bases such as alkyl amines, aralkyl (i.e. aryl-substituted alkyl; e.g. benzyl) amines and heterocyclic amines.

Where the compound of Formula (I) contains a positively charged nitrogen atom, the compound may exist as a zwitterion, where $R^1$ is $O^-$, thus leaving a $COO^-$ group. Such compounds may also be provided in the form of a pharmaceutically acceptable salt. Suitable salts include those formed with pharmaceutically acceptable acids, which provide a proton to the $COO^-$ group, and a counter-ion to balance the positive charge on the quaternary nitrogen atom. Suitable pharmaceutically acceptable acids include hydrochloric acid, sulphonic acids including methanesulphonic acid and toluene sulphonic acid, ascorbic acid and citric acid. Hydrochloric acid and sulphonic acids are preferred, in particular hydrochloric acid. Alternatively, zwitterions can be combined with pharmaceutically acceptable bases as mentioned above, for example, alkali metal (e.g. sodium or potassium) and alkali earth metal (e.g. calcium or magnesium) hydroxides.

In Formula (I), the stereochemistry is not limited. In particular, compounds of Formula (I) containing one or more stereocentre (e.g. one or more chiral centre) may be used in enantiomerically or diastereoisomerically pure form, or in the form of a mixture of isomers. Further, for the avoidance of doubt, the compounds of the invention may be used in any tautomeric form. Typically, the agent or substance described herein contains at least 50%, preferably at least 60, 75%, 90% or 95% of a compound according to Formula (I) which is enantiomerically or diasteriomerically pure. Thus, the compound is preferably substantially optically pure.

For the avoidance of doubt, the terms 'indanyl derivative' and 'indane derivative' may be used interchangeably and unless otherwise indicated refer to compounds of the invention, such as compounds of Formula (I).

Compounds of the Invention

Preferably, in the invention, p is 0. However, in embodiments of the invention when p is 1, $R^5$ is preferably selected from —OMe, —OH, halogen, —$NR^{20}R^{21}$; —$N^+R^{20}R^{21}R^{22}$, and —$CF_3$. More preferably, $R^5$ is selected from —OMe and —OH. Most preferably, $R^5$ is —OMe.

Preferably, in the invention, L is an unsubstituted $C_1$ alkylene group (i.e. a —$CH_2$— group).

Accordingly, in the invention, it is preferred that:
L is an unsubstituted $C_1$ alkylene group;
p is 0; or p is 1 and $R^5$ is —OMe; preferably p is 0.

Preferably, $R^1$ is selected from OH, NHOH and $OR^{1a}$, or where the compound of Formula (I) contains a positively charged nitrogen atom, $R^1$ may be $O^-$, such that the compound forms a zwitterion. $R^{1a}$ is typically an unsubstituted $C_1$ to $C_4$ alkyl group, such as an unsubstituted $C_1$ to $C_2$ alkyl group. More preferably, $R^{1a}$ is methyl or t-butyl.

More preferably, $R^1$ is OH or NHOH, or where the compound of Formula (I) contains a positively charged nitrogen atom, $R^1$ may be $O^-$, such that the compound forms a zwitterion. Still more preferably, $R^1$ is OH, or where the compound of Formula (I) contains a positively charged nitrogen atom, $R^1$ may be $O^-$, such that the compound forms a zwitterion.

Preferably, $R^2$ is selected from H and unsubstituted $C_1$ to $C_2$ alkyl; preferably $R^2$ is selected from H and methyl. More preferably, $R^2$ is H. Preferably, in the invention, $R^4$ is selected from H and methyl. More preferably, $R^4$ is H. Still more preferably, $R^2$ and $R^4$ are independently H or methyl, most preferably they are both H.

Preferably, therefore, in the invention, $R^1$ is selected from OH, NHOH and $OR^{1a}$; or where the compound of Formula (I) contains a positively charged nitrogen atom, $R^1$ may be $O^-$, such that the compound forms a zwitterion; $R^2$ is selected from H and unsubstituted $C_1$ to $C_2$ alkyl; and $R^4$ is H.

Each $R^3$ group is typically independently selected from halogen; and —OH; and —$NH_2$. More preferably, each $R^3$ group is independently selected from halogen (e.g. fluorine or chlorine) and —OH. Yet more preferably each $R^3$ group is halogen (e.g. fluorine or chlorine), most preferably fluorine. Typically, n is an integer from 0 to 2; more preferably n is 0 or 2; most preferably n is 0.

Preferably, where more than one $R^3$ group is present, each $R^3$ is the same.

Preferably, therefore, in the invention:
$R^1$ is OH or NHOH, or where the compound of Formula (I) contains a positively charged nitrogen atom, $R^1$ may be $O^-$, such that the compound forms a zwitterion;
$R^2$ is selected from H and methyl;
each $R^3$ group is independently selected from halogen (e.g. fluorine or chlorine) and —OH;
n is an integer from 0 to 2; and
$R^4$ is selected from H and methyl.

More preferably,
$R^1$ is OH, or where the compound of Formula (I) contains a positively charged nitrogen atom, $R^1$ may be $O^-$, such that the compound forms a zwitterion;
$R^2$ is H;
each $R^3$ group is independently a halogen group (e.g. fluorine or chlorine);
n is 0 or 2; and
$R^4$ is H.

In a first embodiment of the invention, each $R^6$ is preferably independently selected from: —$R^{6a}R^A$, —O—$R^{6a}R^A$, —$NR^{20}$—$R^{6a}R^A$, —$R^{6b}R^B$, —O—$R^{6b}R^B$, —$NR^{20}$—$R^{6b}R^B$, —$R^XR^R$, —O—$R^XR^R$, —O—$R^X$—C(O)—$R^R$, and —$R^X$—C(O)—$R^R$. More preferably, each $R^6$ is independently selected from: —O—$R^{6a}R^A$, —$NR^{20}$—$R^{6a}R^A$, —O—$R^{6b}R^B$, —$NR^{20}$—$R^{6b}R^B$, —O—$R^XR^R$, and —O—$R^X$—C(O)—$R^R$. Most preferably, each $R^6$ is independently selected from: —O—$R^{6a}R^A$, —O—$R^{6b}R^B$, —O—$R^XR^R$, and —O—$R^X$—C(O)—$R^R$.

In this embodiment of the invention, each $R^X$ is preferably an $R^{6a}$ group. Each $R^{6a}$ is preferably independently a $C_1$ to $C_4$ alkylene group and is independently unsubstituted or is substituted by one group selected from —OH, halogen; —$NR^{20}R^{21}$; —$N^+R^{20}R^{21}R^{22}$; and unsubstituted methoxy. Most preferably, each $R^{6a}$ is independently an unsubstituted $C_1$ to $C_4$ alkylene group; preferably an unsubstituted $C_1$ to $C_3$ alkylene group.

In this embodiment of the invention, each $R^{6b}$ is preferably independently a [$C_1$ to $C_3$ alkylene]-$C(R^Z)_2R^b$ group; wherein the two $R^Z$ groups are attached together to form, together with the atom to which they are attached, a 5- or 6-membered carbocyclic or heterocyclic group. More preferably, the two $R^Z$ groups are attached together to form, together with the atom to which they are attached, a 5- or 6-membered heterocyclic group, most preferably a piperidine or an oxane group, preferably an oxane group. The carbocyclic or heterocyclic group formed by the two $R^Z$ groups is preferably unsubstituted or is substituted by one substituted selected from —$CH_3$, —OH and —$OCH_3$. Most preferably the carbocyclic or heterocyclic group formed by the two $R^Z$ groups is unsubstituted.

In this embodiment of the invention, $R^A$ is preferably selected from —$NR^{20}R^{30}$; —$N^+R^{20}R^{21}R^{30}$; —$NR^{20}NR^{21}R^{22}$; and —$NR^{20}N^+R^{21}R^{22}R^{23}$. More preferably, $R^A$ is selected from —$NR^{20}R^{30}$; and —$N^+R^{20}R^{21}R^{30}$. In this embodiment of the invention, $R^B$ is preferably selected from —$NR^{20}R^{21}$; —$N^+R^{20}R^{21}R^{22}$; —$NR^{20}NR^{21}R^{22}$; and —$NR^{20}N^+R^{21}R^{22}R^{23}$. More preferably, $R^B$ is selected from —$NR^{20}R^{21}$; and —$N^+R^{20}R^{21}R^{22}$.

In this embodiment of the invention, each $R^R$ is preferably independently a 5- to 6-membered heteroaryl or 4- to 6-membered heterocyclic group comprising at least one nitrogen atom, and said nitrogen atom(s) are independently selected from secondary, tertiary and quaternary nitrogen atom(s). More preferably, each $R^R$ is independently a 4- to 6-membered heterocyclic group, e.g. a 5- or 6-membered heterocyclic group, and comprises at least one nitrogen atom, and said nitrogen atom(s) are independently selected from secondary, tertiary and quaternary nitrogen atom(s). Most preferably, each $R^R$ is independently selected from azetidine, morpholine, piperazine, piperidine, pyrrolidine and triazole. For avoidance of doubt, the nitrogen atom(s) in said groups may be quaternized as defined herein.

Preferably, each $R^R$ is independently unsubstituted or is substituted with one, two or three groups independently selected from —$R^{20}$, —$R^7$—$OR^{20}$; —$R^7$—$NR^{20}R^{21}$; and —$R^7$—$N^+R^{20}R^{21}R^{22}$. More preferably each $R^R$ is independently unsubstituted or is substituted with one or two groups independently selected from —$R^{20}$; —$R^7$—$NR^{20}R^{21}$; and —$R^7$—$N^+R^{20}R^{21}R^{22}$. Yet more preferably each $R^R$ is independently unsubstituted or is substituted with one or two —$R^{20}$ groups.

Accordingly, therefore, in this embodiment of the invention, each $R^6$ is preferably independently selected from: —$R^{6a}R^A$, —O—$R^{6a}R^A$, —$NR^{20}$—$R^{6a}R^A$, —$R^{6b}R^B$, —O—$R^{6b}R^B$, —$NR^{20}$—$R^{6b}R^B$, —$R^XR^R$, —O—$R^XR^R$, —O—$R^X$—C(O)—$R^R$, and —$R^X$—C(O)—$R^R$, wherein:
each $R^X$ is an $R^{6a}$ group;
each $R^{6a}$ is independently a $C_1$ to $C_4$ alkylene group and each $R^{6a}$ is independently unsubstituted or is substituted by one group selected from —OH, halogen; —$NR^{20}R^{21}$; —$N^+R^{20}R^{21}R^{22}$; and unsubstituted methoxy;
each $R^{6b}$ is independently a [$C_1$ to $C_3$ alkylene]-$C(R^Z)_2R^b$ group; wherein the two $R^Z$ groups are attached together to form, together with the atom to which they are attached, a 5- or 6-membered carbocyclic or heterocyclic group;
$R^A$ is selected from —$NR^{20}R^{30}$; —$N^+R^{20}R^{21}R^{30}$; —$NR^{20}NR^{21}R^{22}$; and —$NR^{20}N^+R^{21}R^{22}R^{23}$;
$R^B$ is selected from —$NR^{20}R^{21}$; —$N^+R^{20}R^{21}R^{22}$; —$NR^{20}NR^{21}R^{22}$; and —$NR^{20}N^+R^{21}R^{22}R^{23}$;
each $R^R$ is independently a 5- to 6-membered heteroaryl or 4- to 6-membered heterocyclic group comprising at least one nitrogen atom, and said nitrogen atom(s) are independently selected from secondary, tertiary and quaternary nitrogen atom(s);
wherein each $R^R$ is independently unsubstituted or is substituted with one, two or three groups independently selected from —$R^{20}$, —$R^7$—$OR^{20}$; —$R^7$—$NR^{20}R^{21}$; and —$R^7$—$N^+R^{20}R^{21}R^{22}$.

More preferably, in this embodiment, each $R^6$ is independently selected from: —O—$R^{6a}R^A$, —O—$R^{6b}R^B$, —O—$R^XR^R$, and —O—$R^X$—C(O)—$R^R$, wherein:
- each $R^X$ is an $R^{6a}$ group;
- each $R^{6a}$ is independently an unsubstituted $C_1$ to $C_4$ alkylene group;
- each $R^{6b}$ is independently a [$C_1$ to $C_3$ alkylene]-C($R^Z$)$_2R^b$ group; wherein the two $R^Z$ groups are attached together to form, together with the atom to which they are attached, a 5- or 6-membered heterocyclic group, preferably an oxane group;
- $R^A$ is selected from —NR$^{20}$R$^{30}$; —N$^+$R$^{20}$R$^{21}$R$^{30}$; —NR$^{20}$NR$^{21}$R$^{22}$; and —NR$^{20}$N$^+$R$^{21}$R$^{22}$R$^{23}$;
- $R^B$ is selected from —NR$^{20}$R$^{21}$; —N$^+$R$^{20}$R$^{21}$R$^{22}$; —NR$^{20}$NR$^{21}$R$^{22}$; and —NR$^{20}$N$^+$R$^{21}$R$^{22}$R$^{23}$;
- each $R^R$ is independently a 5- to 6-membered heteroaryl or 4- to 6-membered heterocyclic group comprising at least one nitrogen atom, and said nitrogen atom(s) are independently selected from secondary, tertiary and quaternary nitrogen atom(s);
  - wherein each $R^R$ is independently unsubstituted or is substituted with one or two groups independently selected from —R$^{20}$; —R$^7$—NR$^{20}$R$^{21}$; and —R$^7$—N$^+$R$^{20}$R$^{21}$R$^{22}$.

In a second embodiment of the invention, each $R^6$ is preferably independently selected from: —CN; —C(O)NR$^{20}$R$^{21}$; —C(O)NR$^{21}$—R$^XR^B$; —C(O)NR$^{40}$R$^{41}$; —SO$_2$R$^{20}$; —SO$_2$NR$^{20}$R$^{21}$; and —SO$_2$NR$^{40}$R$^{41}$. More preferably, each $R^6$ is independently selected from: —C(O)NR$^{20}$R$^{21}$; —C(O)NR$^{21}$—R$^XR^B$; —C(O)NR$^{40}$R$^{41}$; and —SO$_2$NR$^{40}$R$^{41}$. Yet more preferably each $R^6$ is independently selected from —SO$_2$NR$^{40}$R$^{41}$ and —C(O)NR$^{40}$R$^{41}$. Most preferably, each $R^6$ is independently a C(O)NR$^{20}$R$^{21}$ group.

In this embodiment of the invention, each $R^X$ is preferably an $R^{6a}$ group. Each $R^{6a}$ is preferably independently a $C_1$ to $C_4$ alkylene group and is independently unsubstituted or is substituted by one group selected from —OH, halogen; —NR$^{20}$R$^{21}$; —N$^+$R$^{20}$R$^{21}$R$^{22}$; and unsubstituted methoxy. Most preferably, each $R^{6a}$ is independently an unsubstituted $C_1$ to $C_4$ alkylene group; preferably an unsubstituted $C_1$ to $C_3$ alkylene group.

In this embodiment of the invention, $R^B$ is preferably selected from —NR$^{20}$R$^{21}$; —N$^+$R$^{20}$R$^{21}$R$^{22}$; —NR$^{20}$NR$^{21}$R$^{22}$; and —NR$^{20}$N$^+$R$^{21}$R$^{22}$R$^{23}$. More preferably, $R^B$ is selected from —NR$^{20}$R$^{21}$; and —N$^+$R$^{20}$R$^{21}$R$^{22}$.

In this embodiment of the invention, each $R^{40}$ and $R^{41}$ together with the nitrogen atom to which they are attached, preferably independently form a 4- to 6-membered heterocyclic group, e.g. a 4- or 6-membered heterocyclic group, wherein any nitrogen atom in the ring is independently selected from secondary, tertiary and quaternary nitrogen atoms. Most preferably, each ring formed by —NR$^{40}$R$^{41}$, if present is independently selected from azetidine, morpholine, piperazine, piperidine, pyrrolidine and triazole. For avoidance of doubt, the nitrogen atom(s) in said groups may be quaternized as defined herein.

Preferably, each ring formed by —NR$^{40}$R$^{41}$ is independently unsubstituted or is substituted with one, two or three groups independently selected from —R$^{20}$, —R$^7$—OR$^{20}$; —R$^7$—NR$^{20}$R$^{21}$; and —R$^7$—N$^+$R$^{20}$R$^{21}$R$^{22}$. More preferably, each ring formed by NR$^{40}$R$^{41}$ is independently unsubstituted or is substituted with one or two groups independently selected from —R$^{20}$; —R$^7$—NR$^{20}$R$^{21}$; and —R$^7$—N$^+$R$^{20}$R$^{21}$R$^{22}$. Most preferably, each ring formed by NR$^{40}$R$^{41}$ is independently unsubstituted or is substituted with one or two groups independently selected from —R$^{20}$ and —R$^7$—NR$^{20}$R$^{21}$.

Accordingly, therefore, in this embodiment of the invention, each $R^6$ is preferably independently selected from: —CN; —C(O)NR$^{20}$R$^{21}$; —C(O)NR$^{21}$—R$^XR^B$; —C(O)NR$^{40}$R$^{41}$; —SO$_2$R$^{20}$; —SO$_2$NR$^{20}$R$^{21}$; and —SO$_2$NR$^4$OR$^{41}$; wherein:
- each $R^X$ is a $R^{6a}$ group;
- each $R^{6a}$ is independently a $C_1$ to $C_4$ alkylene group; and each $R^{6a}$ is independently unsubstituted or is substituted by one group selected from —OH, halogen; —NR$^{20}$R$^{21}$; —N$^+$R$^{20}$R$^{21}$R$^{22}$; and unsubstituted methoxy;
- $R^B$ is selected from —NR$^{20}$R$^{21}$; —N$^+$R$^{20}$R$^{21}$R$^{22}$; —NR$^{20}$NR$^{21}$R$^{22}$; and —NR$^{20}$N$^+$R$^{21}$R$^{22}$R$^{23}$;
- each $R^{40}$ and $R^{41}$ together with the nitrogen atom to which they are attached, independently form a 4- to 6-membered heterocyclic group, wherein any nitrogen atom in the ring is independently selected from secondary, tertiary and quaternary nitrogen atoms;
  - wherein each ring formed by —NR$^{40}$R$^{41}$ is independently unsubstituted or is substituted with one, two or three groups independently selected from —R$^{20}$, —R$^7$—OR$^{20}$; —R$^7$—NR$^{20}$R$^{21}$; and —R$^7$—N$^+$R$^{20}$R$^{21}$R$^{22}$.

More preferably, in this embodiment, each $R^6$ is independently selected from: —CN; —C(O)NR$^{20}$R$^{21}$; —C(O)NR$^{21}$—R$^XR^B$; —C(O)NR$^{40}$R$^{41}$; —SO$_2$R$^{20}$; —SO$_2$NR$^{20}$R$^{21}$; and —SO$_2$NR$^{40}$R$^{41}$; wherein:
- each $R^X$ is a $R^{6a}$ group;
- each $R^{6a}$ is independently an unsubstituted $C_1$ to $C_4$ alkylene group;
- $R^B$ is selected from —NR$^{20}$R$^{21}$ and —N$^+$R$^{20}$R$^{21}$R$^{22}$;
- each $R^{40}$ and $R^{41}$ together with the nitrogen atom to which they are attached, independently form a 4- to 6-membered heterocyclic group, wherein any nitrogen atom in the ring is independently selected from secondary, tertiary and quaternary nitrogen atoms;
- wherein each ring formed by NR$^{40}$R$^{41}$ is independently unsubstituted or is substituted with one or two groups independently selected from —R$^{20}$; —R$^7$—NR$^{20}$R$^{21}$; and —R$^7$—N$^+$R$^{20}$R$^{21}$R$^{22}$.

In particularly preferred compounds of the invention, therefore:
- $R^1$ is OH or NHOH, or where the compound of Formula (I) contains a positively charged nitrogen atom, $R^1$ may be O$^-$, such that the compound forms a zwitterion;
- $R^2$ is selected from H and methyl;
- each $R^3$ group is independently selected from halogen (e.g. fluorine or chlorine) and —OH;
- n is an integer from 0 to 2;
- $R^4$ is selected from H and methyl;
- L is an unsubstituted $C_1$ alkylene group;
- p is 0; or p is 1 and $R^5$ is —OMe; preferably p is 0;
- each $R^6$ is preferably independently selected from:

A:
—R$^{6a}$R$^A$, —O—R$^{6a}$R$^A$, —NR$^{20}$—R$^{6a}$R$^A$, —R$^{6b}$R$^B$, —O—R$^{6b}$R$^B$, —NR$^{20}$—R$^{6b}$R$^B$, —R$^XR^R$, —O—R$^XR^R$, —O—R$^X$—C(O)—R$^R$, and —R$^X$—C(O)—R$^R$, wherein:
- each $R^X$ is an $R^{6a}$ group;
- each $R^{6a}$ is independently a $C_1$ to $C_4$ alkylene group and each $R^{6a}$ is independently unsubstituted or is substituted by one group selected from —OH, halogen; —NR$^{20}$R$^{21}$; —N$^+$R$^{20}$R$^{21}$R$^{22}$; and unsubstituted methoxy;

each $R^{6b}$ is independently a [$C_1$ to $C_3$ alkylene]-C($R^Z$)$_2R^b$ group; wherein the two $R^Z$ groups are attached together to form, together with the atom to which they are attached, a 5- or 6-membered carbocyclic or heterocyclic group;

$R^A$ is selected from —NR$^{20}$R$^{30}$; —N$^+$R$^{20}$R$^{21}$R$^{30}$; —NR$^{20}$NR$^{21}$R$^{22}$; and —NR$^{20}$N$^+$R$^{21}$R$^{22}$R$^{23}$;

$R^B$ is selected from —NR$^{20}$R$^{21}$; —N$^+$R$^{20}$R$^{21}$R$^{22}$; —NR$^{20}$NR$^{21}$R$^{22}$; and —NR$^{20}$N$^+$R$^{21}$R$^{22}$R$^{23}$;

each $R^R$ is independently a 5- to 6-membered heteroaryl or 4- to 6-membered heterocyclic group comprising at least one nitrogen atom, and said nitrogen atom(s) are independently selected from secondary, tertiary and quaternary nitrogen atom(s);

wherein each $R^R$ is independently unsubstituted or is substituted with one, two or three groups independently selected from —R$^{20}$, —R$^7$—OR$^{20}$; —R$^7$—NR$^{20}$R$^{21}$; and —R$^7$—N$^+$R$^{20}$R$^{21}$R$^{22}$; and B:
—CN; —C(O)NR$^{20}$R$^{21}$; —C(O)NR$^{21}$—R$^X$R$^B$; —C(O)NR$^{40}$R$^{41}$; —SO$_2$R$^{20}$; —SO$_2$NR$^{20}$R$^{21}$; and —SO$_2$NR$^{40}$R$^{41}$; wherein:

each $R^X$ is a $R^{6a}$ group;

each $R^{6a}$ is independently a $C_1$ to $C_4$ alkylene group; and each $R^{6a}$ is independently unsubstituted or is substituted by one group selected from —OH, halogen; —NR$^{20}$R$^{21}$; —N$^+$R$^{20}$R$^{21}$R$^{22}$; and unsubstituted methoxy;

$R^B$ is selected from —NR$^{20}$R$^{21}$; —N$^+$R$^{20}$R$^{21}$R$^{22}$; —NR$^{20}$NR$^{21}$R$^{22}$; and —NR$^{20}$N$^+$R$^{21}$R$^{22}$R$^{23}$;

each $R^{40}$ and $R^{41}$ together with the nitrogen atom to which they are attached, independently form a 4- to 6-membered heterocyclic group, wherein any nitrogen atom in the ring is independently selected from secondary, tertiary and quaternary nitrogen atoms;

wherein each ring formed by —NR$^{40}$R$^{41}$ is independently unsubstituted or is substituted with one, two or three groups independently selected from —R$^{20}$, —R$^7$—OR$^{20}$; —R$^7$—NR$^{20}$R$^{21}$; and —R$^7$—N$^+$R$^{20}$R$^{21}$R$^{22}$ In still more particularly preferred compounds of the invention:

$R^1$ is OH, or where the compound of Formula (I) contains a positively charged nitrogen atom, $R^1$ may be O$^-$, such that the compound forms a zwitterion;

$R^2$ is H;

each $R^3$ group is independently a halogen group (e.g. fluorine or chlorine);

n is 0 or 2;

$R^4$ is H;

L is an unsubstituted $C_1$ alkylene group;

p is 0; or p is 1 and $R^5$ is —OMe; preferably p is 0;

each $R^6$ is preferably independently selected from:

A:
—O—R$^{6a}$R$^A$, —O—R$^{6b}$R$^B$, —O—R$^X$R$^R$, and —O—R$^X$—C(O)—R$^R$, wherein:

each $R^X$ is an $R^{6a}$ group;

each $R^{6a}$ is independently an unsubstituted $C_1$ to $C_4$ alkylene group;

each $R^{6b}$ is independently a [$C_1$ to $C_3$ alkylene]-C($R^Z$)$_2R^b$ group; wherein the two $R^Z$ groups are attached together to form, together with the atom to which they are attached, a 5- or 6-membered heterocyclic group, preferably an oxane group;

$R^A$ is selected from —NR$^{20}$R$^{30}$; —N$^+$R$^{20}$R$^{21}$R$^{30}$; —NR$^{20}$NR$^{21}$R$^{22}$; and —NR$^{20}$N$^+$R$^{21}$R$^{22}$R$^{23}$;

$R^B$ is selected from —NR$^{20}$R$^{21}$; —N$^+$R$^{20}$R$^{21}$R$^{22}$; —NR$^{20}$NR$^{21}$R$^{22}$; and —NR$^{20}$N$^+$R$^{21}$R$^{22}$R$^{23}$;

each $R^R$ is independently a 5- to 6-membered heteroaryl or 4- to 6-membered heterocyclic group comprising at least one nitrogen atom, and said nitrogen atom(s) are independently selected from secondary, tertiary and quaternary nitrogen atom(s);

wherein each $R^R$ is independently unsubstituted or is substituted with one or two groups independently selected from —R$^{20}$; —R$^7$—NR$^{20}$R$^{21}$; and —R$^7$—N$^+$R$^{20}$R$^{21}$R$^{22}$; and B:
—CN; —C(O)NR$^{20}$R$^{21}$; —C(O)NR$^{21}$—R$^X$R$^B$; —C(O)NR$^{40}$R$^{41}$; —SO$_2$R$^{20}$; —SO$_2$NR$^{20}$R$^{21}$; and —SO$_2$NR$^{40}$R$^{41}$; wherein:

each $R^X$ is a $R^{6a}$ group;

each $R^{6a}$ is independently an unsubstituted $C_1$ to $C_4$ alkylene group;

$R^B$ is selected from —NR$^{20}$R$^{21}$ and —N$^+$R$^{20}$R$^{21}$R$^{22}$;

each $R^{40}$ and $R^{41}$ together with the nitrogen atom to which they are attached, independently form a 4- to 6-membered heterocyclic group, wherein any nitrogen atom in the ring is independently selected from secondary, tertiary and quaternary nitrogen atoms;

wherein each ring formed by NR$^{40}$R$^{41}$ is independently unsubstituted or is substituted with one or two groups independently selected from —R$^{20}$; —R$^7$—NR$^{20}$R$^{21}$; and —R$^7$—N$^+$R$^{20}$R$^{21}$R$^{22}$.

Preferably, in the invention, $R^7$ is selected from a bond and unsubstituted $C_1$ alkylene; more preferably $R^7$ is a bond.

Preferably, in the invention, $R^{20}$, $R^{21}$, $R^{22}$, $R^{23}$ and $R^{24}$ are each independently selected from H and $C_1$ to $C_2$ alkyl which is unsubstituted or is substituted with one OMe group. More preferably, $R^{20}$, $R^{21}$, $R^{22}$, $R^{23}$ and $R^{24}$ are each independently selected from H and unsubstituted $C_1$ to $C_2$ alkyl; most preferably $R^{20}$, $R^{21}$, $R^{22}$, $R^{23}$ and $R^{24}$ are each independently selected from H and methyl.

Preferably, in the invention, each $R^{30}$ is independently $C_2$ or $C_3$ alkyl which is unsubstituted or is substituted with one OMe group. More preferably, each $R^{30}$ is independently $C_2$ alkyl which is unsubstituted or is substituted with one OMe group. Most preferably, each $R^{30}$ is independently unsubstituted $C_2$ alkyl.

Preferred compounds of the invention are provided in the Examples.

More preferred compounds of the invention are selected from: 2-[2-[[6-methoxy-5-[2-(4-methylpiperazin-1-yl)-2-oxo-ethoxy]-1,3-benzothiazol-2-yl]methylcarbamoyl]indan-2-yl]acetic acid; 2-[2-[[6-methoxy-5-(2-morpholinoethoxy)-1,3-benzothiazol-2-yl]methylcarbamoyl]indan-2-yl] acetic acid; 2-[5,6-difluoro-2-[[6-methoxy-5-(2-morpholinoethoxy)-1,3-benzothiazol-2-yl]methylcarbamoyl]indan-2-yl]acetic acid; 2-[5,6-difluoro-2-[[6-methoxy-5-[(1-methyl-4-piperidyl)methoxy]-1,3-benzothiazol-2-yl]methylcarbamoyl]indan-2-yl]acetic acid; 2-[5,6-difluoro-2-[[6-methoxy-5-[2-(4-methylpiperazin-1-yl)-2-oxo-ethoxy]-1,3-benzothiazol-2-yl]methylcarbamoyl]indan-2-yl]acetic acid; 2-[5,6-difluoro-2-[[6-methoxy-5-[2-(4-methylmorpholin-4-ium-4-yl)ethoxy]-1,3-benzothiazol-2-yl]methylcarbamoyl]indan-2-yl]acetate; 2-[2-[[5-[2-(4,4-dimethylpiperazin-4-ium-1-yl)-2-oxo-ethoxy]-6-methoxy-1,3-benzothiazol-2-yl]methylcarbamoyl]-5,6-difluoro-indan-2-yl]acetate; 2-[5,6-difluoro-2-[[6-methoxy-5-[3-(4- methylmorpholin-4-ium-4-yl)propoxy]-1,3-benzothiazol-2-yl]methylcarbamoyl]indan-2-yl]acetate; 2-[2-[[6-methoxy-5-[3-(4-methylmorpholin-4-ium-4-yl)propoxy]-1,3-benzothiazol-2-yl]methylcarbamoyl]indan-2-yl]acetate; 2-[2-[[5-[(1,1-dimethylpiperidin-1-ium-4-yl)methoxy]-6-methoxy-1,3-benzothiazol-2-yl]methylcarbamoyl]indan-2-yl]acetate; 2-[2-[[5-[3-[diethyl(methyl)ammonio]propoxy]-6-methoxy-1,3-benzothiazol-2-yl]methylcarbamoyl]indan-2-yl]acetate; 2-[5,6-difluoro-2-[[6-methoxy-5-[3-(1-methylpyrrolidin-1-ium-1-yl)propoxy]-1,3-benzothiazol-2-yl]methylcarbamoyl]indan-2-yl]acetate; 2-[2-[[5-[3-[2-hydroxyethyl(dimethyl)ammonio]propoxy]-6-methoxy-1,3-benzothiazol-2-yl]methylcarbamoyl]indan-2-yl]acetate; 2-[5,6-difluoro-2-[[5-[3-[2-hydroxyethyl(dimethyl)ammonio]propoxy]-6-methoxy-1,3-benzothiazol-2-yl]methylcarbamoyl]indan-2-yl]acetate; 2-[2-[[5-[3-[bis(2-hydroxyethyl)-methyl-ammonio]propoxy]-6-methoxy-1,3-benzothiazol-2-yl]methylcarbamoyl]indan-2-yl]acetate; 2-[2-[[5-[3-[bis(2-hydroxyethyl)-methyl-ammonio]propoxy]-6-methoxy-1,3-benzothiazol-2-yl]methylcarbamoyl]-5,6-difluoro-indan-2-yl]acetate; 2-[2-[[6-methoxy-5-(4-methylpiperazine-1-carbonyl)-1,3-benzothiazol-2-yl]methylcarbamoyl]indan-2-yl]acetic acid; 2-[5,6-difluoro-2-[[6-methoxy-5-(4-methylpiperazine-1-carbonyl)-1,3-benzothiazol-2-yl]methylcarbamoyl]indan-2-yl]acetic acid; 2-[2-[[5-(4,4-dimethylpiperazin-4-ium-1-carbonyl)-6-methoxy-1,3-benzothiazol-2-yl]methylcarbamoyl]-5,6-difluoro-indan-2-yl]acetate; 2-[2-[[5-[3-(dimethylamino)azetidine-1-carbonyl]-6-methoxy-1,3-benzothiazol-2-yl]methylcarbamoyl]indan-2-yl]acetic acid; 2-[2-[[5-[3-(dimethylamino)azetidine-1-carbonyl]-6-methoxy-1,3-benzothiazol-2-yl]methylcarbamoyl]-5,6-difluoro-indan-2-yl]acetic acid; 2-[2-[[5-[4-(dimethylamino)piperidine-1-carbonyl]-6-methoxy-1,3-benzothiazol-2-yl]methylcarbamoyl]indan-2-yl]acetic acid; 2-[2-[[5-[2-[(dimethylamino)methyl]morpholine-4-carbonyl]-6-methoxy-1,3-benzothiazol-2-yl]methylcarbamoyl]indan-2-yl]acetic acid; 2-[2-[[6-methoxy-5-[2-[(trimethylammonio)methyl]morpholine-4-carbonyl]-1,3-benzothiazol-2-yl]methylcarbamoyl]indan-2-yl]acetate; 2-[5,6-difluoro-2-[[6-methoxy-5-[3-(trimethylammonio)azetidine-1-carbonyl]-1,3-benzothiazol-2-yl]methylcarbamoyl]indan-2-yl]acetate; 2-[2-[[5-[(1,1-dimethylpiperidin-1-ium-4-yl)methoxy]-6-methoxy-1,3-benzothiazol-2-yl]methylcarbamoyl]-5,6-difluoro-indan-2-yl]acetate; 2-[2-[[6-methoxy-5-(4-methylpiperazin-1-yl)sulfonyl-1,3-benzothiazol-2-yl]methylcarbamoyl]indan-2-yl]acetate; 2-[2-[[5-[[4-(dimethylamino)-1-piperidyl]sulfonyl]-6-methoxy-1,3-benzothiazol-2-yl]methylcarbamoyl]indan-2-yl]acetic acid; and 2-[2-[[6-methoxy-5-[[4-(trimethylammonio)-1-piperidyl]sulfonyl]-1,3-benzothiazol-2-yl]methylcarbamoyl]indan-2-yl]acetate; or a pharmaceutically acceptable salt thereof.

Yet more preferred compounds of the invention are selected from: 2-[2-[[6-methoxy-5-(2-morpholinoethoxy)-1,3-benzothiazol-2-yl]methylcarbamoyl]indan-2-yl]acetic acid; 2-[5,6-difluoro-2-[[6-methoxy-5-(2-morpholinoethoxy)-1,3-benzothiazol-2-yl]methylcarbamoyl]indan-2-yl]acetic acid; 2-[5,6-difluoro-2-[[6-methoxy-5-[(1-methyl-4-piperidyl)methoxy]-1,3-benzothiazol-2-yl]methylcarbamoyl]indan-2-yl]acetic acid; 2-[2-[[6-methoxy-5-[3-(4-methylmorpholin-4-ium-4-yl)propoxy]-1,3-benzothiazol-2-yl]methylcarbamoyl]indan-2-yl]acetate; 2-[2-[[5-[3-[diethyl(methyl)ammonio]propoxy]-6-methoxy-1,3-benzothiazol-2-yl]methylcarbamoyl]indan-2-yl]acetate; 2-[5,6-difluoro-2-[[6-methoxy-5-[3-(1-methylpyrrolidin-1-ium-1-yl)propoxy]-1,3-benzothiazol-2-yl]methylcarbam-oyl]indan-2-yl]acetate; 2-[2-[[5-[3-[2-hydroxyethyl(dimethyl)ammonio]propoxy]-6-methoxy-1,3-benzothiazol-2-yl]methylcarbamoyl]indan-2-yl]acetate; 2-[5,6-difluoro-2-[[5-[3-[2-hydroxyethyl(dimethyl)ammonio]propoxy]-6-methoxy-1,3-benzothiazol-2-yl]methylcarbamoyl]indan-2-yl]acetate; 2-[2-[[5-[3-[bis(2-hydroxyethyl)-methyl-ammonio]propoxy]-6-methoxy-1,3-benzothiazol-2-yl]methylcarbamoyl]indan-2-yl]acetate; 2-[2-[[5-[3-[bis(2-hydroxyethyl)-methyl-ammonio]propoxy]-6-methoxy-1,3-benzothiazol-2-yl]methylcarbamoyl]-5,6-difluoro-indan-2-yl]acetate; 2-[2-[[6-methoxy-5-(4-methylpiperazine-1-carbonyl)-1,3-benzothiazol-2-yl]methylcarbamoyl]indan-2-yl]acetic acid; 2-[5,6-difluoro-2-[[6-methoxy-5-(4-methylpiperazine-1-carbonyl)-1,3-benzothiazol-2-yl]methylcarbamoyl]indan-2-yl]acetic acid; 2-[2-[[5-[3-(dimethylamino)azetidine-1-carbonyl]-6-methoxy-1,3-benzothiazol-2-yl]methylcarbamoyl]indan-2-yl]acetic acid; 2-[2-[[5-[3-(dimethylamino)azetidine-1-carbonyl]-6-methoxy-1,3-benzothiazol-2-yl]methylcarbamoyl]-5,6-difluoro-indan-2-yl]acetic acid; 2-[2-[[5-[(1,1-dimethylpiperidin-1-ium-4-yl)methoxy]-6-methoxy-1,3-benzothiazol-2-yl]methylcarbamoyl]-5,6-difluoro-indan-2-yl]acetate; or a pharmaceutically acceptable salt thereof.

Most preferred compounds of the invention are selected from: 2-[2-[[6-methoxy-5-(2-morpholinoethoxy)-1,3-benzothiazol-2-yl]methylcarbamoyl]indan-2-yl]acetic acid; 2-[5,6-difluoro-2-[[6-methoxy-5-(2-morpholinoethoxy)-1,3-benzothiazol-2-yl]methylcarbamoyl]indan-2-yl]acetic acid; 2-[5,6-difluoro-2-[[6-methoxy-5-[(1-methyl-4-piperidyl)methoxy]-1,3-benzothiazol-2-yl]methylcarbamoyl]indan-2-yl]acetic acid; 2-[5,6-difluoro-2-[[6-methoxy-5-[3-(1-methylpyrrolidin-1-ium-1-yl)propoxy]-1,3-benzothiazol-2-yl]methylcarbamoyl]indan-2-yl]acetate; 2-[5,6-difluoro-2-[[5-[3-[2-hydroxyethyl(dimethyl)ammonio]propoxy]-6-methoxy-1,3-benzothiazol-2-yl]methylcarbamoyl]indan-2-yl]acetate; 2-[2-[[5-[3-[bis(2-hydroxyethyl)-methyl-ammonio]propoxy]-6-methoxy-1,3-benzothiazol-2-yl]methylcarbamoyl]-5,6-difluoro-indan-2-yl]acetate; 2-[5,6-difluoro-2-[[6-methoxy-5-(4-methylpiperazine-1-carbonyl)-1,3-benzothiazol-2-yl]methylcarbamoyl]indan-2-yl]acetic acid; 2-[2-[[5-[3-(dimethylamino)azetidine-1-carbonyl]-6-methoxy-1,3-benzothiazol-2-yl]methylcarbamoyl]indan-2-yl]acetic acid; 2-[2-[[5-[3-(dimethylamino)azetidine-1-carbonyl]-6-methoxy-1,3-benzothiazol-2-yl]methylcarbamoyl]-5,6-difluoro-indan-2-yl]acetic acid; 2-[2-[[5-[(1,1-dimethylpiperidin-1-ium-4-yl)methoxy]-6-methoxy-1,3-benzothiazol-2-yl]methylcarbamoyl]-5,6-difluoro-indan-2-yl]acetate; or a pharmaceutically acceptable salt thereof.

Synthesis

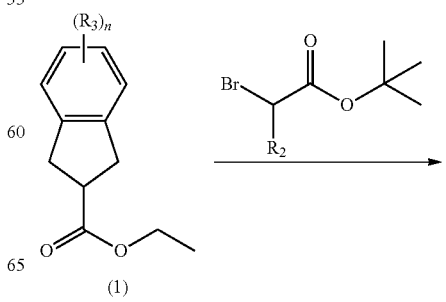

(1)

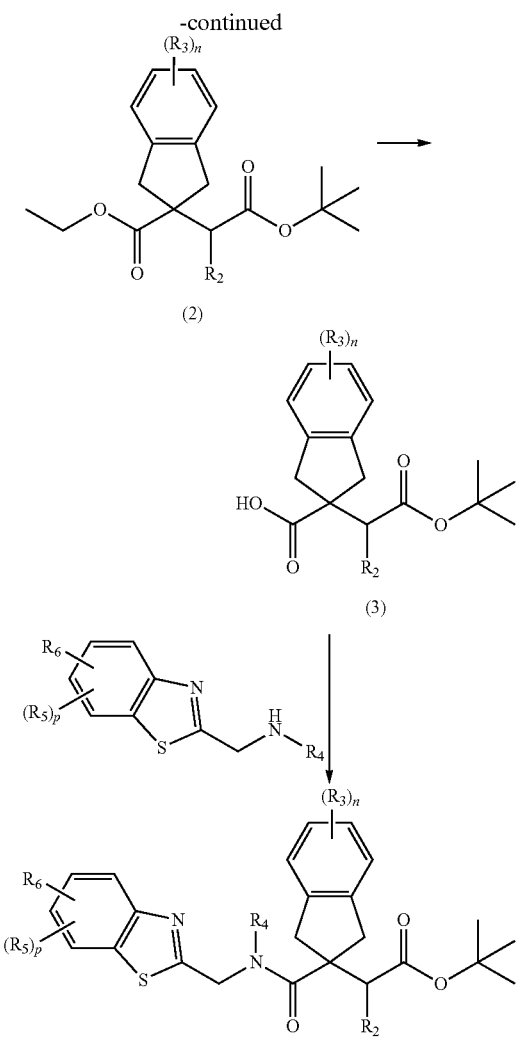

The compounds of the invention can be prepared by any suitable method. For example, as described in more detail below, deprotonation of commercially available ethyl esters (1) with strong base (such as sodium hexamethyldisilazide) then alkylation of the anion with tert-butyl bromoacetates gives diester (2) (Bell, I. M. and Stump, C. A., WO2006/29153; Robinson, R. P. et al, Bioorganic and Medicinal Chemistry Letters, 1996, 1719). Basic hydrolysis of the ethyl ester in the presence of the tert-butyl ester gives (3). Amide formation with a suitable 2-aminomethyl benzothiazole followed by treatment with TFA to remove the tert-butyl ester then affords the desired acids. Examples of suitable protocols for formation of amino-methyl benzothiazoles (4) are provided below. For example, substituents $R_5$ and $R_6$ can be introduced by derivatization of commercially available halo-substituted thiazoles (e.g. by halo displacement) or OH-substituted thiazoles (e.g. by alkylation at the hydroxy position). The acids can be converted to esters ($R^1$=$OR^{1a}$) or other prodrug forms ($R^1$=$OCH_2OC(O)R^{1a}$) by techniques known to the skilled person.

There are numerous ways of accessing hydroxamic acids (for a review see Ganeshpurkar, A., et al, Current Organic Syntheses, 2018, 15, 154-165) but a very reliable procedure is to couple acids with O-(oxan-2-yl)hydroxylamine using peptide coupling conditions to give protected hydroxamates then deprotect with TFA to generate the hydroxamic acids (see for example Ding, C., et al, Bioorg. Med. Chem. Lett, 2017, 25, 27-37).

Compositions and Combinations

The present invention also provides a pharmaceutical composition, the pharmaceutical composition comprising a compound of the invention together with a pharmaceutically acceptable carrier or diluent. Typically, the composition contains up to 85 wt % of a compound of the invention. More typically, it contains up to 50 wt % of a compound of the invention. Preferred pharmaceutical compositions are sterile and pyrogen free. Further, when the pharmaceutical compositions provided by the invention contain a compound of the invention which is optically active, the compound of the invention is typically a substantially pure optical isomer.

The composition of the invention may be provided as a kit comprising instructions to enable the kit to be used in the methods described herein or details regarding which subjects the method may be used for.

As explained above, the compounds of the invention are useful in treating or preventing bacterial infection. In particular, they are useful as inhibitors of LasB, in particular LasB of *Pseudomonas aeruginosa* (PA). The compounds may be used alone or they may be used in combination therapies with antibiotic agents, to enhance the action of the antibiotic agent.

The present invention therefore also provides a combination comprising (i) a compound of the invention as described herein and (ii) an antibiotic agent. The combination may further comprise one or more additional active agents. The compound of the invention and the antibiotic agent may be provided in a single formulation, or they may be separately formulated. Where separately formulated, the two agents may be administered simultaneously or separately. They may be provided in the form of a kit, optionally together with instructions for their administration.

Where formulated together, the two active agents may be provided as a pharmaceutical composition comprising (i) a compound of the invention as described herein and (ii) a further antibacterial compound; and (iii) a pharmaceutically acceptable carrier or diluent.

Preferably, the antibiotic agent is efficacious against *Pseudomonas* infection. Most preferably, the antibiotic is tobramycin, neomycin, streptomycin, gentamycin, ceftazidime, ticarcillin, piperacillin, tazobactam, imipenem, meropenem, rifampicin, ciprofloxacin, amikacin, colistin, aztreonam, azithromycin or levofloxacin. More preferably, the antibiotic is tobramycin, neomycin, streptomycin, gentamycin, ceftazidime, ticarcillin, piperacillin, tazobactam, imipenem, meropenem, rifampicin, ciprofloxacin, amikacin, colistin, aztreonam or levofloxacin.

The compound or combination of the invention may be administered in a variety of dosage forms. Thus, they can be administered orally, for example as tablets, troches, lozenges, aqueous or oily suspensions, dispersible powders or granules. They may also be administered parenterally, whether subcutaneously, intravenously, intramuscularly, intrasternally, transdermally or by infusion techniques. The compound or combination may also be administered as a suppository. Preferably, the compound or combination may be administered via inhaled (aerosolised) or intravenous administration, most preferably by inhaled (aerosolised) administration.

The compound or combination of the invention is typically formulated for administration with a pharmaceutically acceptable carrier or diluent. For example, solid oral forms may contain, together with the active compound, diluents, e.g. lactose, dextrose, saccharose, cellulose, corn starch or potato starch; lubricants, e.g. silica, talc, stearic acid, magnesium or calcium stearate, and/or polyethylene glycols; binding agents; e.g. starches, arabic gums, gelatin, methylcellulose, carboxymethylcellulose or polyvinyl pyrrolidone; disaggregating agents, e.g. starch, alginic acid, alginates or sodium starch glycolate; effervescing mixtures; dyestuffs; sweeteners; wetting agents, such as lecithin, polysorbates, laurylsulphates; and, in general, non toxic and pharmacologically inactive substances used in pharmaceutical formulations. Such pharmaceutical preparations may be manufactured in known manner, for example, by means of mixing, granulating, tableting, sugar coating, or film coating processes.

The compound or combination of the invention may be formulated for inhaled (aerosolised) administration as a solution or suspension. The compound or combination of the invention may be administered by a metered dose inhaler (MDI) or a nebulizer such as an electronic or jet nebulizer. Alternatively, the compound or combination of the invention may be formulated for inhaled administration as a powdered drug, such formulations may be administered from a dry powder inhaler (DPI). When formulated for inhaled administration, the compound or combination of the invention may be delivered in the form of particles which have a mass median aerodynamic diameter (MMAD) of from 1 to 100 μm, preferably from 1 to 50 μm, more preferably from 1 to 20 μm such as from 3 to 10 μm, e.g. from 4 to 6 μm. When the compound or combination of the invention is delivered as a nebulized aerosol, the reference to particle diameters defines the MMAD of the droplets of the aerosol. The MMAD can be measured by any suitable technique such as laser diffraction.

Liquid dispersions for oral administration may be syrups, emulsions and suspensions. The syrups may contain as carriers, for example, saccharose or saccharose with glycerine and/or mannitol and/or sorbitol.

Suspensions and emulsions may contain as carrier, for example a natural gum, agar, sodium alginate, pectin, methylcellulose, carboxymethylcellulose, or polyvinyl alcohol. The suspension or solutions for intramuscular injections or inhalation may contain, together with the active compound, a pharmaceutically acceptable carrier, e.g. sterile water, olive oil, ethyl oleate, glycols, e.g. propylene glycol, and if desired, a suitable amount of lidocaine hydrochloride.

Solutions for inhalation, injection or infusion may contain as carrier, for example, sterile water or preferably they may be in the form of sterile, aqueous, isotonic saline solutions. Pharmaceutical compositions suitable for delivery by needleless injection, for example, transdermally, may also be used.

Therapeutic Efficacy

The compounds, compositions and combinations of the present invention are therapeutically useful. The present invention therefore provides compounds, compositions and combinations as described herein, for use in medicine. The present invention provides compounds as described herein, for use in treating the human or animal body. For the avoidance of doubt, the agent may comprise a compound of the invention in the form of a solvate.

The compounds, compositions and combinations of the invention are useful in treating or preventing bacterial infection. The present invention therefore provides a compound, combination or composition as described herein for use in a method of treating or preventing bacterial infection in a subject in need thereof. Also provided is a method for treating or preventing bacterial infection in a subject in need thereof, which method comprises administering to said subject an effective amount of a compound, combination or composition as described herein. Further provided is the use of a compound, combination or composition as described herein in the manufacture of a medicament for use in treating or preventing bacterial infection in a subject.

The compounds described herein are useful as inhibitors of LasB, in particular LasB of *Pseudomonas aeruginosa* (PA). The inhibition of LasB in the bacteria prevents LasB secreted by bacteria from hydrolysing host tissue and host immune-response proteins, thereby supporting the subject in its natural response to bacterial infection and inflammation. The compounds described herein are therefore useful as standalone adjuncts in antibacterial therapy, for example in chemotherapy regimes. Further, the compounds are useful in inhibiting biofilm formation, and/or in disrupting a biofilm. This activity in preventing biofilm formation or disrupting established biofilms facilitates antibiotic agents in eradication of bacterial infection. It also facilitates the host's own immune system in attacking the bacterial infection. The compounds may therefore be used as stand alone antibacterial agents.

Alternatively, the compounds described herein may be used in combination with antibiotic agents to enhance the action of the antibiotic agent. Therefore, further provided is a compound of the invention as described herein for use in a method of treating or preventing bacterial infection by co-administration with an antibiotic agent. Also provided is a method for treating or preventing bacterial infection in a subject in need thereof, which method comprises co-administering to said subject an effective amount of a compound as described herein and an antibiotic agent. Also provided is the use of a compound as described herein in the manufacture of a medicament for use in treating or preventing bacterial infection by co-administration with an antibiotic agent.

In one aspect, the subject is a mammal, in particular a human. However, it may be non-human. Preferred non-human animals include, but are not limited to, primates, such as marmosets or monkeys, commercially farmed animals, such as horses, cows, sheep or pigs, and pets, such as dogs, cats, mice, rats, guinea pigs, ferrets, gerbils or hamsters. The subject can be any animal that is capable of being infected by a bacterium.

The compounds, compositions and combinations described herein are useful in the treatment of bacterial infection which occurs after a relapse following an antibiotic treatment. The compounds and combinations can therefore be used in the treatment of a patient who has previously received antibiotic treatment for the (same episode of) bacterial infection.

The bacterium causing the infection may be any bacterium expressing LasB or an analogue thereof. Typically the bacterium causing the infection expresses LasB. The bacterium may, for instance, be any bacterium that can form a biofilm. The bacterium may be Gram-positive or Gram-negative. In a preferred instance the bacterium is Gram-negative. The bacterium may in particular be a pathogenic bacterium.

The bacterial infection may be caused by *Bacillus, Pseudomonas, Staphylococcus, Streptococcus, Listeria, Escherichia* or *Burkholderia*. For example, the bacterium may be one selected from *Staphylococcus aureus, Haemophilus influenza, Pseudomonas aeruginosa* and *Burkholderia cepacia*.

In one preferred instance, the bacterium may be one selected from a bacterium of the family Pseudomonadaceae.

For example, the bacterium may be selected from one of the following genera: *Pseudomonas, Azomonas, Azomonotrichon, Azorhizophilus, Azotobacter, Cellvibrio, Mesophilobacter, Rhizobacter, Rugamonas* and *Serpens*. Preferably the bacterium is a *Pseudomonas*, particularly where the condition to be treated is pneumonia. The bacterium may be an opportunistic pathogen. The bacterium may be selected from *Pseudomonas aeruginosa, Pseudomonas oryzihabitans*, and *Pseudomonas plecoglossicida*, and most preferably, the bacterium is *Pseudomonas aeruginosa* (PA).

The compound, composition or combination of the invention may be used to treat or prevent infections and conditions caused by any one or a combination of the above-mentioned bacteria. In particular, the compound or combination of the invention may be used in the treatment or prevention of pneumonia. The compound or combination may also be used in the treatment of septic shock, urinary tract infection, and infections of the gastrointestinal tract, skin or soft tissue.

The compounds, compositions and combinations described herein may also be used to treat or prevent inflammation in a subject. Without being bound by theory, such utility is believed to arise from the activity of the compounds to inhibit the activation of the pro-inflammatory cytokine interleukin-1-β (IL-1β), e.g. by inhibiting activity of LasB enzymes (such as PA LasB) to activate IL-1β by hydrolysis of pro-IL-1β at a distinct site from caspase-1. Accordingly, the compounds, compositions and combinations described herein are particularly suitable for treating inflammation caused by or associated with IL-1β activation in a subject. The compounds, compositions and combinations described herein are especially suitable in treating or preventing bacterial inflammation caused by or associated with IL-1β activation in a subject, particularly when the bacteria causing the infection express one or more LasB enzymes or analogs thereof.

Typically, the compounds, compositions and combinations described herein are especially suitable in treating or preventing respiratory tract inflammation in a subject. The respiratory tract inflammation may be inflammation of any part of the respiratory tract, in particular the lower respiratory tract (e.g. inflammation of the trachea, bronchi or lungs). The compounds described herein are particularly suited to treating or preventing pulmonary inflammation in a subject. The respiratory tract inflammation (e.g. pulmonary inflammation) is typically caused by a bacterial infection, especially by an infection caused by bacteria which express one or more LasB enzymes or analogs thereof, as described above. In some aspects the respiratory tract inflammation (e.g. pulmonary inflammation) is caused by an infection caused by a bacterium of the family Pseudomonadaceae, such as a *Pseudomonas aeruginosa* (PA) infection.

The compounds, compositions and combinations described herein are useful for treating or preventing inflammation in a subject in need thereof. As described in more detail below, the compounds, compositions and combinations described herein are useful in the treatment of patients suffering from cystic fibrosis. The compounds, compositions and combinations described herein are also useful in the treatment of patients suffering from other conditions associated with bacterial inflammation, such as chronic obstructive pulmonary disease (COPD), bronchiectasis, and/or ventilator-associated pneumonia (VAP).

The compounds and combinations are particularly useful in the treatment of patients suffering from cystic fibrosis. Preferably, the compound or combination of the invention may be used in the treatment or prevention of pneumonia in a subject suffering from cystic fibrosis. For example, the subject may have any of the six CFTR mutation classes, and/or may be infected by or chronically colonised by PA. The compounds and combinations of the invention may also be used in the treatment of neutropenic patients.

A compound or combination of the invention can be administered to the subject in order to prevent the onset or reoccurrence of one or more symptoms of the bacterial infection. This is prophylaxis. In this embodiment, the subject can be asymptomatic. The subject is typically one that has been exposed to the bacterium. A prophylactically effective amount of the agent or formulation is administered to such a subject. A prophylactically effective amount is an amount which prevents the onset of one or more symptoms of the bacterial infection.

A compound or combination of the invention can be administered to the subject in order to treat one or more symptoms of the bacterial infection. In this embodiment, the subject is typically symptomatic. A therapeutically effective amount of the agent or formulation is administered to such a subject. A therapeutically effective amount is an amount effective to ameliorate one or more symptoms of the disorder.

A therapeutically or prophylactically effective amount of the compound of the invention is administered to a subject. The dose may be determined according to various parameters, especially according to the compound used; the age, weight and condition of the subject to be treated; the route of administration; and the required regimen. Again, a physician will be able to determine the required route of administration and dosage for any particular subject. A typical daily dose is from about 0.01 to 100 mg per kg, preferably from about 0.1 mg/kg to 50 mg/kg, e.g. from about 1 to 10 mg/kg of body weight, according to the activity of the specific inhibitor, the age, weight and conditions of the subject to be treated, the type and severity of the disease and the frequency and route of administration. Preferably, daily dosage levels are from 5 mg to 2 g.

Other Uses

The antibacterial properties of the compounds described herein mean that they are also useful in the treatment of bacterial infection in vitro, i.e. other than by the treatment of human or animal subjects. Thus, also described herein is a cleaning composition comprising a indane derivative of Formula (I) or a salt thereof. The cleaning composition may further comprise, for example, a detergent, a surfactant (including ionic and non-ionic surfactants), a diluent, a bleach (including a hypochlorite such as sodium hypochlorite or calcium hypochlorite, chlorine, chlorine dioxide, hydrogen peroxide or an adduct thereof, sodium perborate, and sodium percarbonate), an alcohol (such as ethanol or isopropanol), or a disinfectant. Typically, the disinfectant may be selected from benzyl-4-chlorophenol, amylphenol, phenylphenol, glutaraldehyde, alkyl dimethyl benzyl ammonium chloride, alkyl dimethyl ethylbenzyl ammonium chloride, iodine, peracetic acid and chlorine dioxide. Typically, the detergent may be an alkaline detergent such as sodium hydroxide, sodium metasilicate, or sodium carbonate, or an acid detergent such as hydrochloric acid, nitric acid, sulfuric acid, phosphoric acid, citric acid, or tartaric acid.

Also described herein is the use of the indane derivative of Formula (I) as described herein for the prevention or treatment of bacterial contamination in vitro. Such use may be an in vitro method for the prevention or treatment of bacterial infection which comprises a step of treatment of an object with a compound or combination of the invention. Such use is a non-therapeutic use and may involve, for example, prevention or treatment of bacterial contamination on a surface, such as a surface of an indwelling medical device, or an object used in a clinical setting. The surface may be the surface of a catheter, a nebulizer, a ventilator, or a face mask. Typically, the bacterial contamination is caused by any bacteria described herein. Preferably, the bacteria is *Pseudomonas aeruginosa*.

The following Examples illustrate the invention. They do not however, limit the invention in any way. In this regard, it is important to understand that the particular assay used in the Examples section is designed only to provide an indication of biological activity. There are many assays available to determine biological activity, and a negative result in any one particular assay is therefore not determinative.

Experimental Details

General Synthetic Methodology

As described below, there are two synthetic methodologies to synthesize the compounds of the invention.

Method A. Regiospecific Synthesis of Key Intermediate (3)

Scheme 1

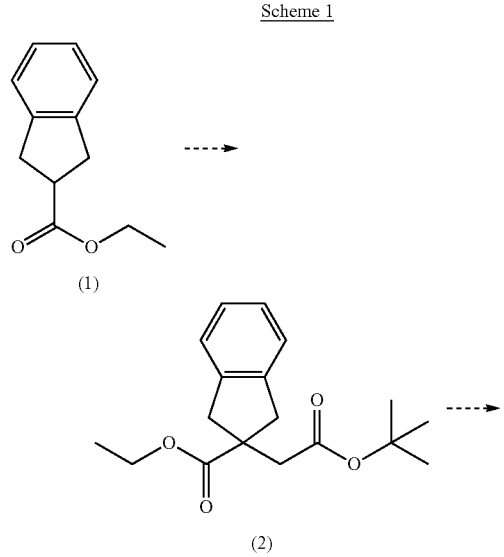

Deprotonation of commercially available ethyl ester (1) with strong base (such as sodium hexamethyldisilazide) then alkylation of the anion with tert-butyl bromoacetate gives known diester (2) (Bell, I. M. and Stump, C. A., WO2006/29153; Robinson, R. P. et al, Bioorganic and Medicinal Chemistry Letters, 1996, 1719). Basic hydrolysis of the ethyl ester in the presence of the tert-butyl ester gives (3) where R=tert-butyl. Amide formation with a suitable 2-aminomethyl benzothiazole followed by treatment with TFA to remove the tert-butyl ester then affords the desired acids.

This methodology can be adapted to substituents on the indane ring.

Scheme 2

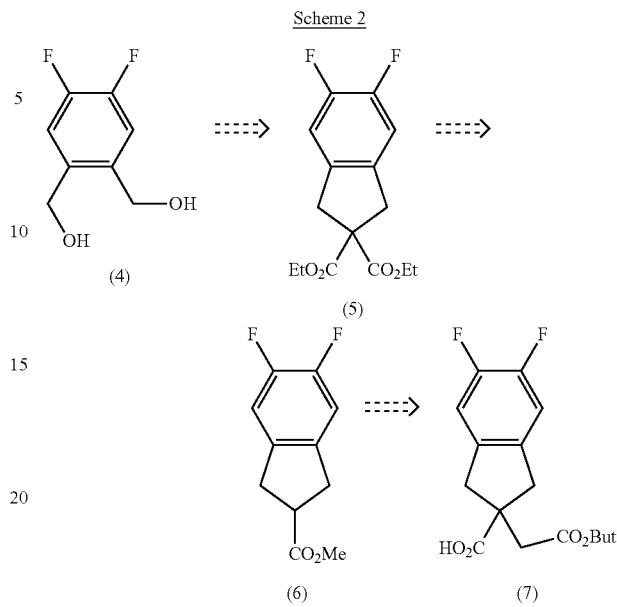

For example commercially available diol [4,5-difluoro-2-(hydroxymethyl)phenyl]methanol (4) can be converted into the bis bromomethyl analogue with either HBr (WO2008/151211) or phosphorus tribromide (US2006/223830) which can further be reacted with diethyl malonate to give indane (5). Standard hydrolysis of both esters followed by mono decarboxylation affords the mono acid (WO2006/125511) which can be esterified to give (6), the difluoro analogue of (1). Using the same methodology as applied to (1) then affords key acid (7), the difluoro analogue of intermediate (3). Similar chemistry can be applied to the corresponding dichloro analogues.

Method B. Synthesis of Protected 2-aminomethyl Benzothiazoles

Scheme 3

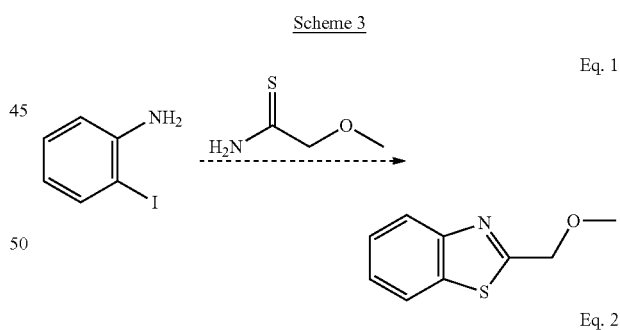

Eq. 1

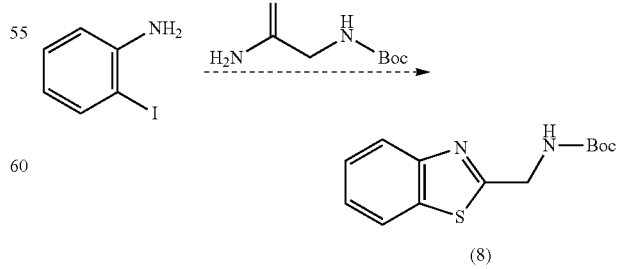

Eq. 2

There are many ways of constructing benzothiazoles (for a review, see Seth, S; "A Comprehensive Review on Recent advances in Synthesis & Pharmacotherapeutic potential of Benzothiazoles", Anti-Inflammatory & Anti-Allergy Agents in Medicinal Chemistry, 2015, 14, 98-112). However, most methods afford alkyl substitution at the C2-position necessitating further functional group manipulation to access the desired aminomethyl substituent required in this invention. In the 1980's the pioneering work of Takagi and colleagues led to a palladium-catalysed method of directly producing functionalised methyl groups (see Eq. 1, Scheme 2; Takagi, K. et al, Chemistry Letters, 1987, 16, 839-840). This chemistry was recently rediscovered by Mutabilis scientists who adapted the methodology to introduce a protected aminomethyl group into the benzothiazole core (8), (see Eq. 2, Scheme 2; Desroy, N., et al, Journal of Medicinal Chemistry, 2013, 56, 1418-1430). Application of this methodology accesses the protected 2-aminomethyl benzothiazoles of this invention.

Method C. Functional Group Manipulation after Protected Aminomethylbenzothiazole In many cases the desired substituent pattern on the phenyl ring can be established prior to benzothiazole formation using standard functional group transformations. In certain cases it is preferred to perform functional group transformations after benzothiazole formation.

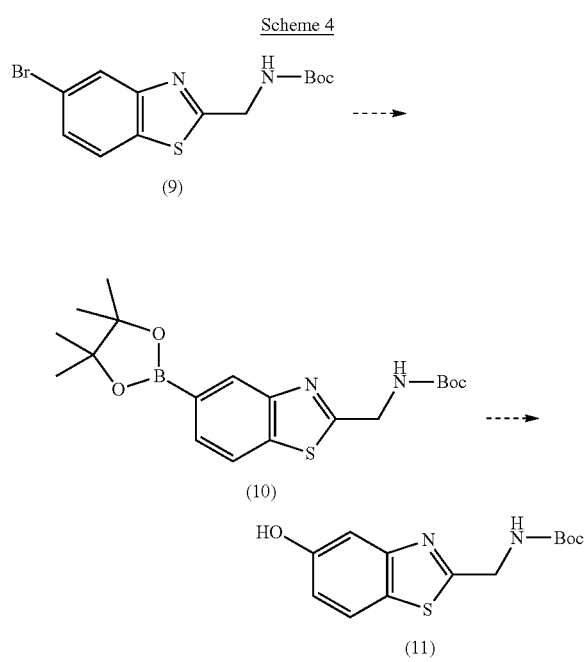

For instance, in order to access a phenolic intermediate on the benzothiazole, one method (Scheme 4) is to construct the benzothiazole with a bromo substituent (9) then displace the bromide using bis(pinacolato)diboron and catalytic Pd(dppf)Cl$_2$·CH$_2$Cl$_2$, affording the boronic ester (10) after aqueous workup (for a related example see Malinger, A. et al, Journal of Medicinal Chemistry, 2016, 59, 1078-1101). Oxidation of the boronic ester to the phenol (11) can be accomplished with hydrogen peroxide (see Liu, J. et al, Tetrahedron Letters, 2017, 58, 1470-1473.) Further derivatisation of the phenol group can be achieved by standard alkylation reactions familiar to those skilled in the art.

Method D. Functional Group Manipulation after Amide Coupling of Aminomethylbenzothiazole and Indanyl Moieties

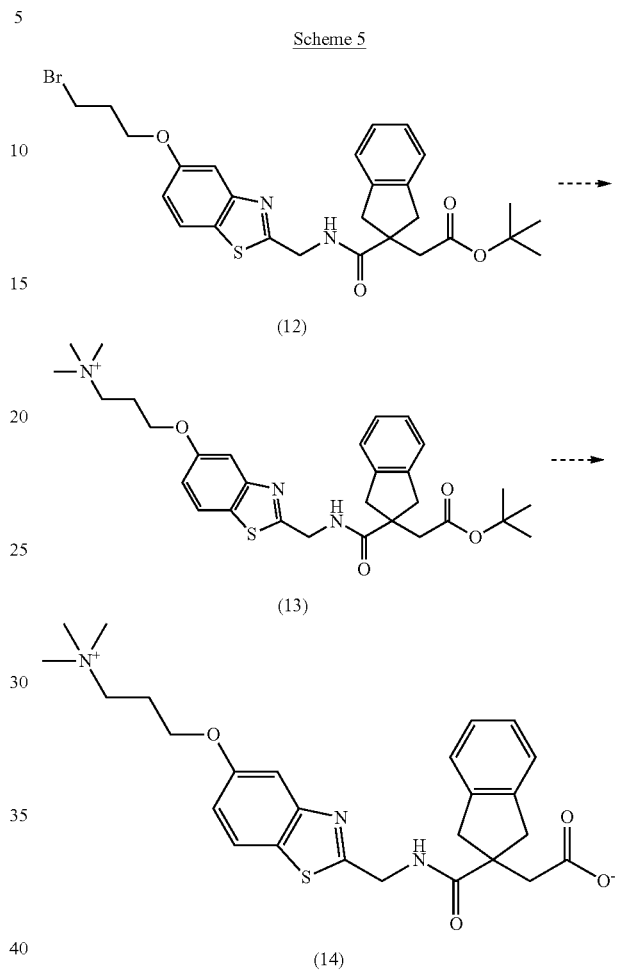

As an example of this approach, alkylation of phenol (11) with 1,3-dibromopropane, removal of the tert-butoxycarbonyl protecting group and coupling with acid (3) can generate the bromopropyloxy intermediate (12). Reaction with a tertiary amine such as trimethylamine then generates the corresponding quaternary ammonium salt (13) and finally removal of the tert-butyl ester reveals the carboxylate acid, generating zwitterionic (14) containing both a positive and a negative charge.

Method E. Synthesis of Amide Substituents on the Benzothiazole Ring

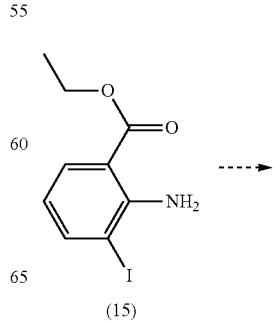

-continued

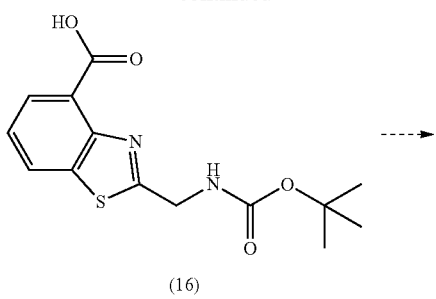

(16)

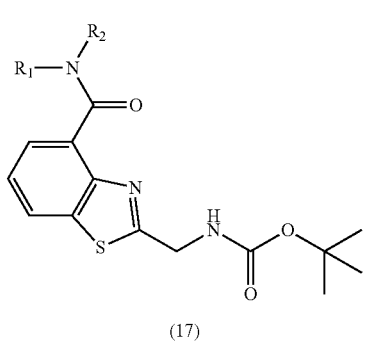

(17)

The ester (15) is subjected to the benzothiazole ring formation procedure during which hydrolysis of the ester also occurs, delivering benzothiazole acid (16). Standard amide formation with amines such as ammonia and pyrrolidine then accesses amides (17).

Method F. Synthesis of Sulfonamide Substituents on the Benzothiazole Ring

-continued

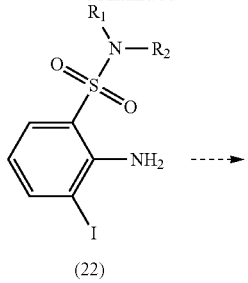

(22)

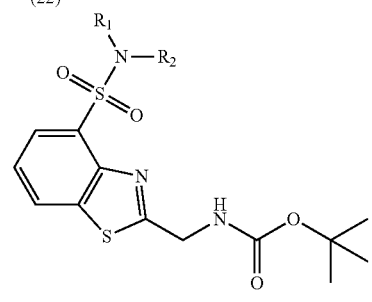

(23)

To access the analogous sulphonamides, different methodology is required. Reaction of o-fluoronitrobenzene (18) with sodium sulphite (see Sisodia, S., et al, Can. J. Chem., 1980, 58, 714-715) results in the sodium salt of the aryl sulfonic acid (19). This can be activated with standard activating agents (see Ashfaq, M., Mini-Reviews in Org. Chem., 2013, 10, 160-170) such as thionyl chloride or phosphoryl chloride to generate the arylsulfonyl chloride (20). Coupling with amines then afford sulphonamides (21). Reduction of the nitro to aniline (22) (for a recent review see Orlandi, M., et al, Organic Process Research and Development, 2018, 22, 430-445) then sets up the precursor for benzothiazole formation, accessing (23).

Method G Final Stages to Synthesise the Examples

Scheme 7

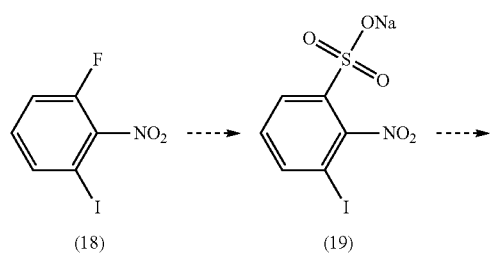

Scheme 8

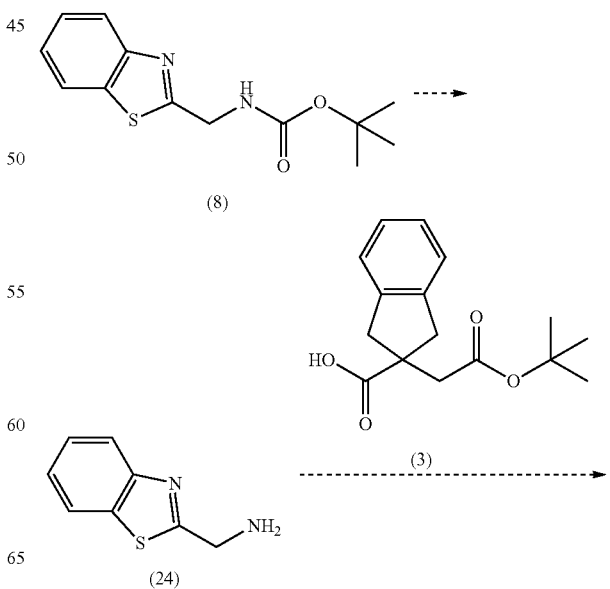

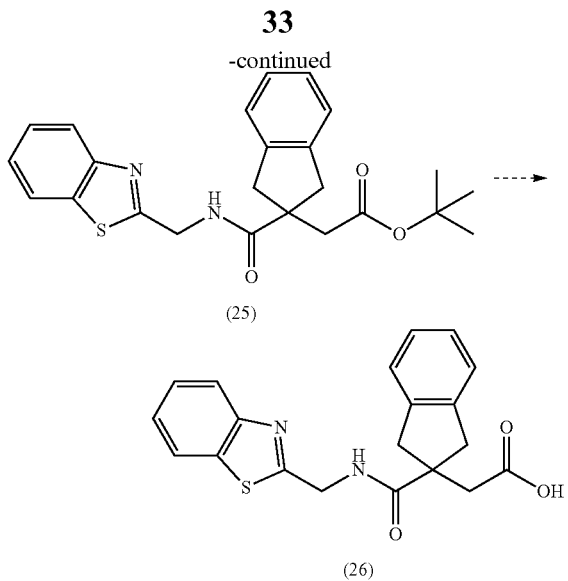

(25)

(26)

The final stages of the syntheses generally involve acid-catalysed removal of the BOC group from (8) to reveal the free amines (24) followed by coupling with acids of type (3), usually with the standard peptide coupling reagent HATU (for a comprehensive review of the myriad available peptide coupling reagents, see Valeur, E. and Bradley, M, Chem. Soc. Rev., 2008, 28, 606-631). Finally further acid treatment with TFA removes the t-butyl ester to afford the Examples of the invention.

It is understood that these synthetic routes are not exclusive and functional group interconversion is possible at the phenyl precursor stage, the protected aminomethyl benzothiazole stage and the post-coupling amide stage.

EXAMPLES

1H NMR spectra are reported at 300, 400 or 500 MHz in DMSO-d6 solutions (δ in ppm), using DMSO-$d_5$ as reference standard (2.50 ppm), or CDCl$_3$ solutions using chloroform as the reference standard (7.26 ppm). When peak multiplicities are reported, the following abbreviations are used: s (singlet), d (doublet), t (triplet), m (multiplet), bs (broadened singlet), bd (broadened doublet), dd (doublet of doublets), dt (doublet of triplets), q (quartet). Coupling constants, when given, are reported in hertz (Hz).

The term "purified by prep hplc (MDAP)" refers compound purification using a mass-directed auto purification system on an Agilent 1260 infinity machine with an XSelect CHS Prep C18 column, eluting with 0.1% FA in water/ACN and detection with a Quadrupole LC/MS.

Abbreviations

ACN Acetonitrile
aq. Aqueous
Bpin Bis(pinacolato)diboron
CaCl$_2$ Calcium chloride
cfu Colony forming unit
Cu(OAc)$_2$ Copper(II) acetate
CuO Copper oxide
DCM Dichloromethane
DIPEA N,N-Diisopropylethylamine
DMF N,N-Dimethylformamide
DMSO Dimethyl sulfoxide
dppf 1,1'-Bis(diphenylphosphino)ferrocene
EDC.HCl N-(3-Dimethylaminopropyl)-N'-ethylcarbodiimide hydrochloride
Et$_2$O Diethyl ether
EtOAc Ethyl acetate
EtOH Ethanol
Et$_3$N Triethylamine
Ex Excitation
FA Formic acid
FCC Flash column chromatography purification on silica
h Hour(s)
HATU 1-[Bis(dimethylamino)methylene]-1H-1,2,3-triazolo[4,5-b]pyridinium 3-oxid hexafluorophosphate
HCl Hydrochloric acid/hydrochloride salt
HOBt Hydroxybenzotriazole
H$_2$SO$_4$ Sulfuric Acid
Km Michaelis constant
MeOH Methanol
min Minute(s)
MgSO$_4$ Magnesium sulfate
NBS N-bromo succinimide
NaHCO$_3$ Sodium bicarbonate
NaHMDS Sodium bis(trimethylsilyl)amide
Na$_2$SO$_4$ Sodium sulfate
Pd$_2$(dba)$_3$ Tris(dibenzylideneacetone)dipalladium(0)
PdCl$_2$(dppf) [1,1'-Bis(diphenylphosphino)ferrocene]dichloropalladium(II)
RT Room temperature
SCX-2 Strong cation exchange resin (silica-propyl sulfonic acid)
TFA Trifluoroacetic acid
THF Tetrahydrofuran
T3P Propylphosphinic anhydride Example 1 2-[2-[(4-carbamoyl-1,3-benzothiazol-2-yl)methylcarbamoyl]indan-2-yl]acetic Acid

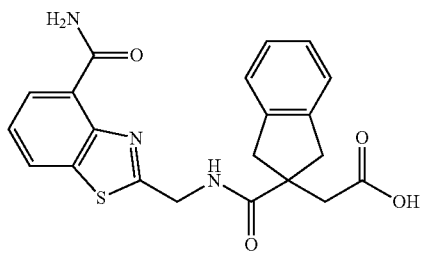 [SMILES: NC(=O)c1cccc2sc(CNC(=O)C3(CC(=O)O)Cc4ccccc4C3)nc12]

a. Ethyl 2-amino-3-iodobenzoate

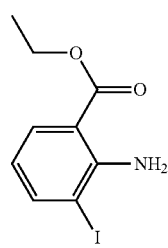

A solution of ethyl 2-aminobenzoate (1.1 g, 3.0 mmol) in toluene (75 mL) was treated with acetic acid (0.34 mL, 3.0 mmol) and N-iodosuccinimide (0.68 g, 3.0 mmol). After 70 h the mixture was washed with saturated aqueous sodium bicarbonate solution, dried (Na$_2$SO$_4$) and evaporated. The residue was chromatographed on silica eluting 0-10% ethyl acetate in toluene affording a red oil that solidified on standing (0.26 g, 29%). M/z 292.5 (M+H)$^+$.

b. 2-({[(Tert-butoxy)carbonyl]amino}methyl)-1,3-benzothiazole-4-carboxylic Acid

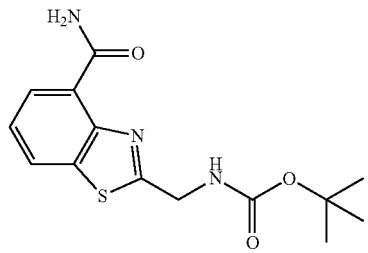 [SMILES: CC(C)(C)OC(=O)NCc1nc2c(C(N)=O)cccc2s1]

A solution of ethyl 2-amino-3-iodobenzoate (147 mg, 0.5 mmol) in ACN (2 mL) was treated with tert-butyl (2-amino-2-thioxoethyl)carbamate (115 mg, 0.61 mmol), calcium oxide (42 mg, 0.76 mmol), tris(dibenzylideneacetone)dipalladium(0) (92 mg, 0.1 mmol) and dppf (224 mg, 0.4 mmol).

The flask was evacuated and refilled with nitrogen twice. The mixture was heated at 60° C. in a sealed vial for 1.5 h then cooled and partitioned between ethyl acetate and 10% aqueous citric acid solution. The aqueous phase was further extracted with ethyl acetate and the combined extracts were dried (Na$_2$SO$_4$) and evaporated. The residue was chromatographed on silica eluting with 0-15% methanol in DCM affording an oil (151 mg, 97%). M/z 331.4 (M+Na)$^+$.

c. Tert-butyl N-[(4-carbamoyl-1,3-benzothiazol-2-yl)methyl]carbamate

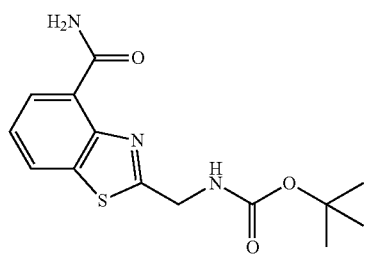 [SMILES: CC(C)(C)OC(=O)NCc1nc2c(C(N)=O)cccc2s1]

A solution of the above 2-({[(tert-butoxy)carbonyl]amino}methyl)-1,3-benzothiazole-4-carboxylic acid (170 mg) in DMF (2 mL) was treated with ammonium chloride (54 mg, 1 mmol), DIPEA (0.35 mL, 2 mmol) and HATU (0.29 g, 2 mmol). After 0.5 h the mixture was partitioned between ethyl acetate and water. The aqueous phase was further extracted with ethyl acetate and the combined extracts were dried (Na2SO4) and evaporated. The residue was chromatographed on silica eluting with 30-100%% ethyl acetate in hexane affording a brown oil (151 mg, 100%). M/z 330.5 (M+Na)$^+$.

d. 2-(Aminomethyl)-1,3-benzothiazole-4-carboxamide

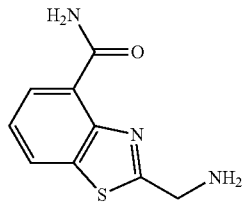 [SMILES: NCc1nc2c(C(N)=O)cccc2s1]

A solution of tert-butyl N-[(4-carbamoyl-1,3-benzothiazol-2-yl)methyl]carbamate (76 mg, 0.25 mmol) in DCM (3 mL) was treated with TFA (0.8 mL). After 1.25 h toluene was added and the mixture evaporated. The residue was treated with a further portion of toluene and evaporated. The residue was added to an SCX cartridge, eluting with methanol then 2M ammonia in methanol affording a pale brown solid (18 mg, 33%). M/z 230.5 (M+Na)$^+$.

e. 2,3-dihydro-1H-indene-2-carboxylate

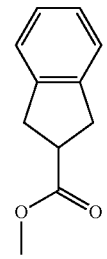

To a stirred solution of 2,3-dihydro-1H-indene-2-carboxylic acid (20 g, 123 mmol) in methanol (200 mL) was added con. H$_2$SO$_4$ (10 mL, 185 mmol) drop wise at room temperature and stirred at 80° C. for 16 h. The reaction mixture was evaporated to get residue. The residue was dissolved in water (100 mL) and extracted with EtOAc (2×100 mL). The organic layer was washed with sat. sodium bicarbonate, brine and evaporated affording a light brown liquid (20 g, 92%). M/z 177.1 (M+H)$^+$.

f. Methyl 2-(2-(tert-butoxy)-2-oxoethyl)-2,3-dihydro-1H-indene-2-carboxylate

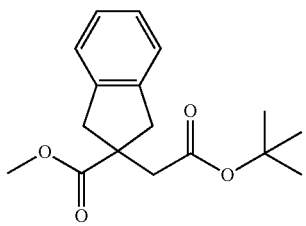 [SMILES: COC(=O)C1(CC(=O)OC(C)(C)C)Cc2ccccc2C1]

To a solution of methyl 2,3-dihydro-1H-indene-2-carboxylate (5 g, 28.3 mmol) in THF (100 mL) was added NaHMDS (21 mL, 42.5 mmol, 2M in THF) at −78° C. under argon and stirred at −78° C. for 1 h. Then tert-butyl 2-bromoacetate solution (6.4 mL, 42.5 mmol) in THF (30 mL) was added drop wise for 15 minutes at −78° C. and stirred at same temperature for 2 h. The reaction mixture was quenched with sat. ammonium chloride solution (50 mL) at −78° C. and allowed to stir at room temperature for 30 minutes. The organic layer was separated, aqueous layer was extracted with EtOAc (2×100 mL), and the combined organic layer was evaporated to get crude compound. The crude compound was triturated with n-pentane (50 mL) at −78° C. and stirred at same temperature for 15 minutes. The resulting solid was filtered and dried under vacuum affording an off white (3.7 g, 45%). M/z=313.0 (M+Na)+.

g. 2-(2-(tert-butoxy)-2-oxoethyl)-2,3-dihydro-1H-indene-2-carboxylic Acid

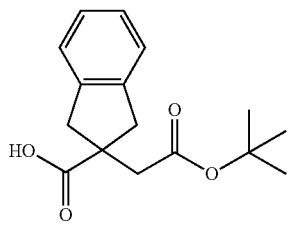 [SMILES: CC(C)(C)OC(=O)CC1(C(=O)O)Cc2ccccc2C1]

To a stirred solution of methyl 2-(2-(tert-butoxy)-2-oxoethyl)-2,3-dihydro-1H-indene-2-carboxylate (430 g, 1.48 mol) in THF (2.15 L) and ethanol (2.15 L) was added 0.5 M LiOH·H$_2$O (6.8 L, 2.96 mol) drop wise at room temperature and stirred at same temperature for 2 h. The reaction mixture was evaporated to get the residue and the residue was diluted with H$_2$O (1 L) and extracted with diethyl ether. The aqueous layer was acidified with 1N HCl to pH 3-4. The resulting precipitate was filtered, washed with water, n-pentane and dried under vacuum affording a white solid (254.5 g, 62%). M/z 275.2 (M−H)−. $^1$H NMR (300 MHz, DMSO-d$_6$): δ 12.4 (1H, bs), 7.18-7.10 (4H, m), 3.39 (2H, d, J=16.2 Hz), 2.92 (2H, d, J=16.2 Hz), 2.64 (2H, s), 1.37 (9H, s).

h. Tert-butyl 2-[2-[(4-carbamoyl-1,3-benzothiazol-2-yl)methylcarbamoyl]indan-2-yl]acetate

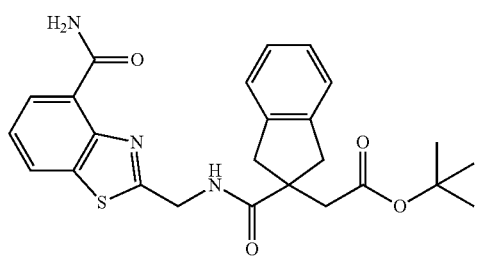 [SMILES: CC(C)(C)OC(=O)CC1(C(=O)NCc2nc3c(C(N)=O)cccc3s2)Cc2ccccc2C1]

A solution of 2-(aminomethyl)-1,3-benzothiazole-4-carboxamide (18 mg, 0.09 mmol), 2-(2-(tert-butoxy)-2-oxoethyl)-2,3-dihydro-1H-indene-2-carboxylic acid (26 mg, 0.1 mmol) and DIPEA (34 mg, 0.26 mmol) in DMF (0.5 mL) was treated with HATU (50 mg, 0.1 mmol). After 0.33 h the mixture was partitioned between ethyl acetate and 10% aqueous citric acid solution. The aqueous phase was further extracted with ethyl acetate and the combined extracts were washed with saturated aqueous sodium chloride solution, dried (Na$_2$SO$_4$) and evaporated. The residue was chromatographed on silica eluting with 50-100%% ethyl acetate in hexane affording a brown oil (36 mg, 90%). M/z 488.2 (M+Na)+.

i. 2-[2-[(4-carbamoyl-1,3-benzothiazol-2-yl)methylcarbamoyl]indan-2-yl]acetic Acid A solution of Tert-butyl 2-[2-[(4-carbamoyl-1,3-benzothiazol-2-yl)methylcarbamoyl]indan-2-yl]acetate (36 mg, 0.08 mmol) in DCM (2 mL) was treated with TFA (0.8 mL). After 1.5 h toluene was added and the mixture evaporated. The residue was treated with a further portion of toluene and evaporated. The residue was chromatographed on silica eluting with 2-12% methanol in DCM to afford the title compound as a white solid (14 mg, 43%). M/z 410.4 (M+H)+. $^1$H NMR (400 MHz, d$_6$-DMSO) δ 12.20 (1H, bs), 9.20 (1H, bs), 9.00 (1H, bs), 8.30 (1H, d), 8.15 (1H, d), 7.90 (1H, bs), 7.55 (1H, t), 7.25 (2H, m), 7.15 (2H, m), 4.75 (2H, d), 3.50 (2H, d), 3.00 (2H, d).

Example 2 2-[2-[[4-(pyrrolidine-1-carbonyl)-1,3-benzothiazol-2-yl]methylcarbamoyl]indan-2-yl]acetic Acid

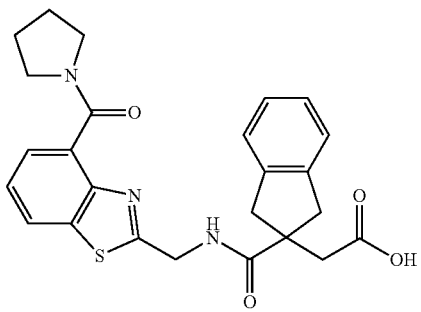 [SMILES: O=C(O)CC1(C(=O)NCc2nc3c(C(=O)N4CCCC4)cccc3s2)Cc2ccccc2C1]

This was prepared in a similar manner to Example 1 with the change that pyrrolidine was used in place of ammonium chloride, giving a white solid (5.0 mg). M/z 464.2 (M+H)+. $^1$H NMR (400 MHz, d$_6$-DMSO) δ 12.20 (1H, bs), 9.00 (1H, bs), 8.10 (1H, d), 7.45 (2H, m), 7.20 (2H, m), 7.10 (2H, m), 4.70 (2H, d), 3.55 (2H, m), 3.50 (2H, d), 3.10 (2H, m), 3.00 (2H, d), 1.90 (2H, m), 1.80 (2H, m).

Example 3 2-[2-[(4-pyrrolidin-1-ylsulfonyl-1,3-benzothiazol-2-yl)methylcarbamoyl]indan-2-yl]acetic Acid

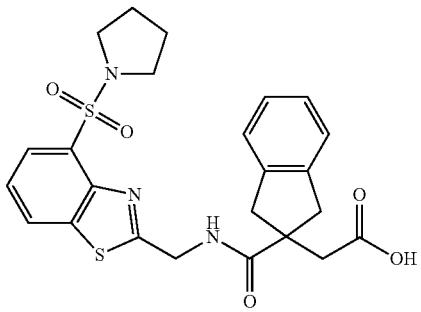 [SMILES: O=C(O)CC1(C(=O)NCc2nc3c(S(=O)(=O)N4CCCC4)cccc3s2)Cc2ccccc2C1]

a. Sodium 3-iodo-2-nitrobenzene-1-sulfonate

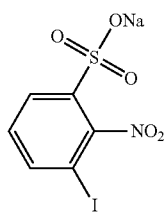

A solution of (commercially available) 1-fluoro-3-iodo-2-nitrobenzene (218 mg, 0.75 mmol) in ethanol (6 mL) was treated with a solution of sodium sulphite (236 mg, 1.9 mmol) in water (5 mL). The mixture was heated to reflux for 4 h. The cooled mixture was evaporated to dryness and chromatographed on reverse phase silica (C-18 cartridge) eluting with water then methanol affording a white solid (144 mg, 55%). M/z 328.2 (M−Na)⁻.

b. 1-(3-Iodo-2-nitrobenzenesulfonyl)pyrrolidine

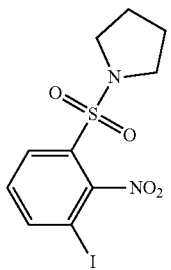 [SMILES: O=[N+]([O-])c1c(I)cccc1S(=O)(=O)N1CCCC1]

A suspension of sodium 3-iodo-2-nitrobenzene-1-sulfonate (133 mg, 0.38 mmol) in thionyl chloride (1 mL) was treated with DMF (1 drop) and the mixture was heated to reflux for 1.5 h then diluted with toluene and evaporated. The residue was re-dissolved in toluene and re-evaporated a further 3 times affording 3-iodo-2-nitrobenzene-1-sulfonyl chloride as an oil (124 mg, 94%). Half of this sample (62 mg, 0.18 mmol) was dissolved in toluene (0.5 mL) and added to a solution of pyrrolidine (213 mg, 3 mmol) in THF (2 mL) at 0° C. After the addition the mixture was stirred at room temperature for 0.5 h then diluted with toluene and evaporated. The residue was chromatographed on silica eluting with 0-5% methanol in DCM affording a colourless solid (65 mg, 96%). M/z 383.3 (M+H)⁺.

c. 2-Iodo-6-(pyrrolidine-1-sulfonyl)aniline

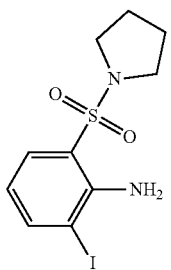 [SMILES: Nc1c(I)cccc1S(=O)(=O)N1CCCC1]

A solution of 1-(3-iodo-2-nitrobenzenesulfonyl)pyrrolidine (65 mg, 0.17 mmol) in ethanol (2 mL) was treated with iron powder (50 mg, 0.9 mmol) then acetic acid (200 mg, 3.4 mmol). The mixture was heated to 85° C. for 1.5 h then filtered through celite, washing with isopropanol. The filtrate was evaporated and the residue chromatographed on silica eluting with 0-15% ethyl acetate in toluene affording a colourless oil (46 mg, 73%). M/z 353.3 (M+H)⁺.

d. Tert-butyl N-{[4-(pyrrolidine-1-sulfonyl)-1,3-benzothiazol-2-yl]methyl}carbamate

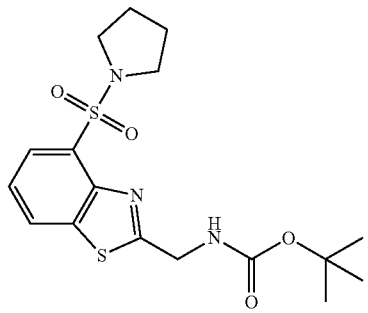 [SMILES: CC(C)(C)OC(=O)NCc1nc2c(S(=O)(=O)N3CCCC3)cccc2s1]

A solution of 2-iodo-6-(pyrrolidine-1-sulfonyl)aniline (46 mg, 0.13 mmol) in in ACN (1 mL) was treated with tert-butyl (2-amino-2-thioxoethyl)carbamate (30 mg, 0.16 mmol), calcium oxide (11 mg, 0.2 mmol), tris(dibenzylideneacetone)dipalladium(0) (24 mg, 0.03 mmol) and dppf (58 mg, 0.11 mmol). The mixture was heated at 60° C. in a sealed vial for 2 h then cooled, diluted with toluene and filtered through celite. The filtrate was added directly to a silica cartridge (10 g) and chromatographed eluting with 0-50% ethyl acetate in toluene affording an oil (33 mg, 64%). M/z 420.2 (M+Na)⁺.

e. [4-(Pyrrolidine-1-sulfonyl)-1,3-benzothiazol-2-yl]methanamine

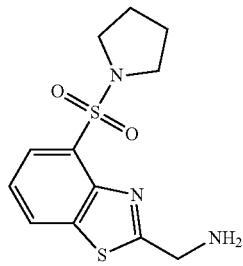 [SMILES: NCc1nc2c(S(=O)(=O)N3CCCC3)cccc2s1]

A solution of tert-butyl N-{[4-(pyrrolidine-1-sulfonyl)-1,3-benzothiazol-2-yl]methyl}carbamate (33 mg, 0.08 mmol) in DCM (2 mL) was treated with TFA (0.5 mL). After 2 h, toluene was added and the mixture evaporated. The residue was treated with a further portion of toluene and evaporated. The residue was dissolved in methanol:DCM (1:1) and loaded onto an SCX cartridge (10 g) and chromatographed eluting with 1M ammonia/methanol. Product-containing fractions were combined and evaporated and the residue further chromatographed on silica eluting with 0-6% 2M ammonia/methanol in DCM affording a brown oil (17 mg, 68%). M/z 298.4 (M+H)⁺.

f. Tert-butyl 2-[2-[(4-pyrrolidin-1-ylsulfonyl-1,3-benzothiazol-2-yl)methylcarbamoyl]indan-2-yl]acetate

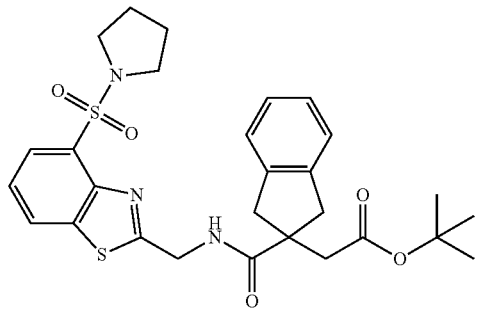 [SMILES: CC(C)(C)OC(=O)CC1(C(=O)NCc2nc3c(S(=O)(=O)N4CCCC4)cccc3s2)Cc2ccccc2C1]

A solution of [4-(pyrrolidine-1-sulfonyl)-1,3-benzothiazol-2-yl]methanamine (18 mg, 0.06 mmol), 2-(2-(tert-butoxy)-2-oxoethyl)-2,3-dihydro-1H-indene-2-carboxylic acid (18 mg, 0.07 mmol) and DIPEA (23 mg, 0.03 mmol) in DMF (0.5 mL) was treated with HATU (34 mg, 0.9 mmol). After 0.5 h the mixture was partitioned between ethyl acetate and 10% aqueous citric acid solution. The aqueous phase was further extracted with ethyl acetate and the combined extracts were washed with saturated aqueous sodium chloride solution, dried ($Na_2SO_4$) and evaporated. The residue was chromatographed on silica eluting with 30-60% ethyl acetate in hexane affording a brown oil (33 mg, 100%). M/z 578.3 (M+Na)$^+$.

g. 2-[2-[(4-pyrrolidin-1-ylsulfonyl-1,3-benzothiazol-2-yl)methylcarbamoyl]indan-2-yl]acetic Acid A solution of tert-butyl 2-[2-[(4-pyrrolidin-1-ylsulfonyl-1,3-benzothiazol-2-yl)methylcarbamoyl]indan-2-yl]acetate (33 mg, 0.06 mmol) in DCM (2 mL) was treated with TFA (0.8 mL). After 1.75 h toluene was added and the mixture evaporated. The residue was treated with a further portion of toluene and evaporated. The residue was chromatographed on silica eluting with 2-10% methanol in DCM to afford the title compound as a white solid (19 mg, 62%). M/z 500.1 (M+H)$^+$. $^1$H NMR (400 MHz, d$_6$-DMSO) δ 12.30 (1H, bs), 9.00 (1H, bs), 8.40 (1H, d), 7.95 (1H, d), 7.58 (1H, t), 7.23 (2H, m), 7.15 (2H, m), 4.70 (2H, d), 3.50 (2H, d), 3.40 (4H, m), 3.00 (2H, d), 1.7-1.6 (4H, m).

Example 4 2-[2-[(4-sulfamoyl-1,3-benzothiazol-2-yl)methylcarbamoyl]indan-2-yl]acetic Acid

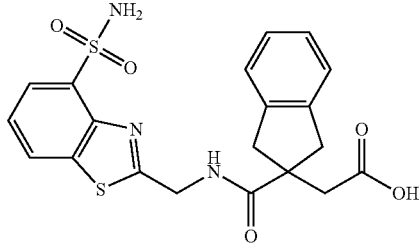 [SMILES: NS(=O)(=O)c1cccc2sc(CNC(=O)C3(CC(=O)O)Cc4ccccc4C3)nc12]

This was prepared by the same methodology as Example 3 with the exception that ammonium chloride (source of ammonia) was used instead of pyrrolidine in the sulphonamide formation step with 3-iodo-2-nitrobenzene-1-sulfonyl chloride. The title compound was isolated as a white solid (15 mg). M/z 446.1 (M+H)$^+$. $^1$H NMR (400 MHz, d$_6$-DMSO) δ 12.00 (1H, bs), 8.30 (1H, d), 7.92 (1H, d), 7.55 (1H, t), 7.30 (2H, s), 7.20 (2H, m), 7.10 (2H, m), 4.80 (2H, d), 3.45 (2H, d), 3.00 (2H, d).

Example 5 2-[2-[(4-piperazin-1-ylsulfonyl-1,3-benzothiazol-2-yl)methylcarbamoyl]indan-2-yl]acetic Acid

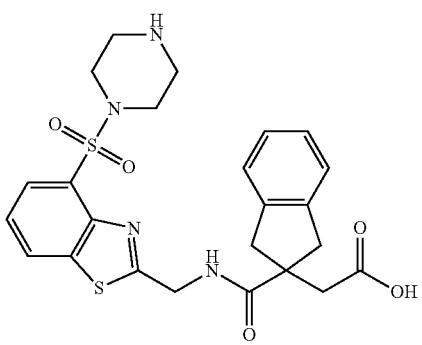 [SMILES: O=C(O)CC1(C(=O)NCc2nc3c(S(=O)(=O)N4CCNCC4)cccc3s2)Cc2ccccc2C1]

This was prepared by the same methodology as Example 3 with the exception that benzyl piperazine-1-carboxylate was used instead of pyrrolidine in the sulphonamide formation step with 3-iodo-2-nitrobenzene-1-sulfonyl chloride and removal of the benzyl carbamate protecting group necessitated a reaction time of 55 h at room temperature in neat TFA. The title compound was isolated after purification as a white solid (9 mg). M/z 515.3 (M+H)$^+$. $^1$H NMR (400 MHz, d$_6$-DMSO) δ 10.00 (1H, bs), 8.40 (1H, d), 7.95 (1H, d), 7.60 (1H, t), 7.20 (2H, m), 7.10 (2H, m), 4.75 (2H, d), 3.50 (4H, m), 3.20 (2H, m), 3.00 (2H, d), 2.80 (2H, m), 2.60 (2H, m).

Example 6 2-[2-[[4-(3-aminopyrrolidin-1-yl)sulfonyl-1,3-benzothiazol-2-yl]methylcarbamoyl]indan-2-yl]acetic Acid

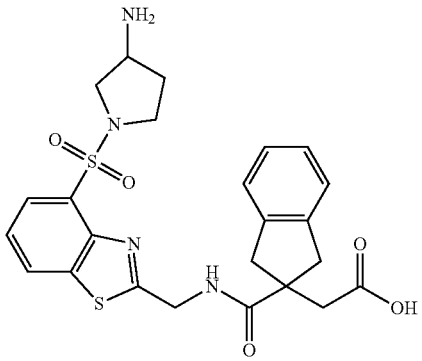 [SMILES: NC1CCN(S(=O)(=O)c2cccc3sc(CNC(=O)C4(CC(=O)O)Cc5ccccc5C4)nc23)C1]

This was prepared by the same methodology as Example 3 with the exception that (R, S)-benzyl N-(pyrrolidin-3-yl)carbamate was used instead of pyrrolidine in the sulphonamide formation step with 3-iodo-2-nitrobenzene-1-sulfonyl chloride and removal of the benzyl carbamate protecting group necessitated a reaction time of 48 h at room temperature in neat TFA. The title compound was isolated as a white solid (14 mg). M/z 515.4 (M+H)+. 1H NMR (400 MHz, d6-DMSO) δ 11.00 (1H, bs), 8.40 (1H, d), 8.00 (1H, d), 7.60 (1H, t), 7.20 (2H, m), 7.15 (2H, m), 4.75 (2H, m), 4.00 (1H, t), 3.60-3.20 (6H, m), 3.00-2.85 (2H, m), 1.95 (1H, m), 1.70 (1H, m).

Example 7 2-[2-[(4-methylsulfonyl-1,3-benzothiazol-2-yl)methylcarbamoyl]indan-2-yl]acetic Acid

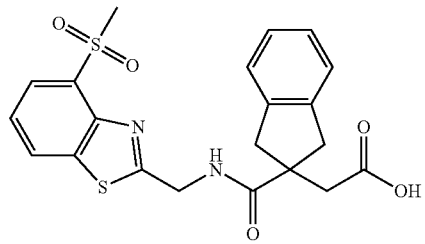 [SMILES: CS(=O)(=O)c1cccc2sc(CNC(=O)C3(CC(=O)O)Cc4ccccc4C3)nc12]

a. 1-Iodo-3-methanesulfonyl-2-nitrobenzene

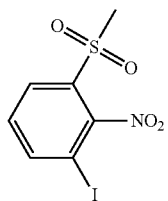

A solution of 2-fluoro-3-iodo-2-nitrobenzene (200 mg, 0.75 mmol) in THF (6 mL) was treated portionwise with sodium thiomethoxide then 15-crown-5 (1,4,7,10,13-pentaoxacyclopentadecane) (20 mg) was added. After 7 h, the mixture was diluted with DCM (6 mL) and 3-chloroperbenzoic acid (672 mg, 3 mmol) was added. After 16 h the mixture was partitioned between ethyl acetate and 10% aqueous sodium metabisulfite solution. The aqueous phase was further extracted with ethyl acetate and the combined organic extracts washed with saturated aqueous sodium bicarbonate solution, saturated aqueous sodium chloride solution, dried (Na2SO4) and evaporated. The residue was chromatographed on silica eluting with 0-100% ethyl acetate in toluene affording a white solid (227 mg). This was further purified by chromatography on silica eluting with 0-2% methanol in chloroform affording a colourless solid (92 mg, 38%). M/z 246.3 (M+H)+.

b. 2-[2-[(4-methylsulfonyl-1,3-benzothiazol-2-yl)methylcarbamoyl]indan-2-yl]acetic Acid This was prepared from 1-iodo-3-methanesulfonyl-2-nitrobenzene by the same reaction sequence as described for Example (3c) onwards, affording the title compound as a white solid (34 mg). M/z 445.4 (M+H)+. 1H NMR (400 MHz, d6-DMSO) δ 12.20 (1H, bs), 8.90 (1H, bs), 8.45 (1H, d), 8.00 (1H, d), 7.62 (1H, t), 7.22 (2H, m), 7.15 (2H, m), 4.75 (2H, d), 3.52 (3H, s), 3.50 (2H, d), 3.00 (2H, d).

Example 8 2-[2-[[6-methoxy-5-[2-(4-methylpiperazin-1-yl)-2-oxo-ethoxy]-1,3-benzothiazol-2-yl]methylcarbamoyl]indan-2-yl]acetic Acid

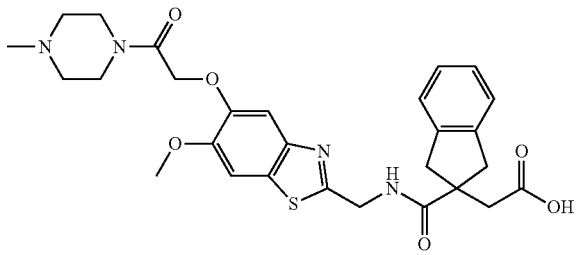 [SMILES: COc1cc2sc(CNC(=O)C3(CC(=O)O)Cc4ccccc4C3)nc2cc1OCC(=O)N1CCN(C)CC1]

a. 4-bromo-5-methoxy-2-nitroaniline

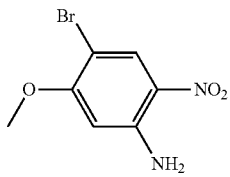

To a stirred solution of 5-methoxy-2-nitroaniline (100 g, 595 mmol) in acetonitrile (2.5 L) was added NBS (106 g, 595 mmol) portion wise at room temperature. The mixture was cooled to 0° C. and added TFA (46 mL, 595 mmol) drop wise for 30 minutes and allowed to stir at room temperature for 16 h. The reaction mixture was diluted with water (1 L) and adjusted the pH to ~8 with 1N NaOH. The resulting precipitate was filtered, washed with water (500 mL) and dried under vacuum affording a yellow solid. (105 g, 72%). M/z 247 (M+H)+.

b. 1-Bromo-4-iodo-2-methoxy-5-nitrobenzene

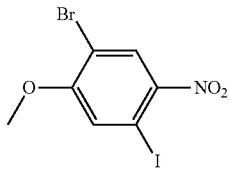

To a stirred solution of 4-bromo-5-methoxy-2-nitroaniline (50 g, 203 mmol) in acetonitrile (750 mL) was added concentrated H2SO4 (24 mL, 457 mmol) drop wise at −10° C. Then NaNO2 (28 g, 406 mmol) in water (175 mL) was added drop wise at −10° C. for 15 minutes and stirred at same temperature for 30 min. After that KI solution (135 g, 813 mmol) in water (175 mL) was added drop wise at −10° C. for 20 minutes and stirred at same temperature for 30 min. The reaction mixture was quenched with sodium metabisulphite solution (309 g, 1.62 mmol) in water (1.6 L) at −10° C. to 0° C. for 1 h. Then water (1 L) was added and allowed to stir at room temperature for 30 minutes. The resulting precipitate was filtered, washed with water (1 L) and dried under vacuum affording a yellow solid. (60 g, 82%). M/z 357.8 (M+H)+.

c. 5-Bromo-2-iodo-4-methoxyaniline

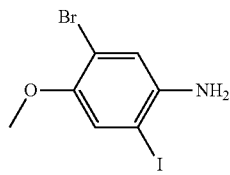

To a stirred solution of 1-bromo-4-iodo-2-methoxy-5-nitrobenzene (106 g, 296 mmol) in EtOH: H₂O (800 mL: 200 mL) was added Fe (49.7 g, 890 mmol), NH₄Cl (80 g, 1.48 mmol) at room temperature and stirred at 90° C. for 2 h. Then the reaction mixture was cooled to 60° C., added additional amount of Fe (33 g, 593 mmol), NH₄Cl (80 g 1.48 mmol) and stirred at 90° C. for 30 minutes. The reaction mixture was filtered through celite pad, washed the pad with methanol (1 L) and filtrate was concentrated to give residue. The residue was diluted with cold water (1 L) and adjusted the pH to ~8 with 1N NaOH. The resulting precipitate was filtered and dried under vacuum affording a light brown solid (90 g, 92%). M/z 327.8 (M+H)⁺.

d. Tert-butyl N-[(5-bromo-6-methoxy-1,3-benzothiazol-2-yl)methyl]carbamate

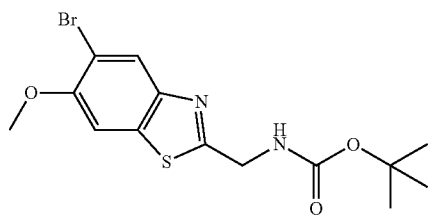 [SMILES: COc1cc2sc(CNC(=O)OC(C)(C)C)nc2cc1Br]

To a stirred solution of 5-bromo-2-iodo-4-methoxyaniline (50 g, 152 mmol) in acetonitrile (560 mL) was added tert-butyl (2-amino-2-thioxoethyl) carbamate (35 g, 183 mmol), CaO (17 g, 305 mmol) and degassed with argon for 20 minutes. Then Pd₂(dba)₃ (14 g, 15.2 mmol), dppf (25.4 g, 15.8 mmol) was added and purged with argon for further 5 minutes and the reaction mixture was stirred at 80° C. for 4 hour. The reaction mixture was filtered through celite pad and washed the pad with EtOAc (300 mL). The filtrate was washed with water and evaporated to get crude compound. The crude compound was dissolved in acetonitrile (200 mL), on standing for 1 h solid was precipitated out. The resulting solid was filtered, washed with acetonitrile (50 mL) and dried under vacuum affording an off white solid (34 g, 60%). M/z 372.9 (M+H)⁺.

e. Tert-butyl N-[[6-methoxy-5-(4,4,5,5-tetramethyl-1,3,2-dioxaborolan-2-yl)-1,3-benzothiazol-2-yl]methyl]carbamate

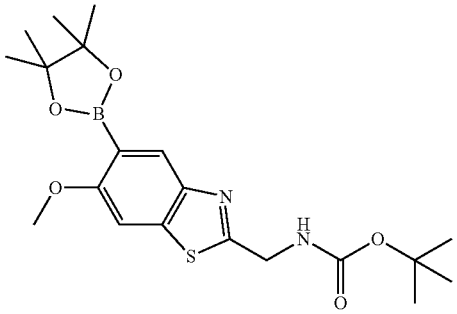 [SMILES: COc1cc2sc(CNC(=O)OC(C)(C)C)nc2cc1B1OC(C)(C)C(C)(C)O1]

To a stirred solution of tert-butyl ((5-bromo-6-methoxy-benzo[d]thiazol-2-yl)methyl)carbamate (5 g, 13.44 mmol) in dioxane (100 mL) was added BPin (6.8 g, 26.8 mmol), KOAc (4.6 g, 47.0 mmol) and purged with argon for 15 minutes. Then Pd₂Cl₂(dppf). DCM (1.1 g, 1.34 mmol) was added and purged with argon for further 5 minutes. The reaction mixture was heated at 100° C. for 16 h. The reaction mixture was filtered through celite pad and washed the pad with EtOAc (50 mL). The filtrate was washed with water, brine and evaporated affording a white solid (12 g, crude). M/z 339 (M+H)⁺.

f. Tert-butyl N-[(5-hydroxy-6-methoxy-1,3-benzothiazol-2-yl)methyl]carbamate

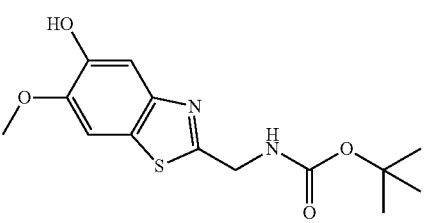 [SMILES: COc1cc2sc(CNC(=O)OC(C)(C)C)nc2cc1O]

To a stirred solution of tert-butyl N-[[6-methoxy-5-(4,4,5,5-tetramethyl-1,3,2-dioxaborolan-2-yl)-1,3-benzothiazol-2-yl]methyl]carbamate (12 g, 35.5 mmol) in THF (180 mL) was added 1N NaOH (35 mL, 35.5 mmol), 30% H₂O₂ (6.2 mL 81.6 mmol) at 0° C. and stirred at same temperature for 30 minutes. The reaction mixture was partitioned between water and EtOAc. The organic layer was separated washed with water, brine and evaporated to get crude compound. The crude compound was chromatographed on silica eluting with 30% EtOAc in petroleum ether affording an off white solid. (2.5 g 54%). M/z 311.0 (M+H)⁺. ¹H NMR (500 MHz, CDCl₃): δ 7.50 (1H, s), 7.25 (1H, s), 5.76 (1H, s), 5.30 (1H, s), 4.68 (2H, d, J=5.5 Hz), 3.97 (3H, s), 1.54 (9H, s). M/z 311.0 (M+H)⁺.

g. Tert-butyl N-({6-methoxy-5-[2-(4-methylpiperazin-1-yl)-2-oxoethoxy]-1,3-benzothiazol-2-yl}methyl)carbamate

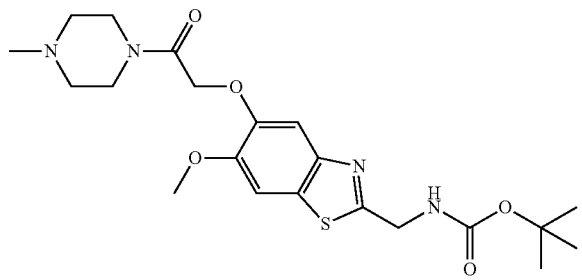 [SMILES: COc1cc2sc(CNC(=O)OC(C)(C)C)nc2cc1OCC(=O)N1CCN(C)CC1]

A mixture of tert-butyl N-[(5-hydroxy-6-methoxy-1,3-benzothiazol-2-yl)methyl]carbamate (310 mg, 1 mmol), (commercially-available) 1-(2-chloroacetyl)-4-methyl-piperazine hydrochloride (234 mg, 1.1 mmol) and caesium carbonate (980 mg, 3 mmol) in ACN (3 mL) was stirred for 18 h then partitioned between DCM and saturated aqueous sodium chloride solution, and then the organic phase was dried (Na$_2$SO$_4$) and evaporated. The residue was chromatographed on silica eluting with 2-10% 7M ammonia/methanol in DCM affording a white solid (268 mg, 59%). M/z 451.6 (M+H)$^+$.

h. 2-{[2-(Aminomethyl)-6-methoxy-1,3-benzothiazol-5-yl]oxy}-1-(4-methylpiperazin-1-yl)ethan-1-one

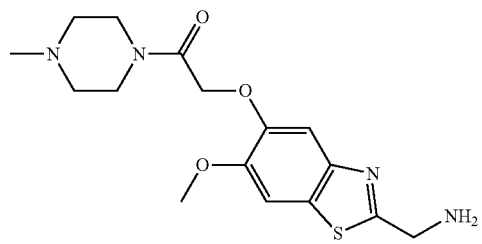 [SMILES: COc1cc2sc(CN)nc2cc1OCC(=O)N1CCN(C)CC1]

A solution of tert-butyl N-({6-methoxy-5-[2-(4-methylpiperazin-1-yl)-2-oxoethoxy]-1,3-benzothiazol-2-yl}methyl)carbamate (265 mg, 0.6 mmol) in DCM (3 mL) was treated with TFA (1.4 mL). After 1 h the mixture was added to an SCX-2 cartridge, pre-washed with methanol. This was washed with methanol then eluted to 7M ammonia/methanol. This latter fraction was evaporated to give an orange foam (195 mg, 95%). M/z 351.6 (M+H)$^+$.

i. Tert-butyl 2-[2-[[6-methoxy-5-[2-(4-methylpiperazin-1-yl)-2-oxo-ethoxy]-1,3-benzothiazol-2-yl]methylcarbamoyl]indan-2-yl]acetate

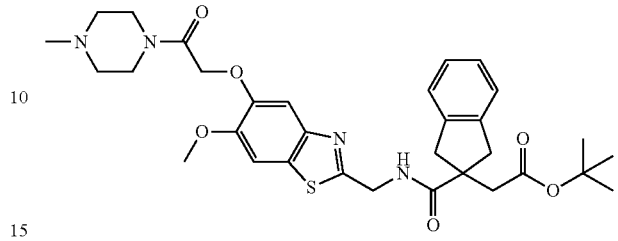

A solution of 2-{[2-(aminomethyl)-6-methoxy-1,3-benzothiazol-5-yl]oxy}-1-(4-methylpiperazin-1-yl)ethan-1-one (151 mg, 0.55 mmol), 2-(2-(tert-butoxy)-2-oxoethyl)-2,3-dihydro-1H-indene-2-carboxylic acid (192 mg, 0.55 mmol) and triethylamine (0.23 mL, 166 mg, 0.66 mmol) in DCM (3 mL) was treated with HATU (250 mg, 0.66 mmol). After 2 h the mixture was partitioned between ethyl acetate and saturated aqueous sodium chloride solution. The organic phase was dried (Na$_2$SO$_4$) and evaporated. The residue was chromatographed on silica eluting with 2-10% 7M ammonia/methanol in DCM affording an off-white solid (209 mg, 63%). M/z 609.7 (M+H)$^+$.

j. 2-[2-[[6-methoxy-5-[2-(4-methylpiperazin-1-yl)-2-oxo-ethoxy]-1,3-benzothiazol-2-yl]methylcarbamoyl]indan-2-yl]acetic Acid A solution of tert-butyl 2-[2-[[6-methoxy-5-[2-(4-methylpiperazin-1-yl)-2-oxo-ethoxy]-1,3-benzothiazol-2-yl]methylcarbamoyl]indan-2-yl]acetate (206 mg, 0.33 mol) in DCM (3 mL) was treated with water (0.2 mL) then TFA (1.6 mL). After 2 h the mixture was evaporated. Toluene was added and the mixture re-evaporated. The residue was subjected to MDAP purification followed by freeze-drying of product-containing fractions to afford the title compound as white solid (108 mg, 58%). M/z 553.4 (M+H)$^+$. $^1$H NMR (400 MHz, d$_6$-DMSO) δ 8.80 (1H, bs), 7.60 (1H, s), 7.40 (1H, s), 7.20 (2H, m), 7.10 (2H, m) 4.90 (2H, s), 4.60 (2H, d), 3.80 (3H, s), 3.50 (4H, m), 3.00 (2H, d), 2.70 (2H, m), 2.40 (2H, m), 2.30 (2H, m), 2.20 (3H, s).

Example 9 2-[2-[[6-methoxy-5-(2-morpholinoethoxy)-1,3-benzothiazol-2-yl]methylcarbamoyl]indan-2-yl]acetic Acid

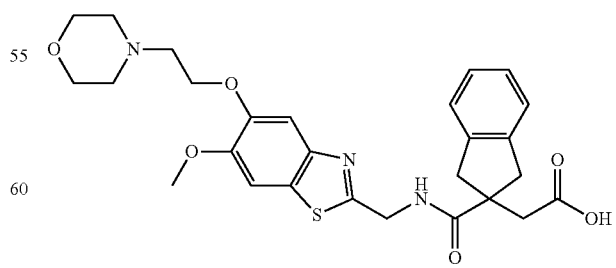

This was prepared as a white solid (101 mg) in an analogous manner to Example 8 with the change that commercially-available 4-(2-chloroethyl)morpholine hydrochloride was used in place of 1-(2-chloroacetyl)-4-methylpiperazine hydrochloride. M/z 526.4 (M+H)⁺. $^1$H NMR (400 MHz, d$_6$-DMSO) δ 12.00 (1H, bs), 8.80 (1H, bs), 7.60 (1H, s), 7.50 (1H, s), 7.20 (2H, m), 7.10 (2H, m), 4.60 (2H, d), 4.20 (2H, m), 3.80 (3H, s), 3.70 (2H, m), 3.50 (2H, d), 3.45-3.30 (10H, m), 3.00 (2H, d).

Example 10 2-[5,6-difluoro-2-[[6-methoxy-5-(2-morpholinoethoxy)-1,3-benzothiazol-2-yl]methylcarbamoyl]indan-2-yl]acetic Acid

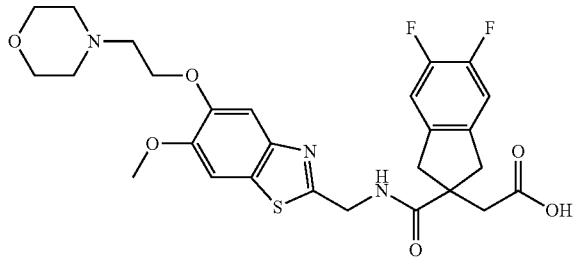 [SMILES: COc1cc2sc(CNC(=O)C3(CC(=O)O)Cc4cc(F)c(F)cc4C3)nc2cc1OCCN1CCOCC1]

a. Dimethyl 4,5-difluorophthalate

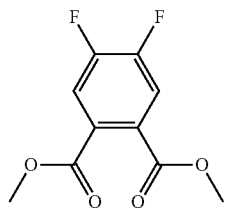

To an ice-cooled solution of 4,5-difluorophthalic acid (11.9 g, 58.9 mmol) in MeOH (250 mL) was added concentrated H$_2$SO$_4$ (40 mL, 0.75 mol) keeping the temperature <20° C. The mixture was stirred at 65° C. for 4 h. The cooled reaction mixture was concentrated in vacuo, then the residue was cautiously added to EtOAc and aq. NaHCO$_3$. The aq. phase was extracted with EtOAc and the combined organic extracts were washed with aq. NaHCO$_3$, then brine, dried (Na$_2$SO$_4$), filtered and concentrated in vacuo to yield the title compound as a colourless oil (12.98 g, 96%). $^1$H NMR (CDCl$_3$) δ 7.56 (2H, t, J=8.7 Hz), 3.91 (6H, s).

b. (4,5-Difluoro-1,2-phenylene)dimethanol

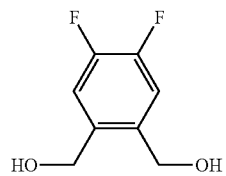 [SMILES: OCc1cc(F)c(F)cc1CO]

To an ice-cooled solution of lithium aluminium hydride (1M in THF, 226 mL, 0.226 mol) was added a solution of dimethyl 4,5-difluorophthalate (12.98 g, 56.4 mmol) in THF (100 mL) over 30 min keeping the temperature below 12° C. The mixture was stirred in the ice bath for 30 min, then at RT for 1 h. The reaction mixture was cooled to 0° C. then, cautiously, water (8.5 mL), 15% aq. NaOH (8.5 mL) and water (26 mL) were added successively, keeping the temperature below 15° C. Celite was added and the mixture stirred at RT for 1 h, then filtered through a celite pad, washing through with more THF. The filtrate was concentrated in vacuo to yield the title compound as a white solid (9.52 g, 97%). $^1$H NMR (d6-DMSO) δ 7.36 (2H, t, J=10.1 Hz), 5.29 (2H, t, J=5.5 Hz), 4.47 (4H, d, J=5.4 Hz).

c. 1,2-Bis(bromomethyl)-4,5-difluorobenzene

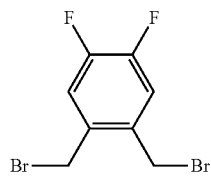

A mixture of (4,5-difluoro-1,2-phenylene)dimethanol (9.52 g, 54.7 mmol) and 48% hydrobromic acid (68.5 mL) was stirred at 110° C. for 1 h. The cooled reaction mixture was diluted with water and then extracted with Et$_2$O. The aq. phase was extracted with Et$_2$O and the combined organic extracts were washed with water, then brine, dried (Na$_2$SO$_4$), filtered and concentrated in vacuo to leave a residue. FCC (1-10% EtOAc in hexane) to yield the title compound as a colourless oil (15.2 g, 93%). $^1$H NMR (CDCl$_3$) δ 7.20 (2H, t, J=9.1 Hz), 4.55 (4H, s).

d. Diethyl 5,6-difluoro-1,3-dihydro-2H-indene-2,2-dicarboxylate

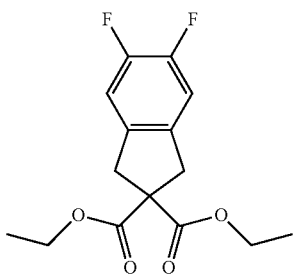 [SMILES: CCOC(=O)C1(C(=O)OCC)Cc2cc(F)c(F)cc2C1]

Sodium hydride (60% in oil, 4.46 g, 112 mmol) was added over 15 min to a mixture of 1,2-bis(bromomethyl)-4,5-difluorobenzene (15.2 g, 50.7 mmol) and diethyl malonate (9.74 g, 60.8 mmol) in THF (200 mL) keeping the temperature below 20° C. The mixture was stirred at RT for 4 h, then saturated ammonium chloride was added. The mixture was concentrated in vacuo and then extracted twice with EtOAc. The combined organic extracts were washed with brine, dried (Na$_2$SO$_4$), filtered and concentrated in vacuo to leave a residue. FCC (5-25% EtOAc in hexane) yielded the title compound as a colourless oil (9.95 g, 66%). $^1$H NMR (CDCl$_3$) δ 6.97 (2H, t, J=8.7 Hz), 4.21 (4H, q, J=7.1 Hz), 3.52 (4H, s), 1.26 (6H, t, J=7.1 Hz).

e. 5,6-Difluoro-2,3-dihydro-1H-indene-2-carboxylic Acid

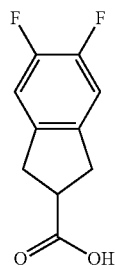

To a solution of diethyl 5,6-difluoro-1,3-dihydro-2H-indene-2,2-dicarboxylate (9.94 g, 33.3 mmol) in dioxane (130 mL) was added water (130 mL) and concentrated HCl (140 mL). The mixture was refluxed for 23 h. The cooled reaction mixture was diluted with water and extracted with Et$_2$O (×3). The combined organic extracts were washed with water, then brine, dried (Na$_2$SO$_4$), filtered and concentrated in vacuo to yield the title compound as a colourless solid (6.6 g, quant.). M/z 197 (M−H)⁻.

f. Methyl 5,6-difluoro-2,3-dihydro-1H-indene-2-carboxylate

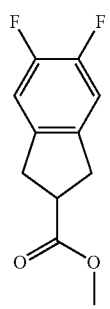

To an ice-cooled solution of 5,6-difluoro-2,3-dihydro-1H-indene-2-carboxylic acid (6.6 g, 33.3 mmol) in MeOH (200 mL) was added concentrated H$_2$SO$_4$ (40 mL, 0.75 mol) keeping the temperature <20° C. The mixture was stirred at 65° C. for 1 h. The cooled reaction mixture was concentrated in vacuo, then the residue was cautiously added to EtOAc and aq. NaHCO$_3$. The aq. phase was extracted with more EtOAc and the combined organic extracts were washed with brine, dried (Na$_2$SO$_4$), filtered and concentrated in vacuo to leave a residue. FCC (5-25% EtOAc in hexane) yielded the title compound as a pale yellow solid (5.97 g, 84%). ¹H NMR (CDCl$_3$) δ 6.98 (2H, t, J=8.8 Hz), 3.73 (3H, s), 3.39 (1H, m), 3.24-3.12 (4H, m).

g. Methyl 2-(2-(tert-butoxy)-2-oxoethyl)-5,6-difluoro-2,3-dihydro-1H-indene-2-carboxylate

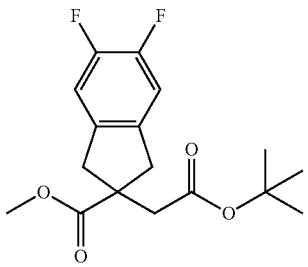 [SMILES: COC(=O)C1(CC(=O)OC(C)(C)C)Cc2cc(F)c(F)cc2C1]

To a solution of methyl 5,6-difluoro-2,3-dihydro-1H-indene-2-carboxylate (5.97 g, 28.2 mmol) in THF (120 mL), cooled to −78° C., was added sodium bis(trimethylsilyl)amide (1M in THF, 42.2 mL, 42.2 mol) over 15 min. The mixture was stirred at −78° C. for 45 min then a solution of tert-butyl bromoacetate (8.24 g, 42.2 mmol) in THF (15 mL) was added over 10 min. The reaction mixture was allowed to warm to −10° C. over 1 h. Saturated ammonium chloride was added, the mixture was concentrated under reduced pressure. The residue was extracted twice with EtOAc and the combined organic extracts were washed with brine, dried (Na$_2$SO$_4$), filtered and concentrated in vacuo to leave a residue. FCC (5-20% EtOAc in hexane) yielded the title compound as a pale yellow gum (8.78 g, 96%). ¹H NMR (CDCl$_3$) δ 6.96 (2H, t, J=8.9 Hz), 3.72 (3H, s), 3.47 (2H, d, J=16.2 Hz), 2.90 (2H, d, J=16.2 Hz), 2.71 (2H, s), 1.42 (9H, s).

h. 2-[(tert-butoxy)carbonyl]-5,6-difluoro-2,3-dihydro-1H-indene-2-carboxylic Acid

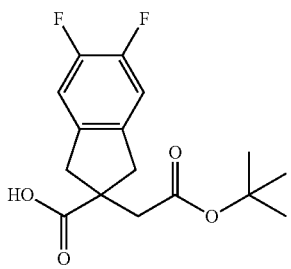 [SMILES: CC(C)(C)OC(=O)CC1(C(=O)O)Cc2cc(F)c(F)cc2C1]

To a solution of methyl 2-(2-(tert-butoxy)-2-oxoethyl)-5,6-difluoro-2,3-dihydro-1H-indene-2-carboxylate (0.834 g, 2.56 mmol) in THF (25 mL) and MeOH (10 mL) was added lithium hydroxide (0.5M in water, 10.2 mL, 5.1 mmol). The mixture was stirred at RT for 2.5 h, then concentrated in vacuo. The residual solution was layered with EtOAc and acidified by addition of 6M HCl. The aq. phase was extracted with more EtOAc and the combined organic extracts were washed with brine, dried (Na$_2$SO$_4$), filtered and concentrated in vacuo to leave a residue. FCC (2-6% MeOH in DCM) yielded the title compound as a cream solid (0.59 g, 74%). ¹H NMR (d6-DMSO) δ 12.47 (1H, bs), 7.26 (2H, t, J=9.2 Hz), 3.33 (2H, d, J=16.4 Hz), 2.91 (2H, d, J=16.4 Hz), 2.67 (2H, s), 1.37 (9H, s). M/z 311 (M−H)⁻.

i. 2-[5,6-difluoro-2-[[6-methoxy-5-(2-morpholino-ethoxy)-1,3-benzothiazol-2-yl]methylcarbamoyl]indan-2-yl]acetic Acid The title product was prepared as a white solid (18 mg) in an analogous manner to Example 9 with the change that 2-[(tert-butoxy)carbonyl]-5,6-difluoro-2,3-dihydro-1H-indene-2-carboxylic acid was used in place of 2-[(tert-butoxy)carbonyl]-2,3-dihydro-1H-indene-2-carboxylic acid. M/z 562.4 (M+H)$^+$. $^1$H NMR (400 MHz, d$_6$-DMSO) δ 12.00 (1H, bs), 8.80 (1H, bs), 7.60 (1H, s), 7.50 (1H, s), 7.30 (2H, t), 4.60 (2H, d), 4.20 (2H, t), 3.80 (3H, s), 3.60 (2H, t), 3.45 (2H, d), 3.30 (4H, m), 3.00 (2H, d), 2.75 (4H, m).

Example 11 2-[5,6-difluoro-2-[[6-methoxy-5-[(1-methyl-4-piperidyl)methoxy]-1,3-benzothiazol-2-yl]methylcarbamoyl]indan-2-yl]acetic Acid

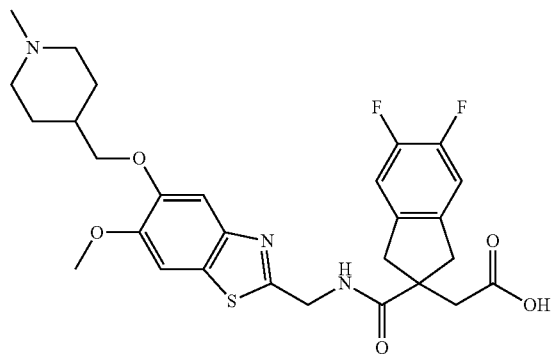 [SMILES: COc1cc2sc(CNC(=O)C3(CC(=O)O)Cc4cc(F)c(F)cc4C3)nc2cc1OCC1CCN(C)CC1]

This was prepared in a similar manner to Example 10 except that (1-methylpiperidin-4-yl)methanol hydrochloride was used in the alkylation step instead of 4-(2-chloroethyl)morpholine hydrochloride, affording the title compound as a white solid (58 mg). M/z 560.4 (M+H)$^+$. $^1$H NMR (400 MHz, d$_6$-DMSO) δ 9.00 (1H, bs), 7.60 (1H, s), 7.45 (1H, s), 7.20 (2H, t), 4.65 (2H, d), 3.95 (2H, m), 3.85 (3H, s), 3.45 (2H, d), 2.95 (2H, d), 2.80 (2H, m), 2.30 (3H, s), 2.00 (2H, m), 1.80 (3H, m), 1.40 (2H, m).

Example 12 2-[5,6-difluoro-2-[[6-methoxy-5-[2-(4-methylpiperazin-1-yl)-2-oxo-ethoxy]-1,3-benzothiazol-2-yl]methylcarbamoyl]indan-2-yl]acetic Acid a. Tert-butyl 2-[5,6-difluoro-2-[[6-methoxy-5-[2-(4-methylpiperazin-1-yl)-2-oxo-ethoxy]-1,3-benzothiazol-2-yl]methylcarbamoyl]indan-2-yl]acetate

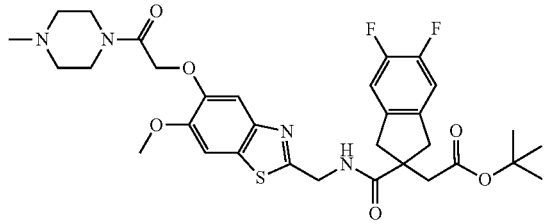 [SMILES: COc1cc2sc(CNC(=O)C3(CC(=O)OC(C)(C)C)Cc4cc(F)c(F)cc4C3)nc2cc1OCC(=O)N1CCN(C)CC1]

A solution of 2-{[2-(aminomethyl)-6-methoxy-1,3-benzothiazol-5-yl]oxy}-1-(4-methylpiperazin-1-yl)ethan-1-one (151 mg, 0.43 mmol), 2-[(tert-butoxy)carbonyl]-5,6-difluoro-2,3-dihydro-1H-indene-2-carboxylic acid (135 mg, 0.43 mmol) and triethylamine (0.18 mL, 131 mg, 1.3 mmol) in DCM (3 mL) was treated with HATU (197 mg, 0.52 mmol). After 2 h the mixture was partitioned between DCM and saturated aqueous sodium chloride solution. The organic phase was dried (Na$_2$SO$_4$) and evaporated. The residue was chromatographed on silica eluting with 1-10% 7M ammonia/methanol in DCM affording an off-white solid (169 mg, 61%). M/z 645.7 (M+H)$^+$.

b. 2-[5,6-difluoro-2-[[6-methoxy-5-[2-(4-methylpiperazin-1-yl)-2-oxo-ethoxy]-1,3-benzothiazol-2-yl]methylcarbamoyl]indan-2-yl]acetic Acid A solution of tert-butyl 2-[5,6-difluoro-2-[[6-methoxy-5-[2-(4-methylpiperazin-1-yl)-2-oxo-ethoxy]-1,3-benzothiazol-2-yl]methylcarbamoyl]indan-2-yl]acetate (65 mg, 0.1 mol) in DCM (2 mL) was treated with water (0.05 mL) then TFA (0.5 mL). After 2 h the mixture was evaporated. Toluene was added and the mixture re-evaporated. The residue was subjected to MDAP purification followed by freeze-drying of product-containing fractions to afford the title compound as white solid (11 mg, 19%). M/z 589.6 (M+H)$^+$. $^1$H NMR (400 MHz, d$_6$-DMSO) δ 12.20 (1H, bs), 9.80 (1H, bs), 7.60 (1H, s), 7.50 (1H, s), 7.25 (2H, t), 4.95 (2H, m), 4.65 (2H, m), 4.40 (1H, m), 4.10 (1H, m), 3.95 (2H, m), 3.80 (3H, s), 3.70-3.50 (3H, m), 3.45 (2H, d), 3.15 (1H, m), 3.00 (2H, d), 2.80 (3H, s).

Example 13 2-[5,6-difluoro-2-[[6-methoxy-5-[2-(4-methylmorpholin-4-ium-4-yl)ethoxy]-1,3-benzothiazol-2-yl]methylcarbamoyl]indan-2-yl]acetate

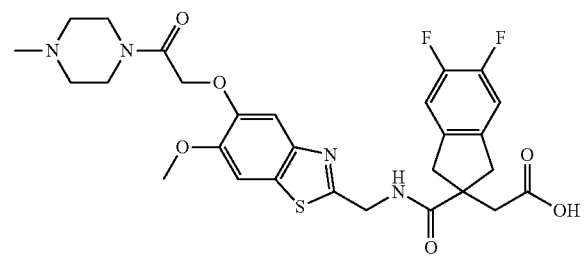

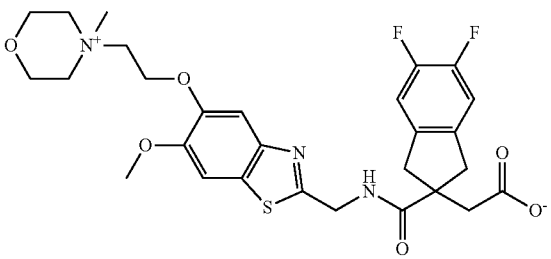 [SMILES: COc1cc2sc(CNC(=O)C3(CC(=O)[O-])Cc4cc(F)c(F)cc4C3)nc2cc1OCC[N+]1(C)CCOCC1]

a. Tert-butyl 2-[5,6-difluoro-2-[[6-methoxy-5-[2-(4-methylmorpholin-4-ium-4-yl)ethoxy]-1,3-benzothiazol-2-yl]methylcarbamoyl]indan-2-yl]acetate Iodide

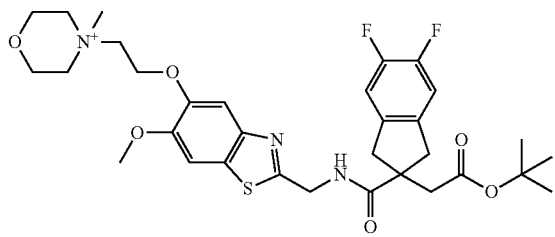 [SMILES: COc1cc2sc(CNC(=O)C3(CC(=O)OC(C)(C)C)Cc4cc(F)c(F)cc4C3)nc2cc1OCC[N+]1(C)CCOCC1]

A solution of tert-butyl 5,6-difluoro-2-[({6-methoxy-5-[2-(morpholin-4-yl)ethoxy]-1,3-benzothiazol-2-yl}methyl)carbamoyl]-2,3-dihydro-1H-indene-2-carboxylate (see Example 10) (140 mg, 0.23 mmol) in THF (2 mL) was treated with iodomethane (161 mg, 0.07 mL, 1.1 mmol) and stirred overnight. Evaporation gave an oil (0.2 g) which was used directly in the next step. M/z 632.6 (M)$^+$ b. 2-[5,6-difluoro-2-[[6-methoxy-5-[2-(4-methylmorpholin-4-ium-4-yl)ethoxy]-1,3-benzothiazol-2-yl]methylcarbamoyl]indan-2-yl]acetate A solution of the above tert-butyl 2-[5,6-difluoro-2-[[6-methoxy-5-[2-(4-methylmorpholin-4-ium-4-yl)ethoxy]-1,3-benzothiazol-2-yl]methylcarbamoyl]indan-2-yl]acetate iodide (0.2 g, 0.23 mmol) in DCM (2 mL) was treated with water (0.1 mL) then TFA (1 mL). After 2 h the mixture was evaporated. Toluene was added and the mixture re-evaporated. The residue was subjected to MDAP purification followed by freeze-drying of product-containing fractions to afford the title compound as white solid (54 mg, 41%). M/z 576.4 (M+H)$^+$. $^1$H NMR (400 MHz, d$_6$-DMSO) δ 12.90 (1H, bs), 7.65 (1H, s), 7.60 (1H, s), 7.20 (2H, t), 4.65 (2H, m), 4.60 (2H, m), 4.10-3.90 (6H, m), 3.85 (3H, s), 3.70-3.50 (4H, m), 3.40 (2H, d), 3.30 (3H, s), 2.90 (2H, d).

Example 14 2-[2-[[5-[2-(4,4-dimethylpiperazin-4-ium-1-yl)-2-oxo-ethoxy]-6-methoxy-1,3-benzothiazol-2-yl]methylcarbamoyl]-5,6-difluoro-indan-2-yl]acetate

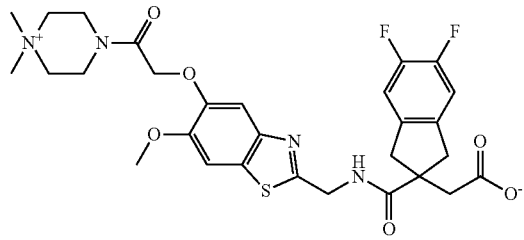 [SMILES: COc1cc2sc(CNC(=O)C3(CC(=O)[O-])Cc4cc(F)c(F)cc4C3)nc2cc1OCC(=O)N1CC[N+](C)(C)CC1]

This was prepared from tert-butyl 5,6-difluoro-2-[({6-methoxy-5-[2-(4-methylpiperazin-1-yl)-2-oxoethoxy]-1,3-benzothiazol-2-yl}methyl)carbamoyl]-2,3-dihydro-1H-indene-2-carboxylate, the precursor to Example 12, using the quaternisation with iodomethane followed by TFA deprotection protocol as described for Example 8 step-j to afford the title compound as a white solid (48 mg). M/z 603.3 (M+H)$^+$. $^1$H NMR (400 MHz, d$_6$-DMSO) δ 13.10 (1H, bs), 7.68 (1H, s), 7.50 (1H, s), 7.25 (2H, t), 4.95 (2H, m), 4.60 (2H, m), 4.00-3.90 (4H, m), 3.85 (3H, s), 3.50 (2H, m), 3.40 (2H, m), 3.20 (6H, s), 2.90 (2H, d), 2.40 (2H, d).

Example 15 2-[5,6-difluoro-2-[[6-methoxy-5-[3-(4-methylmorpholin-4-ium-4-yl)propoxy]-1,3-benzothiazol-2-yl]methylcarbamoyl]indan-2-yl]acetate

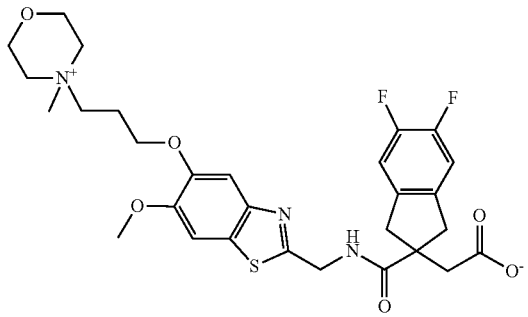 [SMILES: COc1cc2sc(CNC(=O)C3(CC(=O)[O-])Cc4cc(F)c(F)cc4C3)nc2cc1OCCC[N+]1(C)CCOCC1]

This was prepared from tert-butyl 5,6-difluoro-2-[({6-methoxy-5-[3-(morpholin-4-yl)propoxy]-1,3-benzothiazol-2-yl}methyl)carbamoyl]-2,3-dihydro-1H-indene-2-carboxylate, which was accessed using the same chemistry as for Example 10 with the change that 4-(2-chloropropyl)morpholine hydrochloride was used in the phenol alkylation step. Quaternisation of tert-butyl 5,6-difluoro-2-[({6-methoxy-5-[3-(morpholin-4-yl)propoxy]-1,3-benzothiazol-2-yl}methyl)carbamoyl]-2,3-dihydro-1H-indene-2-carboxylate with iodomethane followed by TFA deprotection protocol as described for Example 13 to afford the title compound as a white solid (80 mg). M/z 590.4 (M+H)$^+$. $^1$H NMR (400 MHz, d$_6$-DMSO) δ 11.80 (1H, bs), 7.60 (1H, s), 7.50 (1H, s), 7.25 (2H, t), 4.60 (2H, d), 4.20 (2H, t), 4.00 (2H, m), 3.87 (3H, s), 3.70 (2H, m), 3.50 (2H, m), 3.35 (2H, d), 3.20 (3H, s), 3.00 (2H, d), 2.80 (2H, m), 2.50 (2H, m), 2.25 (2H, m).

Example 16 2-[2-[[6-methoxy-5-[3-(4-methylmorpholin-4-ium-4-yl)propoxy]-1,3-benzothiazol-2-yl]methylcarbamoyl]indan-2-yl]acetate

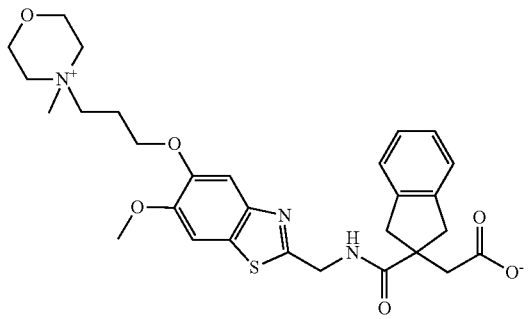 [SMILES: COc1cc2sc(CNC(=O)C3(CC(=O)[O-])Cc4ccccc4C3)nc2cc1OCCC[N+]1(C)CCOCC1]

This was prepared from tert-butyl 2-[({6-methoxy-5-[3-(morpholin-4-yl)propoxy]-1,3-benzothiazol-2-yl}methyl)carbamoyl]-2,3-dihydro-1H-indene-2-carboxylate, which was accessed using the same chemistry as for Example 8 with the change that 4-(2-chloropropyl)morpholine hydrochloride was used in the phenol alkylation step. Quaternisation of tert-butyl 2-[({6-methoxy-5-[3-(morpholin-4-yl)propoxy]-1,3-benzothiazol-2-yl}methyl)carbamoyl]-2,3-dihydro-1H-indene-2-carboxylate with iodomethane followed by TFA deprotection protocol as described for Example 13 to afford the title compound as a white solid. M/z 554.2 (M+H)$^+$. $^1$H NMR (500 MHz, DMSO-d$_6$): δ 11.80 (1H, bs), 7.63 (1H, s), 7.54 (1H, s), 7.18-7.16 (2H, m), 7.12-7.10 (2H, m), 4.61 (2H, d, J=5.5 Hz), 4.14 (2H, t, J=6.5 Hz), 3.94-3.92 (4H, m), 3.83 (3H, s), 3.66-3.63 (2H, m), 3.48-3.42 (4H, m), 3.39-3.35 (2H, bs), 3.17 (3H, s), 2.91 (2H, d, J=16.5 Hz), 2.46 (2H, s), 2.25-2.22 (2H, m).

Example 17 2-[2-[[5-[(1,1-dimethylpiperidin-1-ium-4-yl)methoxy]-6-methoxy-1,3-benzothiazol-2-yl]methylcarbamoyl]indan-2-yl]acetate

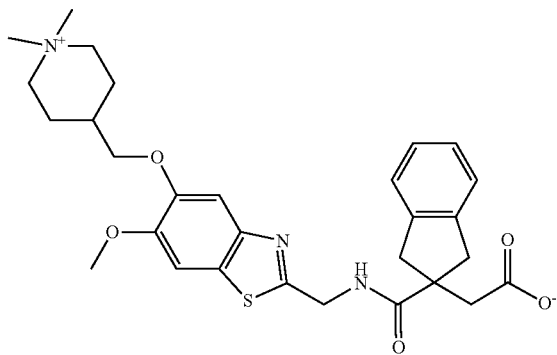 [SMILES: COc1cc2sc(CNC(=O)C3(CC(=O)[O-])Cc4ccccc4C3)nc2cc1OCC1CC[N+](C)(C)CC1]

This was prepared from tert-butyl 2-[2-[[6-methoxy-5-[(1-methyl-4-piperidyl)methoxy]-1,3-benzothiazol-2-yl]methylcarbamoyl]indan-2-yl]acetate, which was accessed using the same chemistry as for Example 8 with the change that 4-(chloromethyl)-1-methyl-piperidine was used in the phenol alkylation step. Quaternisation of tert-butyl 2-[2-[[6-methoxy-5-[(1-methyl-4-piperidyl)methoxy]-1,3-benzothiazol-2-yl]methylcarbamoyl]indan-2-yl]acetate with iodomethane followed by TFA deprotection protocol as described for Example 13 to afford the title compound as a white solid. M/z 538.1 (M+H)$^+$. $^1$H NMR (500 MHz, DMSO-d$_6$): δ 11.32 (1H, bs), 7.61 (1H, s), 7.50 (1H, s), 7.18-7.16 (2H, m), 7.12-7.10 (2H, m), 4.61 (2H, d, J=5.5 Hz), 4.02 (2H, d, J=6.5 Hz), 3.82 (3H, s), 3.45-3.33 (6H, bs), 3.10 (3H, s), 3.05 (3H, s), 2.91 (2H, d, J=16 Hz), 2.55-2.45 (2H, bs), 2.07-2.04 (1H, m), 1.94-1.92 (2H, m), 1.79-1.74 (2H, m).

Example 18 2-[2-[[5-[3-[diethyl(methyl)ammonio]propoxy]-6-methoxy-1,3-benzothiazol-2-yl]methylcarbamoyl]indan-2-yl]acetate

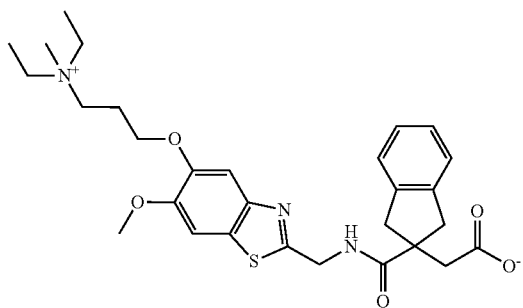 [SMILES: CC[N+](C)(CC)CCCOc1cc2nc(CNC(=O)C3(CC(=O)[O-])Cc4ccccc4C3)sc2cc1OC]

a. Tert-butyl N-({5-[3-(diethylamino)propoxy]-6-methoxy-1,3-benzothiazol-2-yl}methyl)carbamate

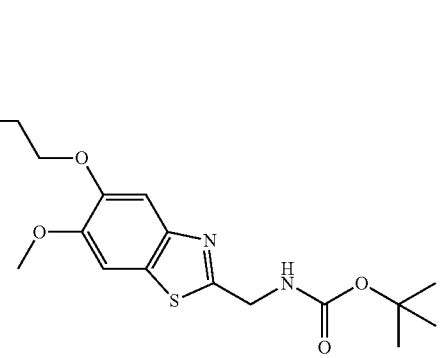

A solution of tert-butyl N-[(5-hydroxy-6-methoxy-1,3-benzothiazol-2-yl)methyl]carbamate (100 mg, 0.32 mmol), 3-diethylamino-1-propanol (50 mg, 0.38 mmol) and triphenylphosphine (100 mg, 0.38 mmol) in THF (2 mL) was treated with diethyl azodicarboxylate (67 mg, 0.38 mmol). After 2 h, 3-diethylamino-1-propanol (25 mg, 0.19 mmol), triphenylphosphine (50 mg, 0.19 mmol) and diethyl azodicarboxylate (34 mg, 0.19 mmol) were added. After 0.5 h, the mixture was diluted with toluene and evaporated. The residue was chromatographed on silica eluting with 2-12% 2M ammonia/methanol in DCM affording a pale-yellow oil (118 mg, 86%). M/z 424.4 (M+H)$^+$.

b. (3-{[2-({[(Tert-butoxy)carbonyl]amino}methyl)-6-methoxy-1,3-benzothiazol-5-yl]oxy}propyl)diethylmethylazanium Iodide

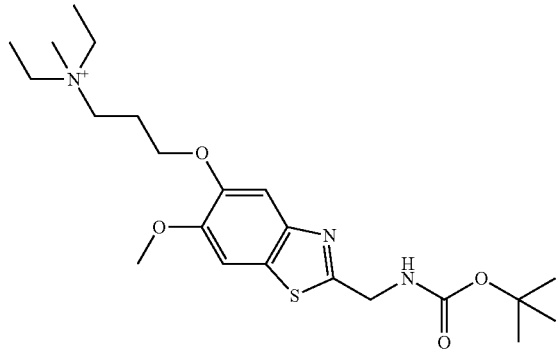 [SMILES: CC[N+](C)(CC)CCCOc1cc2nc(CNC(=O)OC(C)(C)C)sc2cc1OC]

A solution of tert-butyl N-({5-[3-(diethylamino)propoxy]-6-methoxy-1,3-benzothiazol-2-yl}methyl)carbamate (118 mg, 0.28 mmol) in ACN (3 mL) was treated with iodomethane (200 mg, 0.9 mmol). After 16 h the mixture was evaporated to dryness and the residue chromatographed on silica eluting with 3-20% 2M ammonia/methanol in DCM affording a colourless oil (95 mg, 61%). M/z 438.5 (M)⁺.

c. (3-{[2-(Aminomethyl)-6-methoxy-1,3-benzothiazol-5-yl]oxy}propyl)diethylmethylazanium Chloride, Hydrochloride Salt

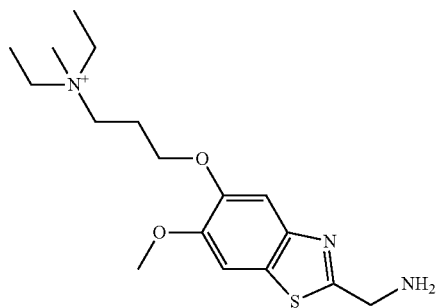 [SMILES: CC[N+](C)(CC)CCCOc1cc2nc(CN)sc2cc1OC]

A solution of (3-{[2-({[(tert-butoxy)carbonyl]amino}methyl)-6-methoxy-1,3-benzothiazol-5-yl]oxy}propyl)diethylmethylazanium iodide (95 mg, 0.17 mmol) in methanol (1 mL) was treated with 4M hydrochloric acid in 1,4-dioxane (3 mL, 12 mmol). After 1.5 h, toluene was added and the mixture evaporated to give an oil (100 mg). M/z 338.4 (M)⁺.

d. 3-[[2-[[[2-(2-tert-butoxy-2-oxo-ethyl)indane-2-carbonyl]amino]methyl]-6-methoxy-1,3-benzothiazol-5-yl]oxy]propyl-diethyl-methyl-ammonium Chloride

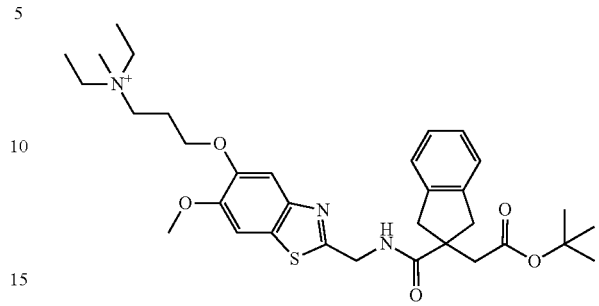

A solution of (3-{[2-(aminomethyl)-6-methoxy-1,3-benzothiazol-5-yl]oxy}propyl)diethylmethylazanium chloride, hydrochloride salt (100 mg), 2-(2-(tert-butoxy)-2-oxoethyl)-2,3-dihydro-1H-indene-2-carboxylic acid (51 mg, 0.18 mmol) and DIPEA (65 mg, 0.5 mmol) in DMF (1.5 mL) was treated with HATU (95 mg, 0.18 mmol). After 20 minutes the mixture was chromatographed on reverse phase C18 silica eluting with 20-50% 0.01M hydrochloric acid in ACN. Product-containing fractions were freeze-dried to afford a light brown solid (94 mg, 89% over the two stages). M/z 596.4 (M)⁺.

e. 2-[2-[[5-[3-[diethyl(methyl)ammonio]propoxy]-6-methoxy-1,3-benzothiazol-2-yl]methylcarbamoyl]indan-2-yl]acetate A solution of 3-[[2-[[[2-(2-tert-butoxy-2-oxo-ethyl)indane-2-carbonyl]amino]methyl]-6-methoxy-1,3-benzothiazol-5-yl]oxy]propyl-diethyl-methyl-ammonium chloride (94 mg, 0.15 mmol) in DCM (3 mL) was treated with TFA (1.5 mL). After 2 h toluene was added and the mixture evaporated.

The residue was chromatographed on reverse phase C18 silica eluting with 10-30% 2M ammonia/methanol in ACN. Product-containing fractions were freeze-dried to afford the title compound as a white solid (37 mg, 46%). M/z 540.3 (M+H)⁺. ¹H NMR (400 MHz, d₆-DMSO) δ 11.50 (1H, bs), 7.65 (1H, s), 7.52 (1H, s), 7.20 (2H, m), 7.10 (2H, m), 4.62 (2H, d), 4.15 (2H, t), 3.85 (3H, s), 3.50-3.20 (6H, m), 3.00 (3H, s), 2.90 (2H, d), 2.40 (2H, m), 2.20 (2H, m), 1.25 (6H, t).

Example 19 2-[5,6-difluoro-2-[[6-methoxy-5-[3-(1-methylpyrrolidin-1-ium-1-yl)propoxy]-1,3-benzothiazol-2-yl]methylcarbamoyl]indan-2-yl]acetate

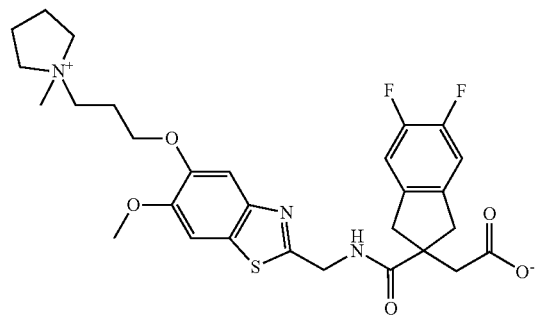 [SMILES: COc1cc2sc(CNC(=O)C3(CC(=O)[O-])Cc4cc(F)c(F)cc4C3)nc2cc1OCCC[N+]1(C)CCCC1]

This was prepared in an analogous manner to Example 18 with the changes that 3-(pyrrolidine-1-yl)propan-1-ol was used in place of 3-diethylamino-1-propanol and 2-[(tert-butoxy)carbonyl]-5,6-difluoro-2,3-dihydro-1H-indene-2-carboxylic acid was used in place of 2-[(tert-butoxy)carbonyl]-2,3-dihydro-1H-indene-2-carboxylic acid. The title compound was isolated as a white solid (45 mg). M/z 574.4 (M+H)+. 1H NMR (400 MHz, d6-DMSO) δ 7.68 (1H, s), 7.55 (1H, s), 7.22 (2H, t), 4.65 (2H, d), 4.15 (2H, t), 3.85 (3H, s), 3.50 (6H, m), 3.40 (2H, d), 3.05 (3H, s), 2.90 (2H, d), 2.30 (2H, m), 2.10 (4H, m).

Example 20

2-[2-[[5-[3-[2-hydroxyethyl(dimethyl)ammonio]propoxy]-6-methoxy-1,3-benzothiazol-2-yl]methylcarbamoyl]indan-2-yl]acetate

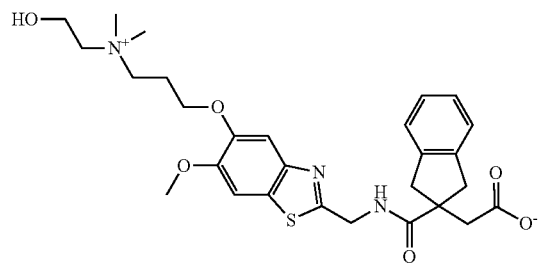 [SMILES: COc1cc2sc(CNC(=O)C3(CC(=O)[O-])Cc4ccccc4C3)nc2cc1OCCC[N+](C)(C)CCO]

a. Tert-butyl N-{[6-methoxy-5-(3-{methyl[2-(oxan-2-yloxy)ethyl]amino}propoxy)-1,3-benzothiazol-2-yl]methyl}carbamate

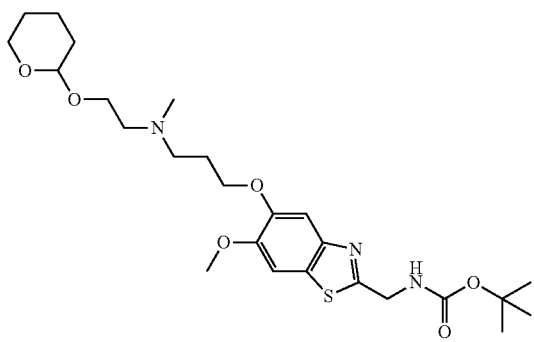 [SMILES: COc1cc2sc(CNC(=O)OC(C)(C)C)nc2cc1OCCCN(C)CCOC1CCCCO1]

This was prepared by the same procedure as for Example (18a) with the change that 3-(methyl(2-((tetrahydro-2H-pyran-2-yl)oxy)ethyl)amino)propan-1-ol was used in place of 3-diethylamino-1-propanol, affording a colourless oil (212 mg, 54%). M/z 510.4 (M+H)+.

b. (3-{[2-({[(Tert-butoxy)carbonyl]amino}methyl)-6-methoxy-1,3-benzothiazol-5-yl]oxy}propyl)dimethyl[2-(oxan-2-yloxy)ethyl]azanium Iodide

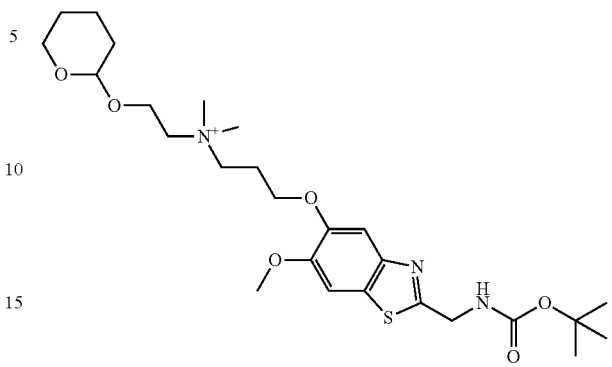

This was prepared from tert-butyl N-{[6-methoxy-5-(3-{methyl[2-(oxan-2-yloxy)ethyl]amino}propoxy)-1,3-benzothiazol-2-yl]methyl}carbamate by the same procedure as for Example (18b) affording a clear oil (201 mg, 74%). M/z 524.4 (M)+.

c. (3-{[2-(Aminomethyl)-6-methoxy-1,3-benzothiazol-5-yl]oxy}propyl)(2-hydroxyethyl)dimethylazanium Chloride Hydrochloride

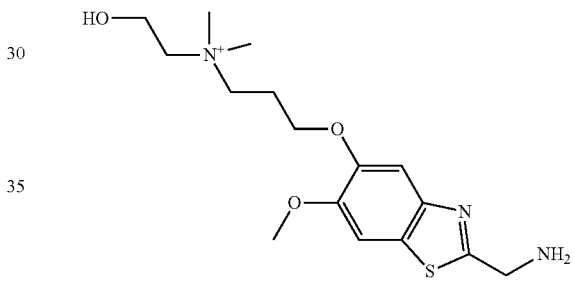

This was prepared from (3-{[2-({[(tert-butoxy)carbonyl]amino}methyl)-6-methoxy-1,3-benzothiazol-5-yl]oxy}propyl)dimethyl[2-(oxan-2-yloxy)ethyl]azanium iodide by the method of Example (18c) with the difference that the reaction time was lengthened to 2 h from 1.5 h, affording an oil in quantitative yield. M/z 340.3 (M)+.

d. 3-[[2-[[[2-(2-tert-butoxy-2-oxo-ethyl)indane-2-carbonyl]amino]methyl]-6-methoxy-1,3-benzothiazol-5-yl]oxy]propyl-(2-hydroxyethyl)-dimethyl-ammonium Chloride

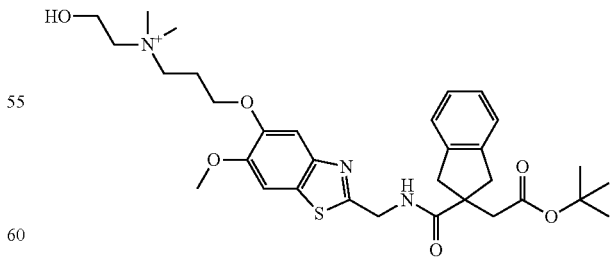

This was prepared from (3-{[2-(aminomethyl)-6-methoxy-1,3-benzothiazol-5-yl]oxy}propyl)(2-hydroxyethyl)dimethylazanium chloride hydrochloride by the method of Example (18d) affording a white solid (68 mg, 69%). M/z 598.4 (M)+ e. 2-[2-[[5-[3-[2-hydroxyethyl(dimethyl)ammonio]propoxy]-6-methoxy-1,3-benzothiazol-2-yl]methylcarbamoyl]indan-2-yl]acetate This was prepared from 3-[[2-[[[2-(2-tert-butoxy-2-oxoethyl)indane-2-carbonyl]amino]methyl]-6-methoxy-1,3-benzothiazol-5-yl]oxy]propyl-(2-hydroxyethyl)-dimethyl-ammonium chloride by the method of Example (18e) affording the title compound as a white solid (40 mg, 68%). M/z 542.4 (M+H)$^+$. $^1$H NMR (400 MHz, d$_6$-DMSO) δ 13.10 (1H, bs), 7.65 (1H, s), 7.50 (1H, s), 7.15 (2H, m), 7.05 (2H, m), 5.50 (1H, bs), 4.60 (2H, d), 4.15 (2H, t), 3.90 (2H, m), 3.85 (3H, s), 3.55 (2H, m), 3.46 (2H, m), 3.35 (2H, d), 3.15 (6H, s), 2.87 (2H, d), 2.40 (2H, m), 2.30 (2H, m).

Example 21 2-[5,6-difluoro-2-[[5-[3-[2-hydroxyethyl(dimethyl)ammonio]propoxy]-6-methoxy-1,3-benzothiazol-2-yl]methylcarbamoyl]indan-2-yl]acetate

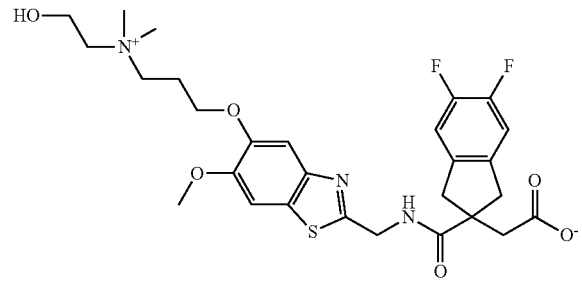 [SMILES: COc1cc2sc(CNC(=O)C3(CC(=O)[O-])Cc4cc(F)c(F)cc4C3)nc2cc1OCCC[N+](C)(C)CCO]

This was prepared in an analogous manner to Example 20 except that 2-[(tert-butoxy)carbonyl]-5,6-difluoro-2,3-dihydro-1H-indene-2-carboxylic acid was used in place of 2-[(tert-butoxy)carbonyl]-2,3-dihydro-1H-indene-2-carboxylic acid. The title compound was isolated as a white solid (35 mg). M/z 578.3 (M+H)$^+$. $^1$H NMR (400 MHz, d$_6$-DMSO) δ 13.00 (1H, bs), 7.65 (1H, s), 7.52 (1H, s), 7.20 (2H, t), 5.50 (1H, bs), 4.60 (2H, d), 4.15 (2H, t), 3.90 (2H, m), 3.85 (3H, s), 3.55 (2H, m), 3.45 (2H, m), 3.35 (2H, d), 3.15 (6H, s), 2.90 (2H, d), 2.40 (2H, m), 2.30 (2H, m).

Example 22 2-[2-[[5-[3-[bis(2-hydroxyethyl)-methyl-ammonio]propoxy]-6-methoxy-1,3-benzothiazol-2-yl]methylcarbamoyl]indan-2-yl]acetate

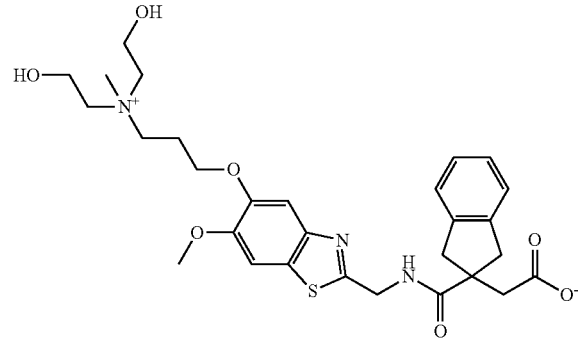 [SMILES: COc1cc2sc(CNC(=O)C3(CC(=O)[O-])Cc4ccccc4C3)nc2cc1OCCC[N+](C)(CCO)CCO]

This was prepared in an analogous manner to Example 20 except that 3-(bis(2-((tetrahydro-2H-pyran-2-yl)oxy)ethyl)amino)propan-1-ol was used in place of 3-(methyl(2-((tetrahydro-2H-pyran-2-yl)oxy)ethyl)amino)propan-1-ol. The title compound was isolated as a white solid (31 mg). M/z 572.4 (M+H)$^+$. $^1$H NMR (400 MHz, d$_6$-DMSO) δ 13.00 (1H, bs), 7.65 (1H, s), 7.50 (1H, s), 7.20 (2H, m), 7.10 (2H, m), 5.50 (2H, bs), 4.60 (2H, d), 4.20 (2H, t), 3.95 (4H, m), 3.85 (3H, s), 3.60 (2H, m), 3.50 (4H, m), 3.40 (2H, d), 3.15 (3H, s), 2.90 (2H, d), 2.20 (2H, m).

Example 23 2-[2-[[5-[3-[bis(2-hydroxyethyl)-methyl-ammonio]propoxy]-6-methoxy-1,3-benzothiazol-2-yl]methylcarbamoyl]-5,6-difluoro-indan-2-yl]acetate

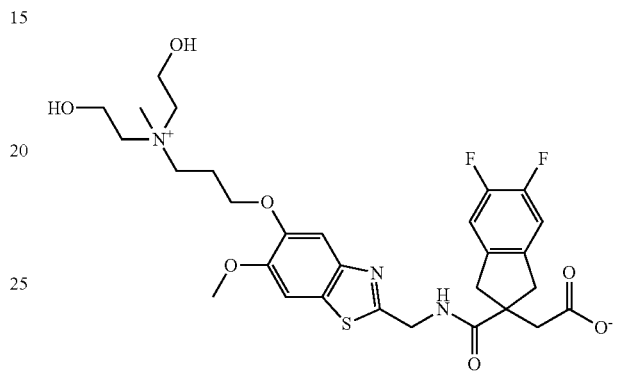

This was prepared in an analogous manner to Example 22 except that 2-[(tert-butoxy)carbonyl]-5,6-difluoro-2,3-dihydro-1H-indene-2-carboxylic acid was used in place of 2-[(tert-butoxy)carbonyl]-2,3-dihydro-1H-indene-2-carboxylic acid. The title compound was isolated as a white solid (10 mg). M/z 608.4 (M+H)$^+$. $^1$H NMR (400 MHz, d$_6$-DMSO) δ 13.00 (1H, bs), 7.65 (1H, s), 7.50 (1H, s), 7.20 (2H, t), 5.40 (2H, bs), 4.60 (2H, d), 4.10 (2H, t), 3.95 (4H, m), 3.85 (3H, s), 3.60 (2H, m), 3.50 (4H, m), 3.40 (2H, d), 3.15 (3H, s), 2.90 (2H, d), 2.20 (2H, m).

Example 24 2-[2-[[5-[2-(4-methylpiperazin-1-yl)-2-oxo-ethoxy]-1,3-benzothiazol-2-yl]methylcarbamoyl]indan-2-yl]acetic Acid

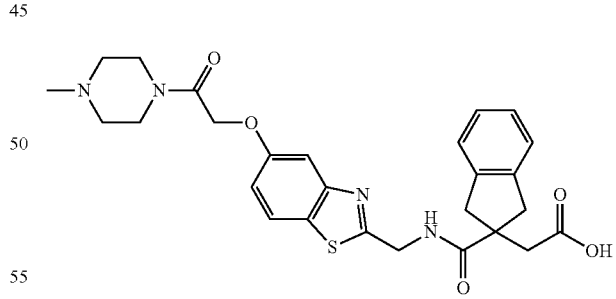

a. 2-hydroxy-1-(4-methylpiperazin-1-yl)ethan-1-one

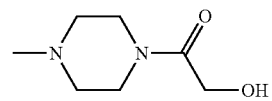

To a stirred solution of 1-methylpiperazine (500 mg, 4.99 mmol) in dioxane (5 mL) was added ethyl 2-hydroxyacetate (520 mg, 4.99 mmol) at room temperature. The reaction mixture was heated at 120° C. for 12 h and evaporated the solvent affording a pale yellow thick mass (200 mg, crude). M/z 159.1 (M+H)⁺.

b. Tert-butyl N-[(5-bromo-1,3-benzothiazol-2-yl)methyl]carbamate

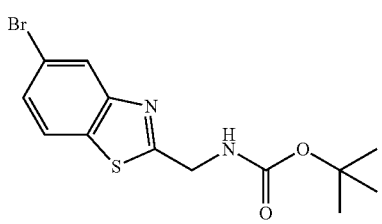 [SMILES: CC(C)(C)OC(=O)NCc1nc2cc(Br)ccc2s1]

CuO (1 g, 12.6 mmol) was added to a stirred solution of 5-bromo-2-iodo-aniline (2.5 g, 8.30 mmol) and tert-butyl N-(2-amino-2-thioxo-ethyl)carbamate (2 g, 10.9 mmol) in DMF (15 mL) at RT and the reaction mixture was purged with argon for 15 min. Then dppf (929 mg, 1.60 mmol) and Pd$_2$(dba)$_3$ (768 mg, 0.8 mmol) were added to the reaction mixture and degassed with argon for further 5 min. The reaction mixture was stirred in a sealed tube at 70° C. for 4 h and filtered through celite pad which was washed with EtOAc (50 mL). The filtrate was washed with water (2×30 mL) and concentrated under reduced pressure. The crude compound was purified by flash chromatography eluting with 20% EtOAc in petroleum ether affording an off white solid (2 g, 71%). M/z 343.0 (M+H)⁺.

c. (5-bromo-1,3-benzothiazol-2-yl)methanamine Hydrochloride

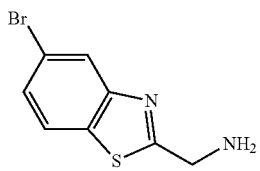 [SMILES: NCc1nc2cc(Br)ccc2s1]

4N HCl in dioxane (30 mL) was added to a solution of tert-butyl N-[(5-bromo-1,3-benzothiazol-2-yl)methyl]carbamate (3 g, 8.7 mmol) in dioxane (50 mL) at 0° C. The reaction mixture was stirred at RT for 4 h and concentrated under reduced pressure. The crude compound was triturated with n-pentane (20 mL) and Et$_2$O (20 mL) affording a pale yellow solid (2.2 g, 90%). M/z 243.0 (M)⁺.

d. tert-butyl 2-[2-[(5-bromo-1,3-benzothiazol-2-yl)methylcarbamoyl]indan-2-yl]acetate

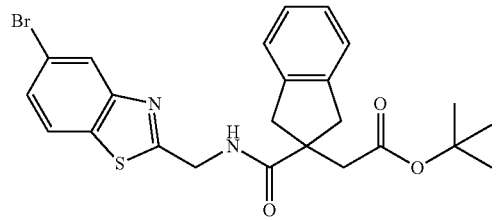 [SMILES: CC(C)(C)OC(=O)CC1(C(=O)NCc2nc3cc(Br)ccc3s2)Cc2ccccc2C1]

Et$_3$N (1.5 mL, 10.8 mmol) was added to a stirred solution of (5-bromo-1,3-benzothiazol-2-yl)methanamine hydrochloride (800 mg, 2.8 mmol) in DMF (10 mL) at RT and stirred for 15 min. Then 2-(2-tert-butoxy-2-oxo-ethyl)indane-2-carboxylic acid (1 g, 3.6 mmol), EDC.HCl (833 mg, 4.3 mmol) and HOBt (684 mg, 5.0 mmol) were added. The reaction mixture was stirred at RT for 16 h, diluted with ice cold water (100 mL) and extracted with EtOAc (2×50 mL). The organic layer was washed with brine solution, dried over Na$_2$SO$_4$ and concentrated under reduced pressure. The crude compound was purified by flash chromatography eluting with 25% EtOAc in petroleum ether affording an off white solid (1 g, 56%). M/z 501.1 (M+H)⁺.

e. Tert-butyl 2-[2-[[5-(4,4,5,5-tetramethyl-1,3,2-dioxaborolan-2-yl)-1,3-benzothiazol-2-yl]methylcarbamoyl]indan-2-yl]acetate

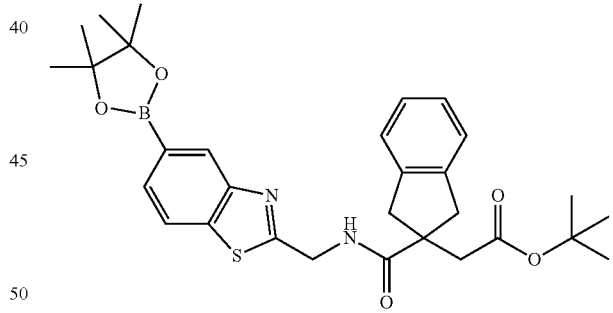

To a solution of tert-butyl 2-[2-[(5-bromo-1,3-benzothiazol-2-yl)methylcarbamoyl]indan-2-yl]acetate (1.5 g, 3.0 mmol) in dioxane (20 mL) was added potassium acetate (588 mg, 6.0 mmol) and Bpin (838 mg, 3.3 mmol) at RT and the reaction mixture was purged with argon for 15 min. Then PdCl$_2$(dppf).DCM (171 mg, 0.21 mmol) was added to the reaction mixture and purged with argon for further 5 min. The reaction mixture was stirred in sealed tube at 90° C. for 4 h. The reaction mixture was filtered through celite pad and washed the pad with EtOAc (50 mL). The organic extracts were washed with water (2×50 mL) and brine, then dried over sodium sulphate, filtered and the solvent removed to give crude product (1.6 g, crude) as a brown semi solid. Mixture of boronic acid M/z 467.2 (M+H)⁺ and boronate ester M/z 549.2 (M+H)⁺.

f. [2-[[[2-(2-tert-butoxy-2-oxo-ethyl)indane-2-carbonyl]amino]methyl]-1,3-benzothiazol-5-yl]boronic Acid

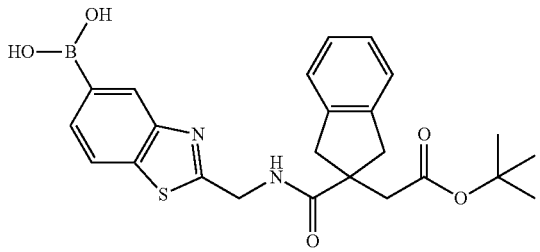 [SMILES: CC(C)(C)OC(=O)CC1(C(=O)NCc2nc3cc(B(O)O)ccc3s2)Cc2ccccc2C1]

To a solution of tert-butyl 2-[2-[[5-(4,4,5,5-tetramethyl-1,3,2-dioxaborolan-2-yl)-1,3-benzothiazol-2-yl]methylcarbamoyl]indan-2-yl]acetate (1.6 g, 2.9 mmol) in THF:H₂O (4:1, 20 mL) was added sodium periodate (1.9 g, 8.7 mmol) at RT and stirred for 30 min. Then 1N HCl (2 mL, 2.0 mmol) was added to the reaction mixture at RT and stirred at RT for 16 h. The reaction mixture was diluted with water and extracted with EtOAc. The organic extracts were washed with water and brine, then dried over sodium sulphate, filtered and the solvent removed. The crude compound was purified by column chromatography (100-200 silica gel, gradient 10% MeOH/DCM) to yield the product (900 mg, 66%) as a yellow solid. M/z 467.2 (M+H)⁺.

g. Tert-butyl 2-(2-(((5-(2-(4-methylpiperazin-1-yl)-2-oxoethoxy)benzo[d]thiazol-2-yl)methyl)carbamoyl)-2,3-dihydro-1H-inden-2-yl)acetate

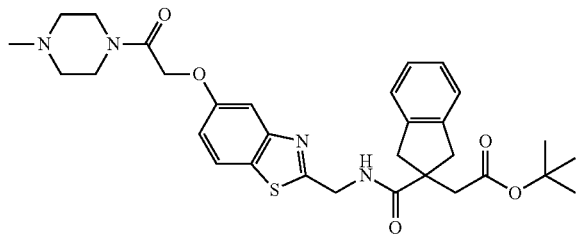 [SMILES: CN1CCN(C(=O)COc2ccc3sc(CNC(=O)C4(CC(=O)OC(C)(C)C)Cc5ccccc5C4)nc3c2)CC1]

To a solution of [2-[[[2-(2-tert-butoxy-2-oxo-ethyl)indane-2-carbonyl]amino]methyl]-1,3-benzothiazol-5-yl]boronic acid (300 mg, 0.64 mmol) in DCM (10 mL) was added Cu(OAc)₂ (175 mg, 0.96 mmol), triethylamine (0.2 mL, 1.28 mmol) and molecular sieves (0.5 g) at room temperature. The reaction mixture was stirred for 10 minutes, then added 2-hydroxy-1-(4-methylpiperazin-1-yl)ethan-1-one (153 mg, 0.96 mmol) and stirred at room temperature under air for 16 h. The reaction mixture was filtered through celite pad, washed the pad with dichloromethane and filtrate was evaporated to get the crude compound. The crude was chromatographed on silica eluting with 3% MeOH in DCM affording tert-butyl 2-(2-(((5-(2-(4-methylpiperazin-1-yl)-2-oxoethoxy)benzo[d]thiazol-2-yl)methyl)carbamoyl)-2,3-dihydro-1H-inden-2-yl)acetate as a pale brown solid (60 mg, 16%). M/z 579.3 (M+H)⁺.

h. 2-[2-[[5-[2-(4-methylpiperazin-1-yl)-2-oxo-ethoxy]-1,3-benzothiazol-2-yl]methylcarbamoyl]indan-2-yl]acetic Acid A solution of tert-butyl 2-(2-(((5-(2-(4-methylpiperazin-1-yl)-2-oxoethoxy)benzo[d]thiazol-2-yl)methyl)carbam-oyl)-2,3-dihydro-1H-inden-2-yl)acetate (50 mg, 0.086 mmol) in DCM (4 mL) was treated with TFA (0.5 mL) at room temperature for 2 h. The mixture was evaporated and the residue was triturated with diethyl ether (6 mL). The crude compound was purified by preparative HPLC [SYMMETRY-C8 (3000*19), 7 u, Mobile phase: A: 0.1% Formic Acid in H₂O, B: MeCN] and freeze dried affording an off white solid (15 mg, 34%). M/z 523.2 (M+H)⁺. ¹H NMR (500 MHz, MeOD): δ 7.79 (1H, d, J=9 Hz), 7.44 (1H, s), 7.23-7.21 (2H, m), 7.16-7.15 (2H, m), 7.13 (1H, d, J=9 Hz), 4.94 (2H, s), 4.75 (2H, s), 3.85-3.75 (4H, bs), 3.52 (2H, d, J=16.5 Hz), 3.16-3.07 (4H, bs), 3.09 (2H, d, J=16.5 Hz), 2.82 (2H, s), 2.78 (3H, s).

Example 25 2-[2-[[5-[2-(4-methylpiperazin-1-yl)ethoxy]-1,3-benzothiazol-2-yl]methylcarbamoyl]indan-2-yl]acetic Acid

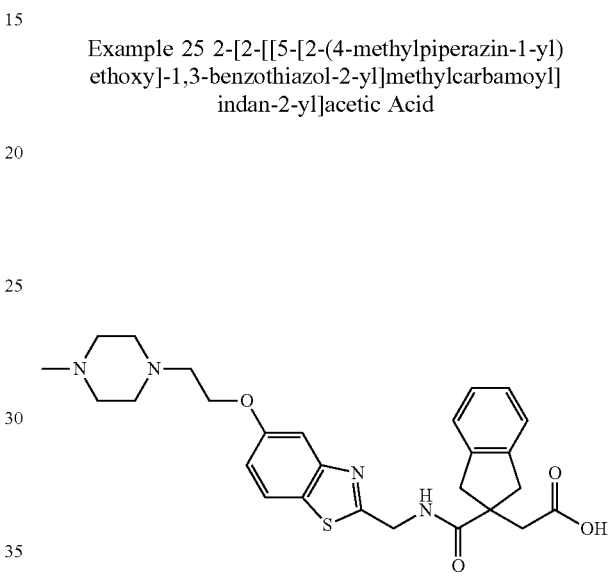

This was prepared in an analogous manner to Example 24 using 2-(4-methylpiperazin-1-yl)ethanol in step-d. The title compound was isolated as a white solid. M/z 509.2 (M+H)⁺. ¹H ¹H NMR (500 MHz, DMSO-d₆): δ 12.16 (1H, bs), 8.72 (1H, t, J=6 Hz), 7.88 (1H, d, J=9 Hz), 7.48 (1H, s), 7.22-7.21 (2H, m), 7.17-7.14 (2H, m), 7.04 (1H, d, J=9 Hz), 4.62 (2H, d, J=6 Hz), 4.19 (2H, bs), 3.55-3.30 (4H, bs), 3.22-3.10 (4H, m), 3.10-3.00 (2H, m), 2.99 (2H, d, J=16.5 Hz), 2.98-2.85 (2H, m), 2.80-2.70 (2H, m), 2.74 (3H, m).

Example 26 2-[2-[[6-[3-(dimethylamino)azetidine-1-carbonyl]-1,3-benzothiazol-2-yl]methylcarbamoyl]indan-2-yl]acetic Acid

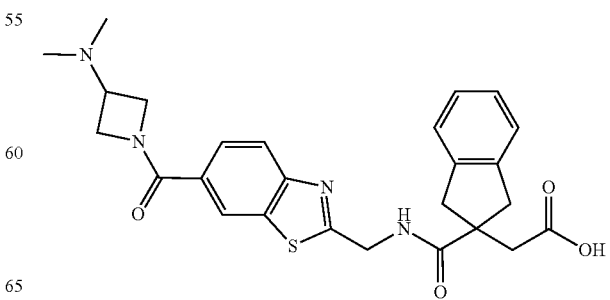

a. Methyl 2-[(tert-butoxycarbonylamino)methyl]-1,3-benzothiazole-6-carboxylate

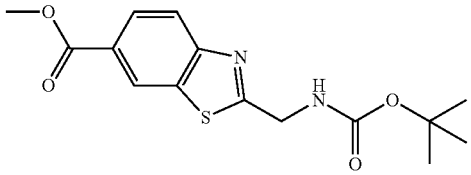 [SMILES: COC(=O)c1ccc2nc(CNC(=O)OC(C)(C)C)sc2c1]

To a stirred solution of methyl 4-amino-3-iodobenzoate (6 g, 21.6 mmol) in acetonitrile (60 mL) was added tert-butyl (2-amino-2-thioxoethyl)carbamate (4.9 g, 25.9 mmol) and CuO (2.6 g, 32.4 mmol) at room temperature. The reaction mixture was purged with argon for 15 minutes, then dppf (2.4 g, 4.33 mmol) and Pd$_2$(dba)$_3$ (2 g, 2.16 mmol) was added to the reaction mixture. The reaction mixture was purged with argon for further 5 minutes and heated in a sealed tube at 80° C. for 16 h.

The reaction mixture was filtered through celite pad, washed the pad with DCM (60 mL) and filtrate was evaporated. The crude was chromatographed on silica eluting with 20-30% EtOAc in petroleum ether affording a yellow solid (4 g, 57%). M/z 323.1 (M+H)$^+$.

b. 2-[(tert-butoxycarbonylamino)methyl]-1,3-benzothiazole-6-carboxylic Acid

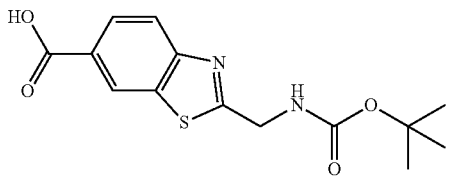 [SMILES: CC(C)(C)OC(=O)NCc1nc2ccc(C(=O)O)cc2s1]

A solution of methyl 2-(((tert-butoxycarbonyl)amino)methyl)benzo[d]thiazole-6-carboxylate (2.5 g, 7.76 mmol) in THF/water (1:1, 100 mL) was added LiOH.H$_2$O (652 mg, 15.5 mmol) at room temperature and stirred for 6 h. The reaction mixture was evaporated, resulting residue was diluted with water (10 mL) and adjusted the pH to ~7 with saturated citric acid. The product was extracted with 10% MeOH in DCM (2×50 mL) and evaporated affording a yellow solid (2 g, 83%). M/z 307.0 (M−H)$^+$.

c. Tert-butyl N-[[6-[3-(dimethylamino)azetidine-1-carbonyl]-1,3-benzothiazol-2-yl]methyl]carbamate

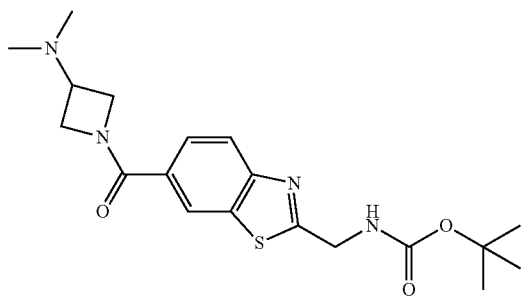 [SMILES: CN(C)C1CN(C(=O)c2ccc3nc(CNC(=O)OC(C)(C)C)sc3c2)C1]

A solution of 2-(((tert-butoxycarbonyl)amino)methyl)benzo[d]thiazole-6-carboxylic acid (500 mg, 1.62 mmol) in DMF (5 mL) was added N,N-dimethylazetidin-3-amine hydrochloride (281 mg, 1.62 mmol) and Et$_3$N (0.7 mL, 4.87 mmol) at room temperature and stirred for 10 minutes. Then T3P (750 mg, 2.43 mmol) was added and stirred for 12 h. The reaction mixture was diluted with cold water (10 mL), extracted with EtOAc (2×25 mL) and the organic layer was evaporated affording a pale yellow solid (525 mg, crude). M/z 391.2 (M+H)$^+$.

d. (2-(aminomethyl)benzo[d]thiazol-6-yl)(3-(dimethylamino)azetidin-1-yl)methanone Hydrochloride

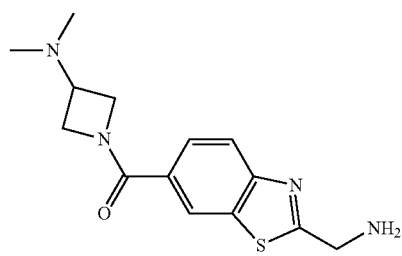 [SMILES: CN(C)C1CN(C(=O)c2ccc3nc(CN)sc3c2)C1]

A solution of tert-butyl ((6-(3-(dimethylamino)azetidine-1-carbonyl)benzo[d]thiazol-2-yl)methyl)carbamate (520 mg, 1.33 mmol) in dioxane (5 mL) was added 4M HCl in dioxane (4 mL) at room temperature and stirred for 3 h. The reaction mixture evaporated and resulting residue was triturated with diethyl ether (15 mL) affording a yellow solid (500 mg, crude). M/z 291.0 (M+H)$^+$.

e. Tert-butyl 2-[2-[[6-[3-(dimethylamino)azetidine-1-carbonyl]-1,3-benzothiazol-2-yl]methylcarbamoyl]indan-2-yl]acetate

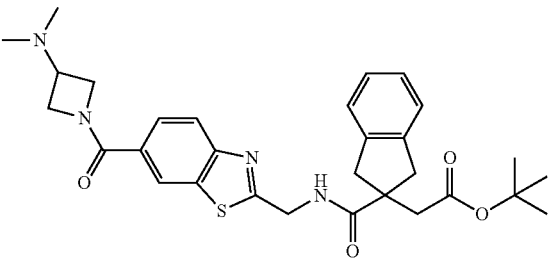 [SMILES: CN(C)C1CN(C(=O)c2ccc3nc(CNC(=O)C4(CC(=O)OC(C)(C)C)Cc5ccccc5C4)sc3c2)C1]

A solution of (2-(aminomethyl)benzo[d]thiazol-6-yl)(3-(dimethylamino)azetidin-1-yl)methanone hydrochloride (220 mg, 0.67 mmol) in DMF (4 mL) was added Et$_3$N (0.5 mL, 3.37 mmol) at room temperature and stirred for 10 minutes. Then 2-(2-(tert-butoxy)-2-oxoethyl)-2,3-dihydro-1H-indene-2-carboxylic acid (208 mg, 0.74 mmol) and T3P (660 mg, 1.03 mmol) was added and stirred for 12 h. The reaction mixture was diluted with cold water (10 mL), extracted with EtOAc (2×30 mL) and the organic layer was evaporated to give crude compound. The crude was chromatographed on silica eluting with 2% MeOH in DCM affording a brown solid (120 mg, 33%). M/z 549.3 (M+H)$^+$.

f. 2-[2-[[6-[3-(dimethylamino)azetidine-1-carbonyl]-1,3-benzothiazol-2-yl]methylcarbamoyl]indan-2-yl]acetic Acid A solution of tert-butyl 2-(2-(((6-(3-(dimethylamino)azetidine-1-carbonyl)benzo[d]thiazol-2-yl)methyl)carbamoyl)-

2,3-dihydro-1H-inden-2-yl)acetate (110 mg, 0.20 mmol) in DCM (5 mL) was treated with TFA (2 mL) at room temperature for 4 h. The mixture was evaporated and the residue was triturated with diethyl ether (10 mL). The crude compound was purified by preparative HPLC [YMC-TRIART-C18 (150*25), 10 u, Mobile phase: A: 0.1% Formic Acid in H₂O, B: MeCN] and freeze dried affording the title product as an off white solid (53 mg, 54%). M/z 493.2 (M+H)⁺. ¹H NMR (500 MHz, DMSO-d₆): δ 12.16 (1H, bs), 8.79 (1H, t, J=6 Hz), 8.35 (1H, d, J=1.5 Hz), 8.00 (1H, d, J=8.5 Hz), 7.75 (1H, dd, J=8.5 Hz, J=1.5 Hz), 7.23-7.21 (2H, m), 7.16-7.14 (2H, m), 4.69 (2H, d, J=6 Hz), 4.62-4.58 (1H, m), 4.48-4.42 (1H, m), 4.31-4.19 (2H, m), 4.15-4.05 (1H, m), 3.46 (2H, d, J=16.5 Hz), 3.01 (2H, d, J=16.5 Hz), 2.85-2.65 (8H, bs).

Example 27 2-[2-[[5-(4-methylpiperazine-1-carbonyl)-1,3-benzothiazol-2-yl]methylcarbamoyl]indan-2-yl]acetic Acid

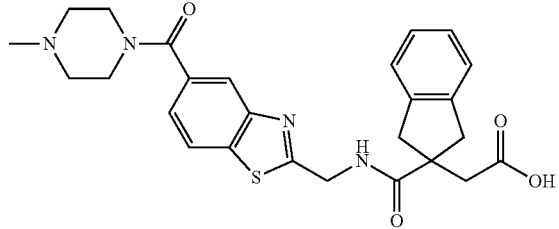 [SMILES: CN1CCN(C(=O)c2ccc3sc(CNC(=O)C4(CC(=O)O)Cc5ccccc5C4)nc3c2)CC1]

This was prepared in an analogous manner to Example 26 starting from methyl 3-amino-4-iodobenzoate in step-a and using 1-methylpiperazine in step-c. The title compound was isolated as a white solid. M/z 493.2 (M+H)⁺. ¹H NMR (500 MHz, DMSO-d₆): δ 12.15 (1H, bs), 9.80 (1H, bs), 8.79 (1H, t, J=5.5 Hz), 8.13 (1H, d, J=8.5 Hz), 8.00 (1H, s), 7.46 (1H, d, J=8.5 Hz), 7.23-7.21 (2H, m), 7.15-7.13 (2H, m), 4.67 (2H, d, J=5.5 Hz), 3.47 (2H, d, J=16 Hz), 3.18-3.01 (8H, m), 2.99 (2H, d, J=16 Hz), 2.79 (2H, s), 2.75 (3H, s).

Example 28 2-[2-[[5-[2-(dimethylamino)ethylcarbamoyl]-1,3-benzothiazol-2-yl]methylcarbamoyl]indan-2-yl]acetic Acid

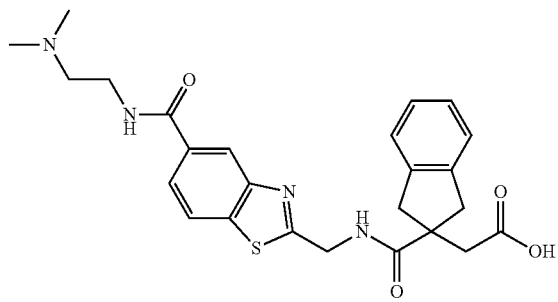 [SMILES: CN(C)CCNC(=O)c1ccc2sc(CNC(=O)C3(CC(=O)O)Cc4ccccc4C3)nc2c1]

This was prepared in an analogous manner to Example 26 starting from methyl 3-amino-4-iodobenzoate in step-a and using N',N'-dimethylethane-1,2-diamine in step-c. The title compound was isolated as a white solid. M/z 481.2 (M+H)⁺. ¹H NMR (500 MHz, DMSO-d₆): δ 11.42 (1H, bs), 8.79 (1H, t, J=5.5 Hz), 8.68 (1H, t, J=5 Hz), 8.40 (1H, s), 8.11 (1H, d, J=8.5 Hz), 7.88 (1H, dd, J=8.5 Hz, J=1.5 Hz), 7.23-7.21 (2H, m), 7.15-7.13 (2H, m), 4.68 (2H, d, J=6.0 Hz), 3.51-3.48 (2H, m), 3.46 (2H, d, J=16.5 Hz), 3.00 (2H, d, J=16.5 Hz), 2.88-2.82 (2H, bs), 2.75 (2H, s), 2.55-2.50 (6H, bs).

Example 29 2-[2-[[6-(4-methylpiperazine-1-carbonyl)-1,3-benzothiazol-2-yl]methylcarbamoyl]indan-2-yl]acetic Acid

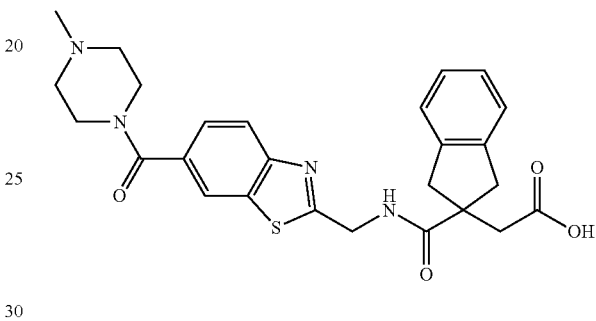

This was prepared in an analogous manner to Example 26 starting from methyl 4-amino-3-iodobenzoate in step-a and using 1-methylpiperazine in step-c. The title compound was isolated as a white solid. M/z 493.2 (M+H)⁺. ¹H NMR (500 MHz, MeOD): δ 8.07 (1H, d, J=1.0 Hz), 7.99 (1H, d, J=8.5 Hz), 7.57 (1H, dd, J=8.5 Hz, J=1 Hz), 7.23-7.21 (2H, m), 7.16-7.15 (2H, m), 4.79 (2H, s), 3.88-3.75 (4H, m), 3.54 (2H, d, J=16 Hz), 3.20-3.15 (4H, m), 3.10 (2H, d, J=16 Hz), 2.83 (2H, s), 2.81 (3H, s).

Example 30 2-[2-[[6-[2-(dimethylamino)ethylcarbamoyl]-1,3-benzothiazol-2-yl]methylcarbamoyl]indan-2-yl]acetic Acid

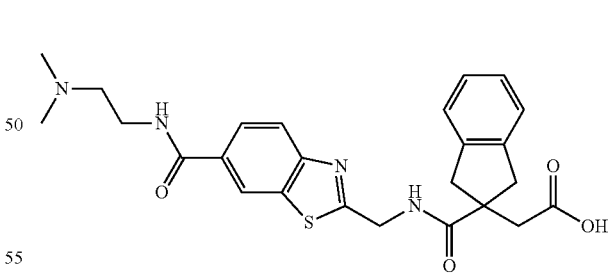

This was prepared in an analogous manner to Example 26 starting from methyl 4-amino-3-iodobenzoate in step-a and using N',N'-dimethylethane-1,2-diamine in step-c. The title compound was isolated as a white solid. M/z 481.2 (M+H)⁺. ¹H NMR (500 MHz, DMSO-d₆): δ 12.15 (1H, bs), 8.77 (2H, t, J=5.5 Hz), 8.51 (1H, s), 8.02 (1H, d, J=8.5 Hz), 7.96 (1H, dd, J=8.5 Hz, J=1.5 Hz), 7.23-7.21 (2H, m), 7.15-7.13 (2H, m), 4.68 (2H, d, J=6.0 Hz), 3.63-3.60 (2H, m), 3.48 (2H, d, J=16.5 Hz), 3.26-3.20 (2H, m), 3.00 (2H, d, J=16.5 Hz), 2.83 (6H, s), 2.76 (2H, s).

Example 31 2-[2-[[5-[4-[3-(dimethylamino)propyl]piperazine-1-carbonyl]-1,3-benzothiazol-2-yl]methylcarbamoyl]indan-2-yl]acetic Acid

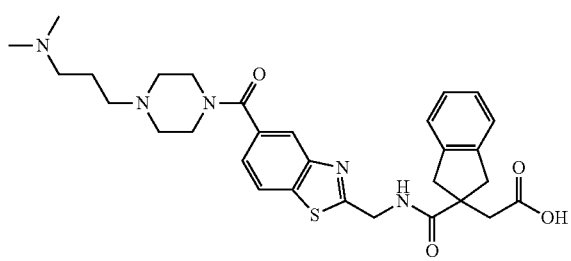 [SMILES: CN(C)CCCN1CCN(C(=O)c2ccc3sc(CNC(=O)C4(CC(=O)O)Cc5ccccc5C4)nc3c2)CC1]

This was prepared in an analogous manner to Example 26 starting from methyl 3-amino-4-iodobenzoate in step-a and using N,N-dimethyl-3-piperazin-1-yl-propan-1-amine in step-c. The title compound was isolated as a white solid. M/z 564.2 (M+H)$^+$. $^1$H NMR (500 MHz, DMSO-d$_6$): δ 9.07 (1H, bs), 8.10 (1H, d, J=8.5 Hz), 7.89 (1H, s), 7.39 (1H, d, J=8.5 Hz), 7.22-7.20 (2H, m), 7.14-7.13 (2H, m), 4.67 (2H, d, J=5.5 Hz), 3.64-3.62 (2H, m), 3.46 (2H, d, J=16 Hz), 3.25-3.15 (2H, bs), 3.01 (2H, d, J=16 Hz), 2.72 (2H, s), 2.48-2.25 (8H, bs) 2.18 (6H, s), 1.58-1.55 (2H, m).

Example 32 2-[2-[[5-[3-(dimethylamino)azetidine-1-carbonyl]-1,3-benzothiazol-2-yl]methylcarbamoyl]indan-2-yl]acetic Acid

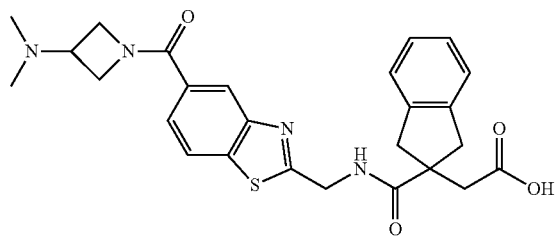 [SMILES: CN(C)C1CN(C(=O)c2ccc3sc(CNC(=O)C4(CC(=O)O)Cc5ccccc5C4)nc3c2)C1]

This was prepared in an analogous manner to Example 26 starting from methyl 3-amino-4-iodobenzoate in step-a. The title compound was isolated as a white solid. M/z 493.2 (M+H)$^+$. $^1$H NMR (500 MHz, DMSO-d$_6$): δ 12.05 (1H, bs), 8.94 (1H, bs), 8.11 (1H, s), 8.10 (1H, d, J=8.0 Hz), 7.65 (1H, dd, J=8 Hz, J=1 Hz), 7.22-7.20 (2H, m), 7.14-7.13 (2H, m), 4.67 (2H, d, J=5.5 Hz), 4.34-4.31 (1H, m), 4.13-4.06 (2H, m), 3.86-3.83 (1H, m), 3.46 (2H, d, J=16 Hz), 3.10-3.05 (1H, m), 2.99 (2H, d, J=16 Hz), 2.73 (2H, s), 2.08 (6H, s).

Example 33 2-[2-[[6-methoxy-5-(4-methylpiperazine-1-carbonyl)-1,3-benzothiazol-2-yl]methylcarbamoyl]indan-2-yl]acetic Acid

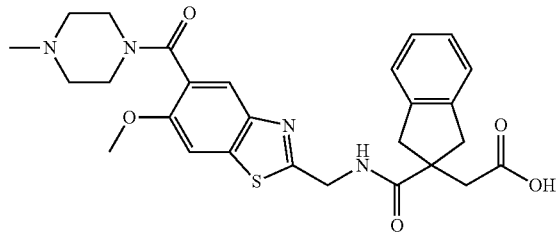 [SMILES: COc1cc2sc(CNC(=O)C3(CC(=O)O)Cc4ccccc4C3)nc2cc1C(=O)N1CCN(C)CC1]

a. Methyl 4-iodo-2-methoxy-5-nitrobenzoate

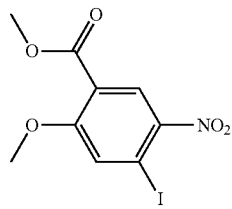 [SMILES: COC(=O)c1cc([N+](=O)[O-])c(I)cc1OC]

A solution of commercially-available methyl 4-iodo-2-methoxybenzoate (1.05 g, 3.6 mmol) in concentrated sulfuric acid (1.6 ml) was treated at 0° C. with a mixture of concentrated nitric acid/concentrated sulfuric acid (0.6 mL/1 mL). The mixture was stirred at room temperature for 5 h then added to ice/water and extracted twice with ethyl acetate. The combined ethyl acetate extracts were washed with saturated aqueous sodium chloride solution. The organic phase was dried (MgSO$_4$) and evaporated to afford a yellow solid (1.03 g, 85%) that was used without purification. M/z 338.4 (M+H)$^+$.

b. Methyl 5-amino-4-iodo-2-methoxybenzoate

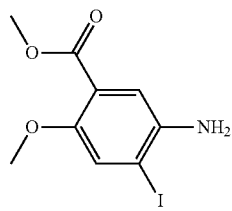

A mixture of methyl 4-iodo-2-methoxy-5-nitrobenzoate (600 mg, 1.8 mmol), iron powder (840 mg, 15 mmol) and methanol (9 mL) was treated with aqueous hydrochloric acid (0.2M; 9 mL, 1.8 mmol) then heated to reflux for 3 h. The mixture was allowed to cool to room temperature then filtered through celite and evaporated. The residue was dissolved in ethyl acetate and washed with saturated aqueous sodium bicarbonate solution, dried (MgSO$_4$) and evaporated to afford a yellow solid. This was triturated with methanol and filtered, affording recovered starting material (183 mg). The filtrate was evaporated and the residue c. Methyl 2-({[(tert-butoxy)carbonyl]amino}methyl)-6-methoxy-1,3-benzothiazole-5-carboxylate

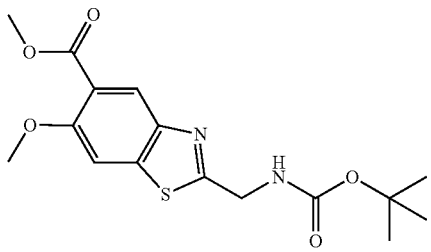 [SMILES: COC(=O)c1cc2nc(CNC(=O)OC(C)(C)C)sc2cc1OC]

A solution of methyl 5-amino-4-iodo-2-methoxybenzoate (132 mg, 0.43 mmol) in in ACN (3 mL) was treated with tert-butyl (2-amino-2-thioxoethyl)carbamate (100 mg, 0.52 mmol), calcium oxide (50 mg, 0.52 mmol), tris(dibenzylideneacetone)dipalladium(0) (38 mg, 0.41 mmol) and dppf (90 mg, 0.16 mmol) then degassed and flushed with argon. The mixture was heated at 65° C. in a sealed vial for 5 h then cooled, diluted with ethyl acetate and washed with 10% aqueous citric acid solution then saturated aqueous sodium chloride solution. The organic extract was dried (MgSO₄) and evaporated. The residue was chromatographed on silica eluting with 0-100% ethyl acetate in hexane affording an oil (97 mg, 64%). M/z 353.3 (M+H)⁺.

d. 2-({[(Tert-butoxy)carbonyl]amino}methyl)-6-methoxy-1,3-benzothiazole-5-carboxylic Acid

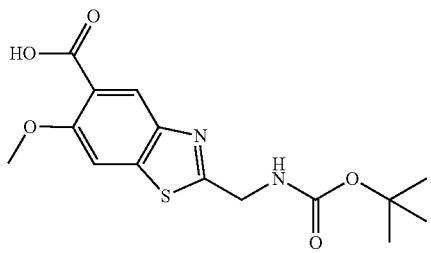 [SMILES: COc1cc2sc(CNC(=O)OC(C)(C)C)nc2cc1C(=O)O]

A solution of methyl 2-({[(tert-butoxy)carbonyl]amino}methyl)-6-methoxy-1,3-benzothiazole-5-carboxylate (96 mg, 0.27 mmol) in THF (3 mL) was treated with aqueous lithium hydroxide solution (1M; 0.5 mL, 0.5 mmol). After 16 h the mixture was reduced in volume by evaporation and acidified to pH 4 with aqueous hydrochloric acid (1M) then extracted with DCM. The DCM extract was washed with water, saturated aqueous sodium chloride solution, dried (MgSO₄) and evaporated to give a brown foam (55 mg, 60%). M/z 283.3 (M–t–Bu)⁺.

e. Tert-butyl N-{[6-methoxy-5-(4-methylpiperazine-1-carbonyl)-1,3-benzothiazol-2-yl]methyl}carbamate

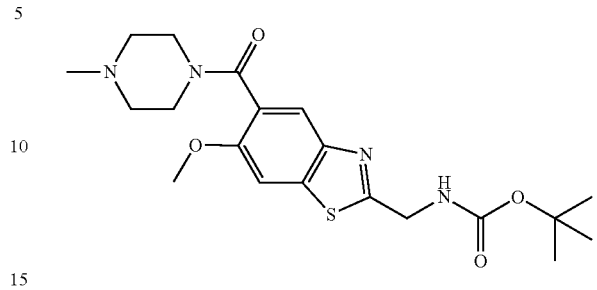

A solution of 2-({[(tert-butoxy)carbonyl]amino}methyl)-6-methoxy-1,3-benzothiazole-5-carboxylic acid (55 mg, 0.16 mmol), 1-methylpiperazine (20 mg, 0.2 mmol), DIPEA (63 mg, 0.5 mmol) in DCM (4 mL) was treated with HATU (74 mg, 0.2 mmol). After 4 h the mixture was diluted with DCM and washed with water then saturated aqueous sodium chloride solution, dried (MgSO₄) and evaporated to give a brown foam (135 mg). This was chromatographed on silica eluting with 0-10% methanol in DCM affording an oil (41 mg, 60%). M/z 421.2 (M+H)⁺.

f. [6-Methoxy-5-(4-methylpiperazine-1-carbonyl)-1,3-benzothiazol-2-yl]methanamine

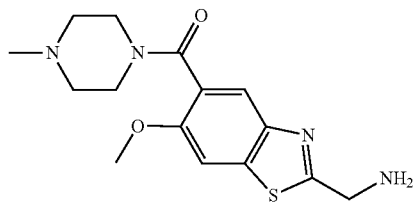 [SMILES: COc1cc2sc(CN)nc2cc1C(=O)N1CCN(C)CC1]

A solution of tert-butyl N-{[6-methoxy-5-(4-methylpiperazine-1-carbonyl)-1,3-benzothiazol-2-yl]methyl}carbamate (41 mg, 0.01 mmol) in DCM (1 mL) was treated with TFA (0.5 mL). After 3 h the mixture was evaporated and the residue purified by chromatography on an SCX cartridge eluting with 2M ammonia in methanol affording a yellow oil (21 mg, 66%). M/z 321.2 (M+H)⁺.

g. Tert-butyl 2-[2-[[6-methoxy-5-(4-methylpiperazine-1-carbonyl)-1,3-benzothiazol-2-yl]methylcarbamoyl]indan-2-yl]acetate

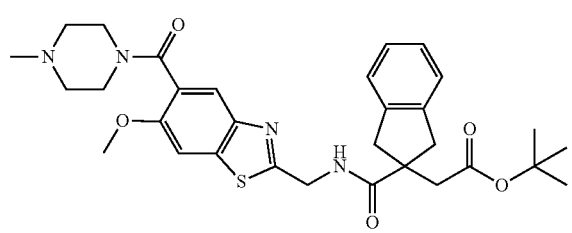 [SMILES: COc1cc2sc(CNC(=O)C3(CC(=O)OC(C)(C)C)Cc4ccccc4C3)nc2cc1C(=O)N1CCN(C)CC1]

A solution of [6-methoxy-5-(4-methylpiperazine-1-carbonyl)-1,3-benzothiazol-2-yl]methanamine (21 mg, 0.07 mmol), 2-(2-(tert-butoxy)-2-oxoethyl)-2,3-dihydro-1H-indene-2-carboxylic acid (22 mg, 0.08 mmol), DIPEA (26 mg, 0.2 mmol) in DCM (3 mL) was treated with HATU (26 mg, 0.07 mmol). After 16 h the mixture was diluted with DCM and washed with water then saturated aqueous sodium chloride solution, dried (MgSO$_4$) and evaporated to give a yellow oil. This was chromatographed on silica eluting with 0-10% methanol in DCM affording an oil (32 mg, 84%). M/z 579.4 (M+H)$^+$.

h. 2-[2-[[6-methoxy-5-(4-methylpiperazine-1-carbonyl)-1,3-benzothiazol-2-yl]methylcarbamoyl]indan-2-yl]acetic Acid A solution of tert-butyl 2-[2-[[6-methoxy-5-(4-methylpiperazine-1-carbonyl)-1,3-benzothiazol-2-yl]methylcarbamoyl]indan-2-yl]acetate (32 mg, 0.05 mmol) in DCM (2 mL) was treated with TFA (0.25 mL). After 2 h the mixture was evaporated. The residue as purified by MDAP and product-containing fractions were freeze-dried to afford the title compound as white solid (20 mg, 69%). M/z 523.1 (M+H)$^+$. $^1$H NMR (400 MHz, d$_6$-DMSO) δ 12.20 (1H, bs), 8.80 (1H, bs), 7.95 (1H, s), 7.75 (1H, s), 7.22 (1H, m), 7.15 (2H, m), 5.40 (2H, bs), 4.60 (2H, m), 3.85 (3H, s), 3.50 (2H, d), 3.45-3.20 (8H, m), 3.15 (3H, s), 2.90 (2H, d).

Example 34 2-[5,6-difluoro-2-[[6-methoxy-5-(4-methylpiperazine-1-carbonyl)-1,3-benzothiazol-2-yl]methylcarbamoyl]indan-2-yl]acetic Acid

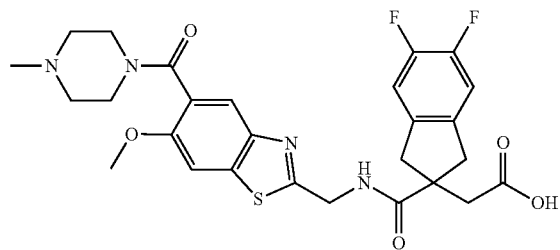 [SMILES: COc1cc2sc(CNC(=O)C3(CC(=O)O)Cc4cc(F)c(F)cc4C3)nc2cc1C(=O)N1CCN(C)CC1]

This was prepared in an analogous manner to Example 33 except that 2-[(tert-butoxy)carbonyl]-5,6-difluoro-2,3-dihydro-1H-indene-2-carboxylic acid was used in place of 2-[(tert-butoxy)carbonyl]-2,3-dihydro-1H-indene-2-carboxylic acid. The title compound was isolated as a white solid (35 mg). M/z 573.2 (M+H)$^+$. $^1$H NMR (400 MHz, d$_6$-DMSO) δ 12.50 (1H, bs), 8.80 (1H, bs), 7.75 (1H, s), 7.70 (1H, s), 7.25 (2H, t), 4.60 (2H, m), 3.85 (3H, s), 3.45 (2H, d), 3.15 (3H, s), 3.00 (2H, d).

Example 35 2-[2-[[5-(4,4-dimethylpiperazin-4-ium-1-carbonyl)-6-methoxy-1,3-benzothiazol-2-yl]methylcarbamoyl]-5,6-difluoro-indan-2-yl]acetate

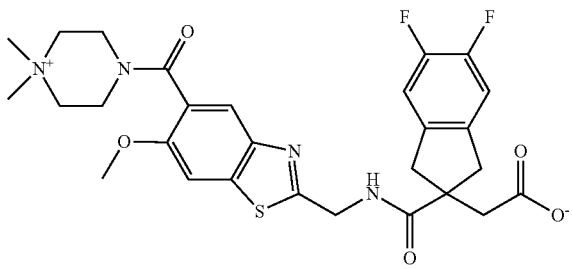 [SMILES: COc1cc2sc(CNC(=O)C3(CC(=O)[O-])Cc4cc(F)c(F)cc4C3)nc2cc1C(=O)N1CC[N+](C)(C)CC1]

a. Tert-butyl 2-[2-[[5-(4,4-dimethylpiperazin-4-ium-1-carbonyl)-6-methoxy-1,3-benzothiazol-2-yl]methylcarbamoyl]-5,6-difluoro-indan-2-yl]acetate Iodide

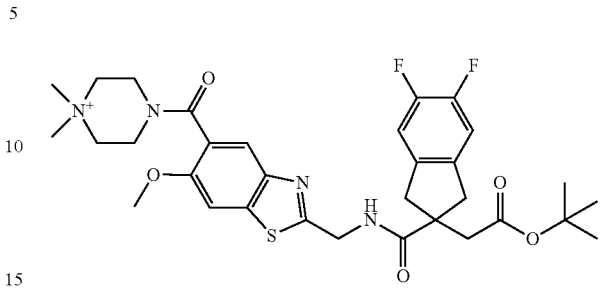

A solution of tert-butyl 5,6-difluoro-2-({[6-methoxy-5-(4-methylpiperazine-1-carbonyl)-1,3-benzothiazol-2-yl]methyl}carbamoyl)-2,3-dihydro-1H-indene-2-carboxylate, the final intermediate of Example 34, (140 mg, 0.23 mmol) in THF (5 mL) was treated with iodomethane (365 mg, 2.6 mmol). After 2 h the mixture was evaporated affording a white solid (170 mg, 98%). M/z 629.3 (M)$^+$.

b. 2-[2-[[5-(4,4-dimethylpiperazin-4-ium-1-carbonyl)-6-methoxy-1,3-benzothiazol-2-yl]methylcarbamoyl]-5,6-difluoro-indan-2-yl]acetate A solution of Tert-butyl 2-[2-[[5-(4,4-dimethylpiperazin-4-ium-1-carbonyl)-6-methoxy-1,3-benzothiazol-2-yl]methylcarbamoyl]-5,6-difluoro-indan-2-yl]acetate iodide (170 mg, 0.27 mmol) in DCM (4 mL) was treated with TFA (0.5 mL). After 2 h the mixture was evaporated. The residue as purified by MDAP and product-containing fractions were freeze-dried to afford the title compound as white solid (20 mg, 69%). M/z 574.2 (M+H)$^+$. $^1$H NMR (400 MHz, d$_6$-DMSO) δ 9.80 (1H, bs), 7.80 (2H, m), 7.25 (2H, t), 4.60 (2H, m), 4.10 (1H, m), 3.85 (3H, s), 3.80 (1H, m), 3.60-3.30 (12H, m), 3.20 (2H, d), 3.00 (2H, d).

Example 36 2-[2-[[5-[3-(dimethylamino)azetidine-1-carbonyl]-6-methoxy-1,3-benzothiazol-2-yl]methylcarbamoyl]indan-2-yl]acetic Acid

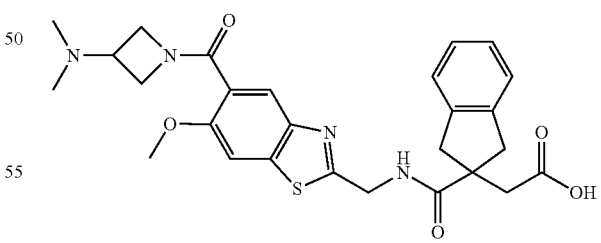

This was prepared using the same procedures as Example 33 with the difference that 3-dimethylaminoazetidine was used in place of 1-methylpiperazine, affording the title compounds as a white solid (62 mg). M/z 523.2 (M+H)$^+$. $^1$H NMR (400 MHz, d$_6$-DMSO) δ 12.30 (1H, bs), 8.80 (1H, s), 7.78 (1H, s), 7.72 (1H, s), 7.50 (1H, s), 7.20 (1H, m), 7.10 (1H, m), 5.40 (2H, bs), 4.62 (2H, m), 3.90 (3H, s), 4.20-3.80 (5H, m), 3.50 (2H, d), 3.30 (6H, s), 2.90 (2H, d).

Example 37 2-[2-[[5-[3-(dimethylamino)azetidine-1-carbonyl]-6-methoxy-1,3-benzothiazol-2-yl]methylcarbamoyl]-5,6-difluoro-indan-2-yl]acetic Acid

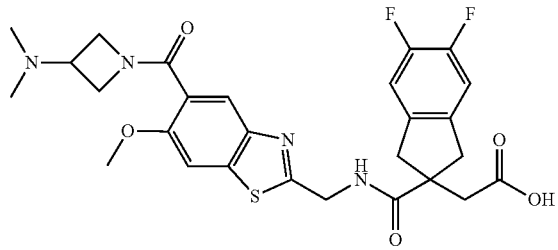 [SMILES: COc1cc2sc(CNC(=O)C3(CC(=O)O)Cc4cc(F)c(F)cc4C3)nc2cc1C(=O)N1CC(N(C)C)C1]

This was prepared using the same procedures as Example 36 with the difference that 2-[(tert-butoxy)carbonyl]-5,6-difluoro-2,3-dihydro-1H-indene-2-carboxylic acid was used in place of 2-[(tert-butoxy)carbonyl]-2,3-dihydro-1H-indene-2-carboxylic acid, affording the title compounds as a white solid (48 mg). M/z 559.2 (M+H)$^+$. $^1$H NMR (400 MHz, d$_6$-DMSO) δ 12.30 (1H, bs), 8.85 (1H, bs), 7.78 (1H, s), 7.72 (1H, s), 7.50 (1H, s), 7.25 (2H, t), 4.60 (2H, d), 3.85 (3H, s), 4.10-3.70 (5H, m), 3.50 (4H, m), 3.30 (6H, s), 2.95 (2H, d).

Example 38 2-[2-[[5-[4-(dimethylamino)piperidine-1-carbonyl]-6-methoxy-1,3-benzothiazol-2-yl]methylcarbamoyl]indan-2-yl]acetic Acid

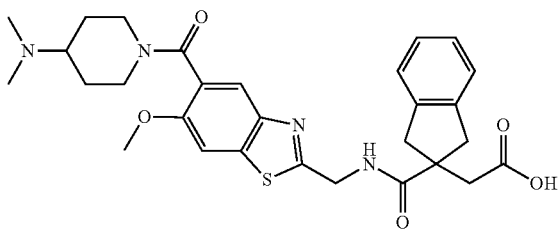 [SMILES: COc1cc2sc(CNC(=O)C3(CC(=O)O)Cc4ccccc4C3)nc2cc1C(=O)N1CCC(N(C)C)CC1]

This was prepared using the same procedures as Example 34 with the difference that 3-dimethylaminoazetidine was used in place of 1-methylpiperazine, affording the title compounds as a white solid (75 mg). M/z 551.7 (M+H)$^+$. $^1$H NMR (400 MHz, d$_6$-DMSO) δ 9.00 (1H, bs), 7.80 (2H, m), 7.25 (2H, m), 7.15 (2H, m), 4.65 (2H, m), 4.50 (1H, m), 3.85 (3H, s), 3.50 (2H, d), 3.00-2.60 (5H, m), 2.40 (1H, m), 2.20 (6H, s), 1.80 (1H, m), 1.60 (1H, m), 1.50 (2H, m).

Example 39 2-[2-[[6-methoxy-5-[4-(trimethylammonio)piperidine-1-carbonyl]-1,3-benzothiazol-2-yl]methylcarbamoyl]indan-2-yl]acetate

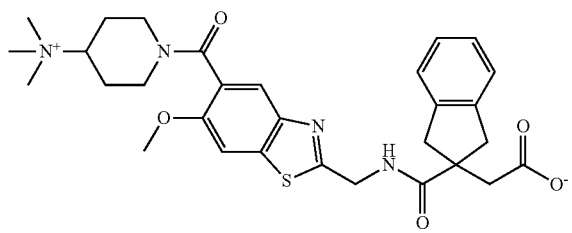 [SMILES: COc1cc2sc(CNC(=O)C3(CC(=O)[O-])Cc4ccccc4C3)nc2cc1C(=O)N1CCC([N+](C)(C)C)CC1]

This was prepared from tert-butyl 2-[({5-[4-(dimethylamino)piperidine-1-carbonyl]-6-methoxy-1,3-benzothiazol-2-yl}methyl)carbamoyl]-2,3-dihydro-1H-indene-2-carboxylate, the final intermediate of Example 38, by the quaternisation and TFA deprotection sequence as described in Example 35, affording the compound as a white solid (83 mg). M/z 565.7 (M+H)$^+$. $^1$H NMR (400 MHz, d$_6$-DMSO) δ 9.00 (1H, bs), 7.80 (2H, s), 7.20 (4H, m), 7.10 (2H, m), 4.70 (2H, m), 3.85 (3H, m), 3.60 (2H, m), 3.45 (2H, d), 3.05 (9H, s), 2.90 (3H, m), 2.20 (2H, m), 2.00 (2H, m), 1.50 (2H, m).

Example 40 2-[2-[[5-[2-[(dimethylamino)methyl]morpholine-4-carbonyl]-6-methoxy-1,3-benzothiazol-2-yl]methylcarbamoyl]indan-2-yl]acetic Acid

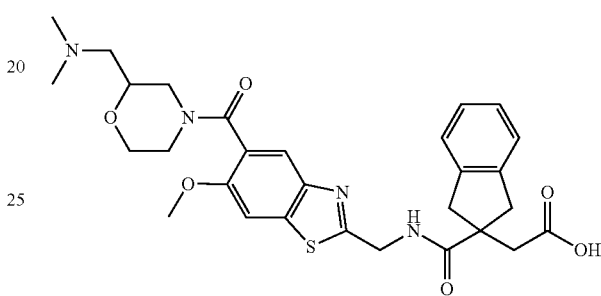

This was prepared using the same procedures as Example 33 with the difference that dimethyl[(morpholin-2-yl)methyl]amine was used in place of 1-methylpiperazine, affording the title compounds as a white solid (70 mg). M/z 567.7 (M+H)$^+$. $^1$H NMR (400 MHz, d$_6$-DMSO) δ 9.00 (1H, bs), 7.80 (1H, s), 7.70 (1H, s), 7.20 (2H, m), 7.10 (2H, m), 4.65 (2H, m), 4.20-4.00 (2H, m), 3.95 (2H, m), 3.85 (3H, s), 3.80-3.50 (3H, m), 3.45 (2H, d), 3.10 (6H, m), 3.05 (2H, d), 2.90 (2H, m).

Example 41 2-[2-[[6-methoxy-5-[2-[(trimethylammonio)methyl]morpholine-4-carbonyl]-1,3-benzothiazol-2-yl]methylcarbamoyl]indan-2-yl]acetate

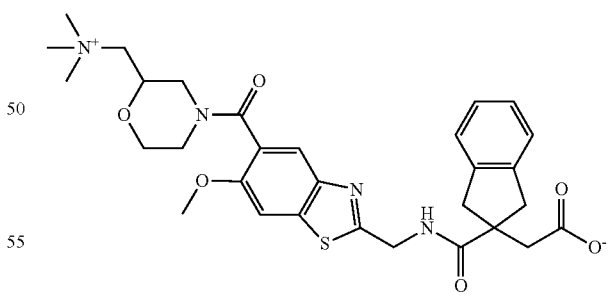

This was prepared from tert-butyl 2-{[(5-{2-[(dimethylamino)methyl]morpholine-4-carbonyl}-6-methoxy-1,3-benzothiazol-2-yl)methyl]carbamoyl}-2,3-dihydro-1H-indene-2-carboxylate, the final intermediate of Example 40, by the quaternisation and TFA deprotection sequence as described in Example 35, affording the compound as a white solid (77 mg). M/z 581.6 (M+H)$^+$. $^1$H NMR (400 MHz, d$_6$-DMSO) δ 13.30 (1H, bs), 7.80 (1H, s), 7.70 (1H, s), 7.20 (2H, m), 7.10 (2H, m), 4.65 (2H, m), 4.20-4.00 (2H, m), 3.95

(2H, m), 3.85 (3H, s), 3.80-3.50 (3H, m), 3.45 (2H, d), 3.15 (9H, s), 3.05 (2H, d), 2.80 (2H, m).

Example 42 2-[2-[[6-methoxy-5-[3-(trimethylammonio)azetidine-1-carbonyl]-1,3-benzothiazol-2-yl]methylcarbamoyl]indan-2-yl]acetate

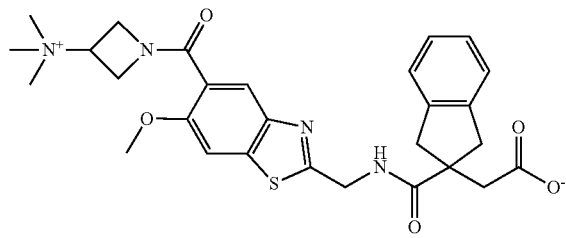 [SMILES: COc1cc2sc(CNC(=O)C3(CC(=O)[O-])Cc4ccccc4C3)nc2cc1C(=O)N1CC([N+](C)(C)C)C1]

This was prepared from tert-butyl 2-[({5-[3-(dimethylamino)azetidine-1-carbonyl]-6-methoxy-1,3-benzothiazol-2-yl}methyl)carbamoyl]-2,3-dihydro-1H-indene-2-carboxylate, the final intermediate of Example 36, by the quaternisation and TFA deprotection sequence as described in Example 35, affording the compound as a white solid (68 mg). M/z 537.6 (M+H)$^+$. $^1$H NMR (400 MHz, d$_6$-DMSO) δ 13.40 (1H, bs), 7.80 (2H, m), 7.20 (2H, m), 7.10 (2H, m), 4.65 (2H, d), 4.40 (2H, m), 4.30 (2H, m), 4.15 (1H, m), 3.90 (2H, m), 3.85 (3H, s), 3.55 (2H, m), 3.35 (2H, d), 3.15 (9H, s), 2.90 (2H, d).

Example 43 2-[5,6-difluoro-2-[[6-methoxy-5-[3-(trimethylammonio)azetidine-1-carbonyl]-1,3-benzothiazol-2-yl]methylcarbamoyl]indan-2-yl]acetate

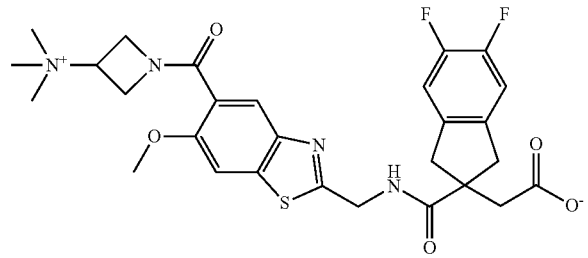 [SMILES: COc1cc2sc(CNC(=O)C3(CC(=O)[O-])Cc4cc(F)c(F)cc4C3)nc2cc1C(=O)N1CC([N+](C)(C)C)C1]

This was prepared from tert-butyl 2-[({5-[3-(dimethylamino)azetidine-1-carbonyl]-6-methoxy-1,3-benzothiazol-2-yl}methyl)carbamoyl]-5,6-difluoro-2,3-dihydro-1H-indene-2-carboxylate, the final intermediate of Example 37, by the quaternisation and TFA deprotection sequence as described in Example 35, affording the compound as a white solid (75 mg). M/z 573.6 (M+H)$^+$. $^1$H NMR (400 MHz, d$_6$-DMSO) δ 13.30 (1H, bs), 7.80 (2H, m), 7.20 (2H, t), 4.65 (2H, d), 4.40 (2H, m), 4.30 (2H, m), 4.15 (1H, m), 3.90 (2H, m), 3.85 (3H, s), 3.55 (2H, m), 3.35 (2H, d), 3.15 (9H, s), 2.90 (2H, d).

Example 44 2-[2-[[5-[(1,1-dimethylpiperidin-1-ium-4-yl)methoxy]-6-methoxy-1,3-benzothiazol-2-yl]methylcarbamoyl]-5,6-difluoro-indan-2-yl]acetate

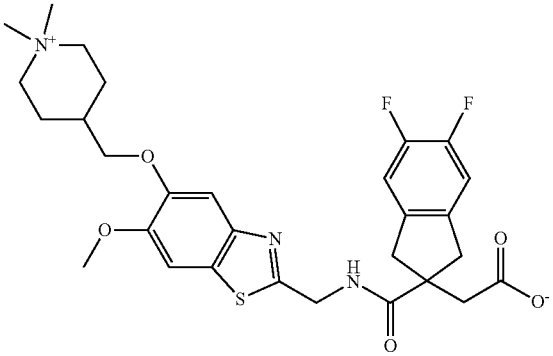 [SMILES: COc1cc2sc(CNC(=O)C3(CC(=O)[O-])Cc4cc(F)c(F)cc4C3)nc2cc1OCC1CC[N+](C)(C)CC1]

This was prepared from tert-butyl 5,6-difluoro-2-[({6-methoxy-5-[(1-methylpiperidin-4-yl)methoxy]-1,3-benzothiazol-2-yl}methyl)carbamoyl]-2,3-dihydro-1H-indene-2-carboxylate, the final intermediate in the synthesis of Example 10, by the quaternisation and TFA deprotection sequence as described in Example 35, affording the compound as a white solid (56 mg). M/z 574.4 (M+H)$^+$. $^1$H NMR (400 MHz, d$_6$-DMSO) δ 13.10 (1H, bs), 7.60 (1H, s), 7.45 (1H, s), 7.20 (2H, t), 4.65 (2H, d), 4.05 (2H, m), 3.85 (3H, s), 3.50 (2H, m), 3.45 (2H, d), 3.40 (2H, m), 3.10 (3H, s), 3.05 (3H, s), 2.90 (2H, d), 2.30 (2H, s), 2.05 (1H, m), 1.90 (2H, m), 1.80 (2H, m).

Example 45 2-[2-[[6-methoxy-5-(4-methylpiperazin-1-yl)sulfonyl-1,3-benzothiazol-2-yl]methylcarbamoyl]indan-2-yl]acetic Acid a. Tert-butyl N-{[5-(benzylsulfanyl)-6-methoxy-1,3-benzothiazol-2-yl]methyl}carbamate

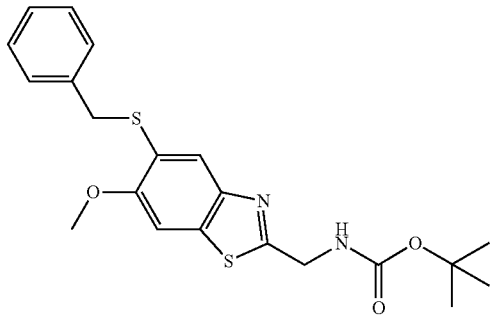 [SMILES: COc1cc2sc(CNC(=O)OC(C)(C)C)nc2cc1SCc1ccccc1]

A mixture of tert-butyl N-[(5-bromo-6-methoxy-1,3-benzothiazol-2-yl)methyl]carbamate (200 mg, 0.54 mmol), benzyl mercaptan (100 mg, 0.8 mmol), Xantphos (31 mg, 0.05 mmol), tris(dibenzylideneacetone)dipalladium(0) (25 mg, 0.027 mmol) and DIPEA (277 mg, 2.1 mmol) in 1,4-dioxane (5 mL) was heated at 115° C. in a sealed tube for 1.25 h then evaporated. The residue was treated with toluene and re-evaporated. The residue was chromatographed on silica eluting with 5-25% ethyl acetate in toluene affording a pale-yellow solid (220 mg, 99%). M/z 317.8 (M+H)$^+$ for loss of BOC group.

b. Tert-butyl N-{[5-(chlorosulfonyl)-6-methoxy-1,3-benzothiazol-2-yl]methyl}carbamate

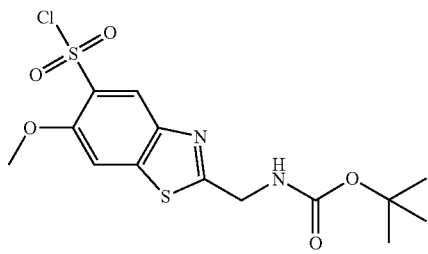 [SMILES: COc1cc2sc(CNC(=O)OC(C)(C)C)nc2cc1S(=O)(=O)Cl]

A solution of tert-butyl N-{[5-(benzylsulfanyl)-6-methoxy-1,3-benzothiazol-2-yl]methyl}carbamate (220 mg, 0.54 mmol) in acetic acid (3 mL) and water (0.4 mL) was treated with N-chlorosuccinimide (215 mg, 1.6 mmol). After 0.5 h the mixture was diluted with water and extracted twice with ethyl acetate. The combined extracts were washed with saturated aqueous sodium chloride solution, dried (Na$_2$SO$_4$) and evaporated. The residue was dissolved in toluene and re-evaporated to give a yellow oil that was used directly in the next step (210 mg, 100%). M/z 373.8 (M−H)$^-$ for loss of a proton from the corresponding sulfonic acid.

c. Tert-butyl N-({6-methoxy-5-[(4-methylpiperazin-1-yl)sulfonyl]-1,3-benzothiazol-2-yl}methyl)carbamate

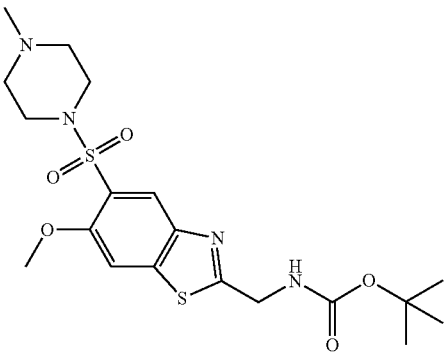 [SMILES: COc1cc2sc(CNC(=O)OC(C)(C)C)nc2cc1S(=O)(=O)N1CCN(C)CC1]

A solution of tert-butyl N-{[5-(chlorosulfonyl)-6-methoxy-1,3-benzothiazol-2-yl]methyl}carbamate (210 mg, 0.54 mmol) in DCM (5 mL) was treated at 0° C. with triethylamine (81 mg, 0.8 mmol) then 1-methylpiperazine (64 mg, 0.64 mmol). After 0.5 h the mixture was diluted with DCM and washed with dilute aqueous sodium bicarbonate solution, water, then dried (Na$_2$SO$_4$) and evaporated. The residue was chromatographed on silica eluting with 2-8% 2M ammonia/methanol in DCM affording a colourless oil (195 mg, 79%). M/z 457.6 (M+H)$^+$.

d. {6-Methoxy-5-[(4-methylpiperazin-1-yl)sulfonyl]-1,3-benzothiazol-2-yl}methanamine

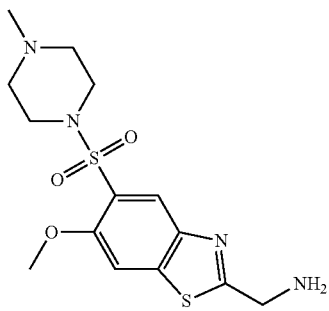 [SMILES: COc1cc2sc(CN)nc2cc1S(=O)(=O)N1CCN(C)CC1]

A solution of tert-butyl N-({6-methoxy-5-[(4-methylpiperazin-1-yl)sulfonyl]-1,3-benzothiazol-2-yl}methyl)carbamate (195 mg, 0.43 mmol) in DCM (3 mL) was treated with TFA (1 mL). After 1 h, toluene was added and the mixture evaporated. More toluene was added and the mixture re-evaporated. The residue was chromatographed on silica eluting with 2-12% 2M ammonia/methanol in DCM affording a colourless oil (133 mg, 87%). M/z 357.4 (M+H)$^+$.

e. Tert-butyl 2-[2-[[6-methoxy-5-(4-methylpiperazin-1-yl)sulfonyl-1,3-benzothiazol-2-yl]methylcarbamoyl]indan-2-yl]acetate

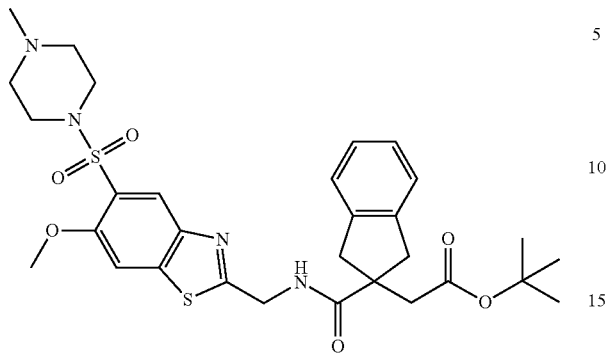

A solution of {6-methoxy-5-[(4-methylpiperazin-1-yl)sulfonyl]-1,3-benzothiazol-2-yl}methanamine (133 mg, 0.37 mmol), 2-(2-(tert-butoxy)-2-oxoethyl)-2,3-dihydro-1H-indene-2-carboxylic acid (103 mg, 0.37 mmol) and DIPEA (145 mg, 1.1 mmol) in DMF (2 mL) was treated with HATU (213 mg, 0.56 mmol). After 0.33 h the mixture was partitioned between ethyl acetate and dilute aqueous sodium bicarbonate solution, then washed with water, dried (Na$_2$SO$_4$) and evaporated. The residue was chromatographed on silica eluting with 2-10% 2M ammonia/methanol in DCM affording a light brown foam (233 mg, 95%). M/z 615.4 (M+H)$^+$ f. 2-[2-[[6-methoxy-5-(4-methylpiperazin-1-yl)sulfonyl-1,3-benzothiazol-2-yl]methylcarbamoyl]indan-2-yl]acetic acid A solution of tert-butyl 2-[2-[[6-methoxy-5-(4-methylpiperazin-1-yl)sulfonyl-1,3-benzothiazol-2-yl]methylcarbamoyl]indan-2-yl]acetate (92 mg, 0.15 mmol) in DCM (3 mL) was treated with TFA (1.5 mL). After 3 h the mixture was diluted with toluene and evaporated. Toluene was added and the mixture re-evaporated. The residue was purified by reverse phase chromatography (C18 cartridge) 5-20% ACN in 2M ammonia/methanol affording the title compound as a white solid (66 mg, 79%). M/z 559.2 (M+H)$^+$. $^1$H NMR (400 MHz, d$_6$-DMSO) δ 9.00 (1H, bs), 8.20 (1H, s), 7.95 (1H, s), 7.22 (1H, m), 7.15 (1H, m), 4.65 (2H, m), 3.95 (3H, s), 3.50 (2H, d), 3.15 (4H, m), 2.90 (2H, d), 2.30 (4H, m), 2.20 (3H, s).

Example 46 2-[2-[[5-[[4-(dimethylamino)-1-piperidyl]sulfonyl]-6-methoxy-1,3-benzothiazol-2-yl]methylcarbamoyl]indan-2-yl]acetic Acid

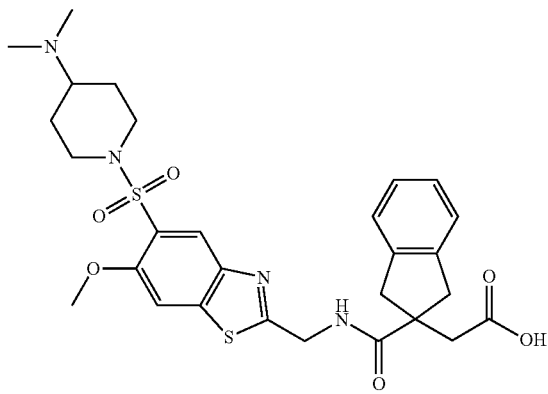 [SMILES: COc1cc2sc(CNC(=O)C3(CC(=O)O)Cc4ccccc4C3)nc2cc1S(=O)(=O)N1CCC(N(C)C)CC1]

This was prepared by the same procedures as for Example 45 with the difference that N,N-dimethylpiperidin-4-amine was used in place of 1-methylpiperazine, affording the title compound as a white solid (69 mg). M/z 587.2 (M+H)$^+$. $^1$H NMR (400 MHz, d$_6$-DMSO) δ 9.00 (1H, bs), 8.20 (1H, s), 7.90 (1H, s), 7.20 (2H, m), 7.10 (2H, m), 4.65 (2H, d), 3.90 (3H, s), 3.70 (2H, m), 3.40 (2H, d), 2.90 (2H, d), 2.60 (1H, t), 2.30 (2H, m), 2.20 (6H, s), 1.80 (2H, m), 1.40 (2H, m).

Example 47 2-[2-[[6-methoxy-5-[[4-(trimethylammonio)-1-piperidyl]sulfonyl]-1,3-benzothiazol-2-yl]methylcarbamoyl]indan-2-yl]acetate

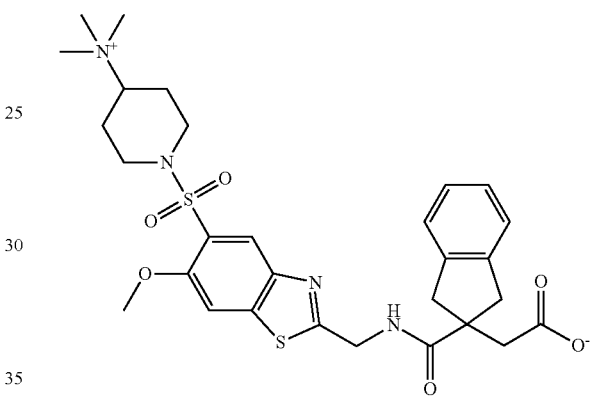

This compound was prepared from tert-butyl 2-{[(5-{[4-(dimethylamino)piperidin-1-yl]sulfonyl}-6-methoxy-1,3-benzothiazol-2-yl)methyl]carbamoyl}-2,3-dihydro-1H-indene-2-carboxylate, the final intermediate in the synthesis of Example 46, by the quaternisation and TFA deprotection sequence as described in Example 35, affording the compound as a white solid (91 mg). M/z 601.3 (M+H)$^+$. $^1$H NMR (400 MHz, d$_6$-DMSO) δ 8.20 (1H, s), 8.00 (1H, s), 7.15 (2H, m), 7.10 (2H, m), 4.65 (2H, d), 3.95 (3H, s), 3.90 (2H, m), 3.40 (2H, d), 3.00 (9H, s), 2.90 (2H, d), 2.60 (1H, m), 2.30 (1H, m), 2.10 (2H, m), 1.60 (2H, m).

Example 48 2-[2-[(6-cyano-1,3-benzothiazol-2-yl)methylcarbamoyl]indan-2-yl]acetic Acid

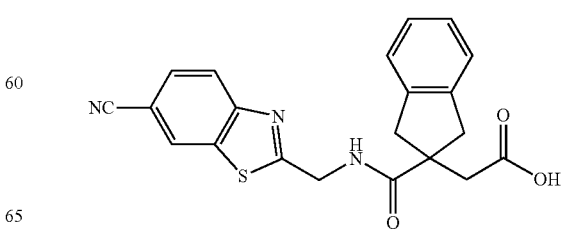

a. Tert-butyl 2-[2-[(6-bromo-1,3-benzothiazol-2-yl)methylcarbamoyl]indan-2-yl]acetate

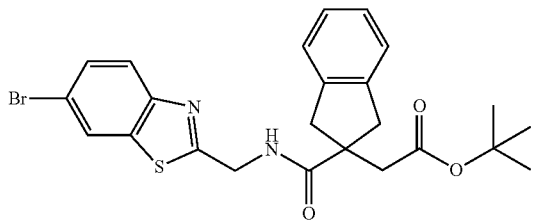 [SMILES: CC(C)(C)OC(=O)CC1(C(=O)NCc2nc3ccc(Br)cc3s2)Cc2ccccc2C1]

This was prepared by the same procedures as for Example 24 step-b to step-d starting with 4-bromo-2-iodo-aniline, affording the title compound as a white solid. M/z 501.1 (M+H)⁺.

b. Tert-butyl 2-[2-[(6-cyano-1,3-benzothiazol-2-yl)methylcarbamoyl]indan-2-yl]acetate

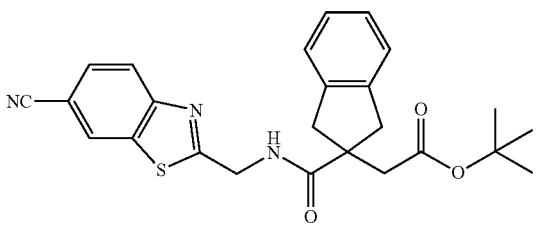 [SMILES: CC(C)(C)OC(=O)CC1(C(=O)NCc2nc3ccc(C#N)cc3s2)Cc2ccccc2C1]

To a stirred solution of tert-butyl 2-[2-[(6-bromo-1,3-benzothiazol-2-yl)methylcarbamoyl]indan-2-yl]acetate (300 mg, 0.59 mmol) in DMF (6 mL) was added $Zn(CN)_2$ (140 mg, 1.19 mmol) and purged with argon for 10 minutes. Then $Pd_2(dba)_3$ (55 mg, 0.05 mmol) and Xantphos (70 mg, 0.11 mmol) were added and purged with argon for further 5 minutes. The reaction mixture was heated in sealed tube at 90° C. for 4 h, and then filtered through celite pad, washed the pad with EtOAc (50 mL) and the filtrate was evaporated. The crude was purified by silica gel chromatography eluting with 20-30% EtOAc in petroleum ether affording an off white solid (180 mg, 68%). M/z 448.2 (M+H)⁺.

c. 2-[2-[(6-cyano-1,3-benzothiazol-2-yl)methylcarbamoyl]indan-2-yl]acetic Acid A solution of tert-butyl 2-[2-[(6-cyano-1,3-benzothiazol-2-yl)methylcarbamoyl]indan-2-yl]acetate (160 mg, 0.35 mmol) in DCM (5 mL) was treated with TFA (2.5 mL) at room temperature for 4 h. The mixture was evaporated and the residue was triturated with diethyl ether (10 mL). The crude compound was purified by preparative HPLC [X-BRIDGE-C18 (150*30), 5 u, Mobile phase: A: 0.1% Formic Acid in $H_2O$, B: MeCN] affording the title product as a white solid (26 mg, 19%). M/z 392.1 (M+H)⁺. ¹H NMR (500 MHz, DMSO-$d_6$): δ 9.31 (1H, bs), 8.65 (1H, s), 8.09 (1H, d, J=8.5 Hz), 7.90 (1H, dd, J=8.5 Hz, J=1.5 Hz), 7.22-7.20 (2H, m), 7.14-7.13 (2H, m), 4.71 (2H, d, J=5.5 Hz), 3.45 (2H, d, J=16.5 Hz), 2.99 (2H, d, J=16.5 Hz), 2.70 (2H, s).

Example 49 2-[2-[(5-cyano-1,3-benzothiazol-2-yl)methylcarbamoyl]indan-2-yl]acetic Acid

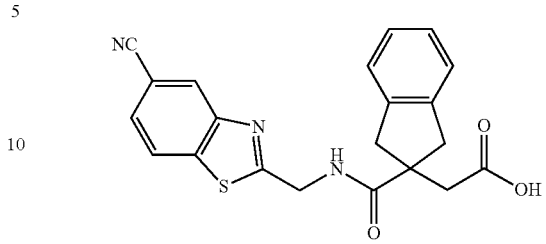

This compound was prepared from tert-butyl 2-[2-[(5-bromo-1,3-benzothiazol-2-yl)methylcarbamoyl]indan-2-yl]acetate using the conditions described in example 48 affording the compound as a white solid. M/z 392.1 (M+H)⁺. ¹H NMR (500 MHz, DMSO-$d_6$): δ 10.7 (1H, bs), 8.46 (1H, s), 8.28 (1H, d, J=8.5 Hz), 7.79 (1H, d, J=8.5 Hz), 7.19-7.18 (2H, m), 7.13-7.11 (2H, m), 4.70 (2H, d, J=5 Hz), 3.42 (2H, d, J=16 Hz), 2.95 (2H, d, J=16 Hz), 2.57 (2H, s).

Example 50: LasB Inhibitory Activity Measurements

The relevance of LasB to PA infection has been shown in experiments measuring lung burden in a rat model of chronic lung infection following infection with WT PA (which expresses LasB) and a mutant form of PA (ΔlasB PA) in which LasB is not expressed. It could be clearly seen in that following infection, whereas a wild type strain is able to persist at least for 14 days, a LasB deficient strain was not able to persist beyond day 5. The relevance of LasB to PA biofilm development was also shown. Biofilms formed after 3 days by both PA26 wt and PA26 lasB deletion strains were investigated by confocal imaging and subsequent analysis (with Comstat software). This study demonstrated that biofilms formed by the PA26 lasB deletion strain were highly reduced in thickness and biomass compared to the wt strain, demonstrating the essential role of LasB in PA biofilm development.

The relevance of LasB to *Pseudomonas aeruginosa* (PA) infection is illustrated in FIG. 1, which shows incidence of mortality versus survival, and chronic colonisation versus bacterial clearance, in a mouse model of lung infection. Chronicity of the infection is defined by PA lung burden higher than 10^3 CFU seven days after infection. In this infection model, both wild type strain (expressing LasB; "wt RP45") and the isogenic lasB deleted strain (which does not express LasB; "mutant RP45") cause similar mortality (in around 40% of infected mice); however the incidence of chronic colonization was significantly lower for the mutant strain in comparison to the wt counterpart (87% for the wt vs 43% for the lasB deleted strain; Fisher exact test p<0.01). This finding shows the role of LasB in establishment of chronic colonization.

Experiments were therefore conducted (1) to measure the potency of inhibition of compounds of the invention against purified *Pseudomonas aeruginosa* LasB enzyme and also experiments were conducted (2) to measure the ability of compounds of the invention to inhibit LasB-catalysed elastin degradation. The first assay uses a commercial fluorescent synthetic peptide and purified LasB enzyme. The LasB hydrolysis kinetics are measured allowing the determination of the IC50 and Ki of the inhibitors; the second is a more physiological assay using dialysed *Pseudomonas aeruginosa* supernatant as source of enzyme, plus its natural substrate Elastin. It is an "end point assay" that determines the percentage of LasB inhibition by each compound for one particular time point and inhibitor concentration. Technical details are described below:

Fluorometric Assay to Determine Ki

This assay uses commercially available substrate (Abz-Ala-Gly-Leu-Ala-p-Nitro-Benzyl-Amide (Ex: 340 nm, Em: 415 nm) from Peptide International) and purified LasB protein from *P. aeruginosa* (provided by Merck or Charles River Laboratories). It is performed to determine LasB elastase activity and assess compound inhibition in 96-well plate format. All compounds of Formula (I) were assessed using the method described below.

Method: 10 to 140 ng/ml purified LasB is incubated with 250 µM Abz-Ala-Gly-Leu-Ala-p-Nitro-Benzyl-Amide in 50 mM Tris-HCl pH 7.4, 2.5 mM $CaCl_2$), 0.01% of Triton X100 at 37° C. LasB activity (corresponding to fluorescence emission induced by substrate hydrolysis) is measured over 30 min at 37° C. with a fluorescence plate reader such as the Perkin Elmer Envision or similar. Different range of inhibitor concentrations are routinely assessed depending of inhibitor potency from 0.0016 to 200 µM (2-fold dilutions series) in order to determine IC50.

The equation used to calculate the Ki from IC50 is: $Ki=IC50/(1+([S]/Km))$ where $[S]=250$ µM and $Km=214$ µM.

Elastin Assay to Determine % Inhibition

The Elastin assay uses as source of enzyme dialysed supernatant from *P. aeruginosa* PAO1 and the Elastin Congo-Red as substrate. The natural LasB substrate, elastin, is complexed with the congo-red dye (Elastin Congo-Red, ECR). The elastolysis activity from the culture supernatant will degrade elastin and release the congo-red dye into the supernatant. This red dye release can be measured with a spectrophotometer.

All compounds of Formula (I) were assessed using the method described below.

Method: To determine LasB elastase activity and assess compound inhibition, an overnight culture of *P. aeruginosa* strain PAO1 is diluted in LB medium. After reaching an $OD_{600\ nm}$ of 0.6, this culture is diluted and incubated for additional 18-24 hours in a shaking incubator. Culture supernatants are recovered by centrifugation and filtrated through a 0.22 µM filter. These supernatants are dialysed (filtration molecules <20 kDa) into a 50 mM Tris-HCl pH 7.4, 2.5 mM $CaCl_2$ solution at 4° C. under agitation for 24 hours. Supernatant dialysed is then mixed volume/volume with the ECR suspension (20 mg/mL of ECR in 100 mM Tris-HCl pH 7.4 buffer supplemented with 1 mM $CaCl_2$)) supplemented with Triton X100 (final concentration of 0.01%) in presence of DMSO (positive control) and/or different concentrations of compound (routinely 50 to 1.56 µM). As a negative control, the dialysed supernatant is replaced by Tris-HCl solution (50 mM Tris-HCl pH 7.4, 2.5 M $CaCl_2$). The mixed reaction is then incubated overnight in a 37° C. shaking incubator. The reaction supernatant is recovered by centrifugation and the release of congo-red is measured by its absorbance at 495 nm ($OD_{495\ nm}$).

Percentage inhibition is determined using the following equation:

$$((OD_{495\ nm}\text{ value of positive control} - OD_{495\ nm}\text{ value of negative control}) - (OD_{495\ nm}\text{ value of treated supernatant} - OD_{495\ nm}\text{ value of negative control}))/(OD_{495\ nm}\text{ value of positive control} - OD_{495\ nm}\text{ value of negative control}) \times 100.$$

Results are shown in the Table below and categorised into A, B and C for both assays. The Ki values are grouped as A (Ki=0.00 to 0.05 µM), B (Ki=0.05 to 0.2 µM) and C (Ki=0.2 to 10.00 M). Similarly, for the elastase hydrolysis assay, values are grouped into A (>80% inhibition), B (60 to 80% inhibition) and C (10 to 60% inhibition) all at 25 µM inhibitor concentration. (n.d. not determined).

| Example | Ki (µM) | Elastin hydrolysis % inhibition @ 25 µM inhibitor concentration |
|---|---|---|
| 1 | C | C |
| 2 | C | ND |
| 3 | B | B |
| 4 | C | ND |
| 5 | C | ND |
| 6 | B | B |
| 7 | C | ND |
| 8 | B | B |
| 9 | A | A |
| 10 | A | A |
| 11 | A | A |
| 12 | B | B |
| 13 | B | B |
| 14 | B | B |
| 15 | B | B |
| 16 | A | B |
| 17 | B | B |
| 18 | A | B |
| 19 | A | A |
| 20 | A | B |
| 21 | A | A |
| 22 | A | B |
| 23 | A | A |
| 24 | C | B |
| 25 | C | B |
| 26 | C | ND |
| 27 | B | B |
| 28 | C | ND |
| 29 | C | ND |
| 30 | C | ND |
| 31 | C | ND |
| 32 | B | B |
| 33 | A | B |
| 34 | A | A |
| 35 | B | B |
| 36 | A | A |
| 37 | A | A |
| 38 | B | B |
| 39 | C | ND |
| 40 | B | B |
| 41 | B | B |
| 42 | C | B |
| 43 | B | B |
| 44 | A | A |
| 45 | B | B |
| 46 | B | B |
| 47 | B | B |
| 48 | B | B |
| 49 | B | B |

Example 51: Inhibition of LasB-Mediated IL-10 Activation

The activity of compounds of the invention to inhibit LasB-mediated hydrolysis of pro-IL-1β to IL-1β was demonstrated using an enzymatic in vitro assay, using purified LasB and a reporter substrate (a FRET peptide mimicking the LasB IL-1β cleavage site). Hydrolysis of this FRET peptide was continuously monitored using a Victor multi-mode plate reader (Perkin Elmer) with excitation 355 nm and emission at 450 nm in the presence of varying concentrations of compounds of the invention. Inhibitory constants (Ki) were determined for certain compounds of the invention (at least 2 independent replicates) using a competitive inhibitor model. Results are shown in the table below.

| Example | Ki (LasB-mediated hydrolysis of pro-IL-1β to IL-1β)/ μM |
|---|---|
| 9 | 0.16 |
| 11 | 0.22 |
| 19 | 0.27 |
| 20 | 0.34 |
| 22 | 0.40 |
| 23 | 0.50 |
| 44 | 0.30 |

Example 52: In Vivo Efficacy of Compounds of the Invention

Experiments were conducted to demonstrate the efficacy of compounds of the invention in treating a mouse model of *Pseudomonas aeruginosa* lung infection.

Mice were dosed by intranasal inoculation of PA (PAO1), then sacrified after 24 hours. The extent of infection in the lung was quantified by bacterial load (CFU determination, colony forming units) and the levels of proinflammatory IL-1β. Statistical analysis on both readouts were performed by ANOVA with a Dunnett post-test.

Compounds were administered intravenously in a two-dose regimen (1 hour and 2 hours post infection) at two different doses (10 and 30 mg/kg). As shown in FIG. 2, the compound of Example 23 inhibited the production and activation of IL-1β in mice infected by wild-type PA (PA01) at a similar level than the lasB deleted mutant (ΔlasB), which cannot produce LasB. As shown in FIG. 3, the compound of Example 23 reduced the extent of infection in the lung to the level of the LasB deleted mutant (ΔlasB), as determined by the CFU levels.

The invention claimed is:

1. A compound which is an indane according to Formula (I), or a pharmaceutically acceptable salt thereof,

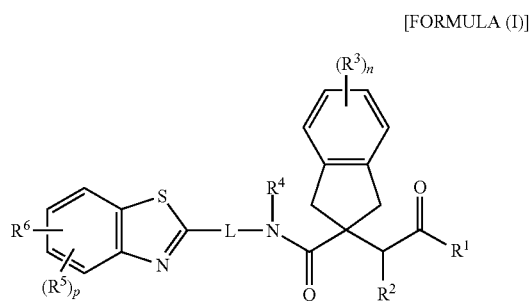

[FORMULA (I)]

wherein
$R^1$ is selected from:
  NHOH, OH, $OR^{1a}$ and $-OCH_2OC(O)R^{1a}$, wherein $R^{1a}$ is selected from an unsubstituted $C_1$ to $C_4$ alkyl group and phenyl; and
  where the compound of Formula (I) contains a positively charged nitrogen atom, $R^1$ may be $O^-$, such that the compound forms a zwitterion;
$R^2$ is selected from H and unsubstituted $C_1$ to $C_2$ alkyl;
each $R^3$ group is independently selected from halogen, $-OH$, $-NH_2$, methyl and $-CF_3$;
n is an integer from 0 to 4;
$R^4$ is selected from H and unsubstituted $C_1$ to $C_2$ alkyl;
L is selected from a bond and a $C_1$ to $C_3$ alkylene group which is unsubstituted or is substituted by one group selected from halogen, $-OH$, $-OMe$, $-NR^{20}R^{21}$; $N^+R^{20}R^{21}R^{22}$, and $-CF_3$;
p is 0 or 1;
$R^5$ is selected from $-OMe$, $-OH$, halogen, $-NR^{20}R^{21}$; $-N^+R^{20}R^{21}R^{22}$, $-CF_3$, and $R^6$;
each $R^6$ is independently selected from:
  $-R^{6a}R^A$, $-O-R^{6a}R^A$, $-NR^{20}-R^{6a}R^A$, $-R^{6b}R^B$, $-O-R^{6b}R^B$, and $-NR^{20}-R^{6b}R^B$;
  $-R^XR^R$, $-O-R^XR^R$, $-O-R^X-C(O)-R^R$, $-R^X-C(O)-R^R$, $-NR^{20}-R^XR^R$, and $-NR^{20}-R^X-C(O)-R^R$; and
  $-CN$; $-C(O)NR^{20}R^{21}$; $-C(O)NR^{21}-R^XR^B$; $-C(O)NR^{40}R^{41}$; $-SO_2R^{20}$; $-SO_2-R^XR^B$; $-SO_2NR^{20}R^{21}$; $-SO_2-NR^{20}-R^XR^B$; and $-SO_2NR^{40}R^{41}$;
wherein:
  each $R^X$ is independently selected from $R^{6a}$ and $R^{6b}$;
  each $R^{6a}$ is independently selected from $C_1$ to $C_4$ alkylene, $C_2$ to $C_4$ alkenylene and $C_2$ to $C_4$ alkynylene; and each $R^{6a}$ is independently unsubstituted or is substituted by one group selected from $-OH$, halogen; $-NR^{20}R^{21}$; $-N^+R^{20}R^{21}R^{22}$; $-NR^{20}C(NR^{21})NR^{22}R^{23}$; $-NR^{20}C(N^+R^{21}R^{22})NR^{23}R^{24}$; $-NR^{20}C(NR^{21})R^{22}$; $-NR^{20}C(N^+R^{21}R^{22})R^{23}$; $-C(NR^{20})NR^{21}R^{22}$; $-C(N^+R^{20}R^{21})NR^{22}R^{23}$; $-C(NR^{20})R^{21}$; and $-C(N^+R^{20}R^{21})R^{22}$; $-C(O)NR^{20}R^{21}$; $-C(O)N^+R^{20}R^{21}R^{22}$; $-C(O)-R^{20}$, and methoxy which is unsubstituted or is substituted by one, two or three halogen substituents;
  each $R^{6b}$ is independently selected from $[C_1$ to $C_3$ alkylene$]-C(R^Z)_2R^b$, $[C_2$ to $C_3$ alkenylene$]-C(R^Z)_2R^b$ and $[C_2$ to $C_3$ alkynylene$]-C(R^Z)_2R^b$; wherein the two $R^Z$ groups are attached together to form, together with the atom to which they are attached, a 5- or 6-membered carbocyclic or heterocyclic group;
  $R^A$ is selected from $-NR^{20}R^{30}$; $-N^+R^{20}R^{21}R^{30}$; $-NR^{20}NR^{21}R^{22}$; $-NR^{20}N^+R^{21}R^{22}R^{23}$; $-N^+R^{20}R^{21}NR^{22}R^{23}$; $-NR^{20}C(NR^{21})NR^{22}R^{30}$; $-NR^{20}C(N^+R^{21}R^{22})NR^{23}R^{30}$; $-C(NR^{20})NR^{21}R^{22}$; and $-C(N^+R^{20}R^{21})NR^{22}R^{23}$;
  $R^B$ is selected from $-NR^{20}R^{21}$; $-N^+R^{20}R^{21}R^{22}$; $-NR^{20}NR^{21}R^{22}$; $-NR^{20}N^+R^{21}R^{22}R^{23}$; $-N^+R^{20}R^{21}NR^{22}R^{23}$; $-NR^{20}C(NR^{21})NR^{22}R^{23}$; $-NR^{20}C(N^+R^{21}R^{22})NR^{23}R^{24}$; $-C(NR^{20})NR^{21}R^{22}$; and $-C(N^+R^{20}R^{21})NR^{22}R^{23}$;
  $R^{40}$ and $R^{41}$, together with the nitrogen atom to which they are attached, form a 4- to 6-membered heterocyclic group, wherein any nitrogen atom in the ring is independently selected from secondary, tertiary and quaternary nitrogen atoms;
  each $R^R$ is independently a 4- to 10-membered heteroaryl or heterocyclic group comprising at least one nitrogen atom, and said nitrogen atom(s) are independently selected from secondary, tertiary and quaternary nitrogen atom(s);
    wherein each $R^R$, and each ring formed by $-NR^{40}R^{41}$, is independently unsubstituted or is substituted with one, two or three groups independently selected from
    i) halogen, $-CN$;
    ii) oxo, providing that said $R^R$ group is a heterocyclic group;
    iii) $-R^{20}$, $-R^7-OR^{20}$; $-R^7-NR^{20}R^{21}$; $-R^7-N^+R^{20}R^{21}R^{22}$; $-R^7-NR^{20}C(NR^{21})NR^{22}R^{23}$;

—$R^7$—$NR^{20}C(N^+R^{21}R^{22})NR^{23}R^{24}$; —$R^7$—$NR^{20}C(NR^{21})R^{22}$; —$R^7$ $NR^{20}C(N^+R^{21}R^{22})R^{23}$;
—$R^7$—$C(NR^{20})NR^{21}R^{22}$; —$R^7$—$C(N^+R^{20}R^{21})NR^{22}R^{23}$; —$R^7$—$C(NR^{20})R^{21}$; and
—$R^7$—$C(N^+R^{20}R^{21})R^{22}$;

each $R^7$ is independently selected from a bond and unsubstituted $C_1$ to $C_3$ alkylene;

$R^{20}$, $R^{21}$, $R^{22}$, $R^{23}$ and $R^{24}$ are each independently selected from H and $C_1$ to $C_3$ alkyl which is unsubstituted or is substituted with one —OH or —OMe group or with one, two or three halogen groups;

each $R^{30}$ is independently selected from $C_2$ to $C_3$ alkyl which is unsubstituted or is substituted with one —OH or —OMe group or with one, two or three halogen groups.

2. The compound of claim 1 wherein
$R^5$ is selected from —OMe and —OH;
or
p is 0.

3. The compound of claim 1 wherein:
$R^1$ is selected from OH and NHOH; or where the compound of Formula (I) contains a positively charged nitrogen atom, $R^1$ may be O—, such that the compound forms a zwitterion;
$R^2$ is selected from H and unsubstituted methyl; and
$R^4$ is H.

4. The compound of claim 1, wherein n is an integer from 0 to 2 and each $R^3$ group is independently selected from halogen and —OH.

5. The compound of claim 1 wherein L is an unsubstituted $C_1$ alkylene group.

6. The compound of claim 1 wherein each $R^6$ is independently selected from:
—$R^{6a}R^A$, —O—$R^{6a}R^A$, —$NR^{20}$—$R^{6a}R^A$, —$R^{6b}R^B$, —O—$R^{6b}R^B$, —$NR^{20}$—$R^{6b}R^B$, —$R^XR^R$, —O—$R^XR^R$, —O—$R^X$—C(O)—$R^R$, and —$R^X$—C(O)—$R^R$,
wherein:
each $R^X$ is an $R^{6a}$ group;
each $R^{6a}$ is independently a $C_1$ to $C_4$ alkylene group and each $R^{6a}$ is independently unsubstituted or is substituted by one group selected from —OH, halogen; —$NR^{20}R^{21}$; —$N^+R^{20}R^{21}R^{22}$; and unsubstituted methoxy;
each $R^{6b}$ is independently a [$C_1$ to $C_3$ alkylene]—C($R^Z$)$_2$ $R^b$ group; wherein the two $R^Z$ groups are attached together to form, together with the atom to which they are attached, a 5- or 6-membered carbocyclic or heterocyclic group;
$R^A$ is selected from —$NR^{20}R^{30}$; —$N^+R^{20}R^{21}R^{30}$; —$NR^{20}NR^{21}R^{22}$; and —$NR^{20}N^+R^{21}R^{22}R^{23}$;
$R^B$ is selected from —$NR^{20}R^{21}$; —$N^+R^{20}R^{21}R^{22}$; —$NR^{20}NR^{21}R^{22}$; and —$NR^{20}N^+R^{21}R^{22}R^{23}$;
each $R^R$ is independently a 5- to 6-membered heteroaryl or 4- to 6-membered heterocyclic group comprising at least one nitrogen atom, and said nitrogen atom(s) are independently selected from secondary, tertiary and quaternary nitrogen atom(s); wherein each $R^R$ is independently unsubstituted or is substituted with one, two or three groups independently selected from —$R^{20}$, —$R^7$—$OR^{20}$; —$R^7$—$NR^{20}R^{21}$; and —$R^7$ $N^+R^{20}R^{21}R^{22}$.

7. The compound of claim 1 wherein each $R^6$ is independently selected from:
—O—$R^{6a}R^A$, —O—$R^{6b}R^B$, —O—$R^XR^R$, and —O—$R^X$—C(O)—$R^R$, wherein:

each $R^X$ is an $R^{6a}$ group;
each $R^{6a}$ is independently an unsubstituted $C_1$ to $C_4$ alkylene group;
each $R^{6b}$ is independently a [$C_1$ to $C_3$ alkylene]—C($R^Z$)$_2$ $R^b$ group; wherein the two $R^Z$ groups are attached together to form, together with the atom to which they are attached, a 5- or 6-membered heterocyclic group;
$R^A$ is selected from —$NR^{20}R^{30}$; —$N^+R^{20}R^{21}R^{30}$; —$NR^{20}NR^{21}R^{22}$; and —$NR^{20}N^+R^{21}R^{22}R^{23}$;
$R^B$ is selected from —$NR^{20}R^{21}$; —$N^+R^{20}R^{21}R^{22}$; —$NR^{20}NR^{21}R^{22}$; and —$NR^{20}N^+R^{21}R^{22}R^{23}$;
each $R^R$ is independently a 5- to 6-membered heteroaryl or 4- to 6-membered heterocyclic group comprising at least one nitrogen atom, and said nitrogen atom(s) are independently selected from secondary, tertiary and quaternary nitrogen atom(s); wherein each $R^R$ is independently unsubstituted or is substituted with one or two groups independently selected from —$R^{20}$; —$R^7$—$NR^{20}R^{21}$; and —$R^7$—$N^+R^{20}R^{21}R^{22}$.

8. The compound of claim 1 wherein each $R^6$ is independently selected from:
—CN; —C(O)$NR^{20}R^{21}$; —C(O)$NR^{21}$—$R^XR^B$; —C(O)$NR^{40}R^{41}$; —$SO_2R^{20}$; —$SO_2NR^{20}R^{21}$; and —$SO_2NR^{40}R^{41}$;
wherein:
each $R^X$ is a $R^{6a}$ group;
each $R^{6a}$ is independently a $C_1$ to $C_4$ alkylene group; and each $R^{6a}$ is independently unsubstituted or is substituted by one group selected from —OH, halogen; —$NR^{20}R^{21}$; —$N^+R^{20}R^{21}R^{22}$; and unsubstituted methoxy;
$R^B$ is selected from —$NR^{20}R^{21}$; —$N^+R^{20}R^{21}R^{22}$; —$NR^{20}NR^{21}R^{22}$; and —$NR^{20}N^+R^{21}R^{22}R^{23}$;
each $R^{40}$ and $R^{41}$ together with the nitrogen atom to which they are attached, independently form a 4- to 6-membered heterocyclic group, wherein any nitrogen atom in the ring is independently selected from secondary, tertiary and quaternary nitrogen atoms; wherein each ring formed by —$NR^{40}R^{41}$ is independently unsubstituted or is substituted with one, two or three groups independently selected from —$R^{20}$, —$R^7$—$OR^{20}$; —$R^7$—$NR^{20}R^{21}$; and —$R^7$—$N^+R^{20}R^{21}R^{22}$.

9. The compound of claim 1 wherein each $R^6$ is independently selected from:
—CN; —C(O)$NR^{20}R^{21}$; —C(O)$NR^{21}$—$R^XR^B$; —C(O)$NR^{40}R^{41}$; —$SO_2R^{20}$; —$SO_2NR^{20}R^{21}$; and —$SO_2NR^{40}R^{41}$;
wherein:
each $R^X$ is a $R^{6a}$ group;
each $R^{6a}$ is independently an unsubstituted $C_1$ to $C_4$ alkylene group;
$R^B$ is selected from —$NR^{20}R^{21}$ and —$N^+R^{20}R^{21}R^{22}$;
each $R^{40}$ and $R^{41}$ together with the nitrogen atom to which they are attached, independently form a 4- to 6-membered heterocyclic group, wherein any nitrogen atom in the ring is independently selected from secondary, tertiary and quaternary nitrogen atoms; wherein each ring formed by $NR^{40}R^{41}$ is independently unsubstituted or is substituted with one or two groups independently selected from —$R^{20}$; —$R^7$—$NR^{20}R^{21}$; and —$R^7$—$N^+R^{20}R^{21}R^{22}$.

10. The compound of claim 1 wherein each $R^R$, or each ring formed by —$NR^{40}R^{41}$, if present is independently selected from azetidine, morpholine, piperazine, piperidine, pyrrolidine and triazole.

11. The compound of claim 1, which compound is selected from 1. 2-[2-[(4-carbamoyl-1,3-benzothiazol-2-yl) methylcarbamoyl]indan-2-yl]acetic acid
2. 2-[2-[[4-(pyrrolidine-1-carbonyl)-1,3-benzothiazol-2-yl]methylcarbamoyl]indan-2-yl]acetic acid
3. 2-[2-[(4-pyrrolidin-1-ylsulfonyl-1,3-benzothiazol-2-yl) methylcarbamoyl]indan-2-yl]acetic acid
4. 2-[2-[(4-sulfamoyl-1,3-benzothiazol-2-yl) methylcarbamoyl]indan-2-yl]acetic acid
5. 2-[2-[(4-piperazin-1-ylsulfonyl-1,3-benzothiazol-2-yl) methylcarbamoyl]indan-2-yl]acetic acid
6. 2-[2-[[4-(3-aminopyrrolidin-1-yl) sulfonyl-1,3-benzothiazol-2-yl]methylcarbamoyl]indan-2-yl]acetic acid
7. 2-[2-[(4-methylsulfonyl-1,3-benzothiazol-2-yl) methylcarbamoyl]indan-2-yl]acetic acid
8. 2-[2-[[6-methoxy-5-[2-(4-methylpiperazin-1-yl)-2-oxo-ethoxy]-1,3-benzothiazol-2-yl]methylcarbamoyl]indan-2-yl]acetic acid
9. 2-[2-[[6-methoxy-5-(2-morpholinoethoxy)-1,3-benzothiazol-2-yl]methylcarbamoyl]indan-2-yl]acetic acid
10. 2-[5,6-difluoro-2-[[6-methoxy-5-(2-morpholinoethoxy)-1,3-benzothiazol-2-yl]methylcarbamoyl]indan-2-yl]acetic acid
11. 2-[5,6-difluoro-2-[[6-methoxy-5-[(1-methyl-4-piperidyl) methoxy]-1,3-benzothiazol-2-yl]methylcarbamoyl]indan-2-yl]acetic acid
12. 2-[5,6-difluoro-2-[[6-methoxy-5-[2-(4-methylpiperazin-1-yl)-2-oxo-ethoxy]-1,3-benzothiazol-2-yl]methylcarbamoyl]indan-2-yl]acetic acid
13. 2-[5,6-difluoro-2-[[6-methoxy-5-[2-(4-methylmorpholin-4-ium-4-yl) ethoxy]-1,3-benzothiazol-2-yl]methylcarbamoyl]indan-2-yl]acetate
14. 2-[2-[[5-[2-(4,4-dimethylpiperazin-4-ium-1-yl)-2-oxo-ethoxy]-6-methoxy-1,3-benzothiazol-2-yl]methylcarbamoyl]-5,6-difluoro-indan-2-yl]acetate
15. 2-[5,6-difluoro-2-[[6-methoxy-5-[3-(4-methylmorpholin-4-ium-4-yl) propoxy]-1,3-benzothiazol-2-yl]methylcarbamoyl] indan-2-yl]acetate
16. 2-[2-[[6-methoxy-5-[3-(4-methylmorpholin-4-ium-4-yl) propoxy]-1,3-benzothiazol-2-yl]methylcarbamoyl]indan-2-yl] acetate
17. 2-[2-[[5-[(1,1-dimethylpiperidin-1-ium-4-yl) methoxy]-6-methoxy-1,3-benzothiazol-2-yl]methylcarbamoyl]indan-2-yl]acetate
18. 2-[2-[[5-[3-[diethyl(methyl) ammonio]propoxy]-6-methoxy-1,3-benzothiazol-2-yl]methylcarbamoyl]indan-2-yl]acetate
19. 2-[5,6-difluoro-2-[[6-methoxy-5-[3-(1-methylpyrrolidin-1-ium-1-yl) propoxy]-1,3-benzothiazol-2-yl]methylcarbamoyl]indan-2-yl]acetate
20. 2-[2-[[5-[3-[2-hydroxyethyl (dimethyl) ammonio] propoxy]-6-methoxy-1,3-benzothiazol-2-yl]methylcarbamoyl] indan-2-yl]acetate
21. 2-[5,6-difluoro-2-[[5-[3-[2-hydroxyethyl (dimethyl) ammonio]propoxy]-6-methoxy-1,3-benzothiazol-2-yl]methylcarbamoyl]indan-2-yl]acetate
22. 2-[2-[[5-[3-[bis (2-hydroxyethyl)-methyl-ammonio] propoxy]-6-methoxy-1,3-benzothiazol-2-yl]methylcarbamoyl]indan-2-yl acetate
23. 2-[2-[[5-[3-[bis (2-hydroxyethyl)-methyl-ammonio] propoxy]-6-methoxy-1,3-benzothiazol-2-yl]methylcarbamoyl]-5,6-difluoro-indan-2-ylacetate
24. 2-[2-[[5-[2-(4-methylpiperazin-1-yl)-2-oxo-ethoxy]-1,3-benzothiazol-2-yl]methylcarbamoyl]indan-2-yl] acetic acid
25. 2-[2-[5-[2-(4-methylpiperazin-1-yl)ethoxy]-1,3-benzothiazol-2-yl]methylcarbamoyl]indan-2-yl]acetic acid
26. 2-[2-[[6-[3-(dimethylamino)azetidine-1-carbonyl]-1,3-benzothiazol-2-yl]methylcarbamoyl]indan-2-yl]acetic acid
27. 2-[2-[[5-(4-methylpiperazine-1-carbonyl)-1,3-benzothiazol-2-yl]methylcarbamoyl]indan-2-yl]acetic acid
28. 2-[2-[[5-[2-(dimethylamino) ethylcarbamoyl]-1,3-benzothiazol-2-yl]methylcarbamoyl]indan-2-yl]acetic acid
29. 2-[2-[[6-(4-methylpiperazine-1-carbonyl)-1,3-benzothiazol-2-yl]methylcarbamoyl]indan-2-yl]acetic acid
30. 2-[2-[[6-[2-(dimethylamino)ethylcarbamoyl]-1,3-benzothiazol-2-yl]methylcarbamoyl]indan-2-yl]acetic acid
31. 2-[2-[5-[4-[3-(dimethylamino)propyl]piperazine-1-carbonyl]-1,3-benzothiazol-2-yl]methylcarbamoyl]indan-2-yl]acetic acid
32. 2-[2-[[5-[3-(dimethylamino)azetidine-1-carbonyl]-1,3-benzothiazol-2-yl]methylcarbamoyl]indan-2-yl]acetic acid
33. 2-[2-[[6-methoxy-5-(4-methylpiperazine-1-carbonyl)-1,3-benzothiazol-2-yl]methylcarbamoyl]indan-2-yl]acetic acid
34. 2-[5,6-difluoro-2-[[6-methoxy-5-(4-methylpiperazine-1-carbonyl)-1,3-benzothiazol-2-yl]methylcarbamoyl]indan-2-yl]acetic acid
35. 2-[2-[[5-(4,4-dimethylpiperazin-4-ium-1-carbonyl)-6-methoxy-1,3-benzothiazol-2-yl]methylcarbamoyl]-5,6-difluoro-indan-2-yl]acetate
36. 2-[2-[[5-[3-(dimethylamino) azetidine-1-carbonyl]-6-methoxy-1,3-benzothiazol-2-yl]methylcarbamoyl]indan-2-yl]acetic acid
37. 2-[2-[[5-[3-(dimethylamino) azetidine-1-carbonyl]-6-methoxy-1,3-benzothiazol-2-yl]methylcarbamoyl]-5,6-difluoro-indan-2-yl]acetic acid
38. 2-[2-[[5-[4-(dimethylamino) piperidine-1-carbonyl]-6-methoxy-1,3-benzothiazol-2-yl]methylcarbamoyl] indan-2-yl]acetic acid
39. 2-[2-[[6-methoxy-5-[4-(trimethylammonio) piperidine-1-carbonyl]-1,3-benzothiazol-2-yl]methylcarbamoyl]indan-2-yl]acetate
40. 2-[2-[[5-[2-[(dimethylamino) methyl]morpholine-4-carbonyl]-6-methoxy-1,3-benzothiazol-2-yl]methylcarbamoyl] indan-2-yl]acetic acid
41. 2-[2-[[6-methoxy-5-[2-[(trimethylammonio) methyl] morpholine-4-carbonyl]-1,3-benzothiazol-2-yl]methylcarbamoyl]indan-2-yl]acetate
42. 2-[2-[[6-methoxy-5-[3-(trimethylammonio) azetidine-1-carbonyl]-1,3-benzothiazol-2-yl]methylcarbamoyl]indan-2-yl]acetate
43. 2-[5,6-difluoro-2-[[6-methoxy-5-[3-(trimethylammonio) azetidine-1-carbonyl]-1,3-benzothiazol-2-yl] methylcarbamoyl]indan-2-yl]acetate
44. 2-[2-[5-[(1,1-dimethylpiperidin-1-ium-4-yl) methoxy]-6-methoxy-1,3-benzothiazol-2-yl]methylcarbamoyl]-5,6-difluoro-indan-2-yl]acetate
45. 2-[2-[[6-methoxy-5-(4-methylpiperazin-1-yl) sulfonyl-1,3-benzothiazol-2-yl]methylcarbamoyl]indan-2-yl]acetic acid
46. 2-[2-[5-[[4-(dimethylamino)-1-piperidyl]sulfonyl]-6-methoxy-1,3-benzothiazol-2-yl]methylcarbamoyl]indan-2-yl]acetic acid
47. 2-[2-[[6-methoxy-5-[4-(trimethylammonio)-1-piperidyl]sulfonyl]-1,3-benzothiazol-2-yl]methylcarbamoyl] indan-2-yl]acetate 48. 2-[2-[(6-cyano-1,3-benzothiazol-2-yl) methylcarbamoyl]indan-2-yl]acetic acid
49. 2-[2-[(5-cyano-1,3-benzothiazol-2-yl) methylcarbamoyl]indan-2-yl]acetic acid or a pharmaceutically acceptable salt thereof.

12. A pharmaceutical composition comprising (i) the compound of claim 1 and (ii) at least one pharmaceutically acceptable carrier or diluent.

13. The pharmaceutical composition of claim 12, further comprising (iii) an antibiotic agent.

14. The pharmaceutical composition of claim 13, wherein the antibiotic agent is selected from tobramycin, neomycin, streptomycin, gentamycin, ceftazidime, ticarcillin, piperacillin, tazobactam, imipenem, meropenem, rifampicin, ciprofloxacin, amikacin, colistin, aztreonam, azithromycin and levofloxacin.

15. A combination of (i) the compound of claim 1, and (ii) an antibiotic agent.

16. The combination of claim 15, wherein the antibiotic agent is selected from tobramycin, neomycin, streptomycin, gentamycin, ceftazidime, ticarcillin, piperacillin, tazobactam, imipenem, meropenem, rifampicin, ciprofloxacin, amikacin, colistin, aztreonam, azithromycin and levofloxacin.

17. A method of treating or preventing bacterial infection in a subject in need thereof, said method comprising administering an effective amount of the compound of claim 1 to said subject.

18. The method of claim 17, wherein the bacterial infection is caused by *Bacillus, Pseudomonas, Staphylococcus, Streptococcus, Listeria, Burkholderia* or *Escherichia*.

19. The method of claim 17, wherein the subject is suffering from or at risk of pneumonia.

20. The method of claim 17, wherein the subject suffers from cystic fibrosis.

21. A method of treating or preventing inflammation in a subject, said method comprising administering an effective amount of the compound of claim 1 to said subject.

22. The method of claim 21, wherein the inflammation is a respiratory tract inflammation and/or is caused by a bacterial infection.

23. The method of claim 21, wherein the subject suffers from cystic fibrosis, chronic obstructive pulmonary disease (COPD), bronchiectasis, and/or ventilator-associated pneumonia (VAP).

24. The compound of claim 1, which compound is 2-[2-[[5-[3-(bis (2-hydroxyethyl)-methyl-ammonio]propoxy]-6-methoxy-1,3-benzothiazol-2-yl]methylcarbamoyl]-5,6-difluoro-indan-2-yl)acetate or a pharmaceutically acceptable salt thereof.

25. The compound of claim 1, wherein
$R^1$ is OH, or where the compound of Formula (I) contains a positively charged nitrogen atom, $R^1$ may be O$^-$, such that the compound forms a zwitterion;
$R^2$ is H;
each $R^3$ group is independently fluorine;
n is an integer from 0 to 2;
$R^4$ is H;
L is —CH$_2$—;
p is 1;
$R^5$ is —OMe;
each $R^6$ is independently —O—$R^{6a}R^A$; wherein each $R^{6a}$ is independently C$_1$ to C$_4$ alkylene and $R^A$ is selected from —NR$^{20}$R$^{30}$ or —N$^+$R$^{20}$R$^{21}$R$^{30}$;
$R^{20}$ and $R^{21}$ are each independently selected from H and C$_1$ to C$_3$ alkyl, which is unsubstituted or is substituted with one —OH group;
each $R^{30}$ is independently selected from C$_2$ to C$_3$ alkyl which is unsubstituted or is substituted with one —OH group.

* * * * *